(12) United States Patent  (10) Patent No.: US 11,976,069 B2
Yu et al.  (45) Date of Patent: May 7, 2024

(54) INHIBITORS OF HISTONE DEACETYLASE USEFUL FOR THE TREATMENT OR PREVENTION OF HIV INFECTION

(71) Applicant: Merck Sharp & Dohme LLC, Rahway, NJ (US)

(72) Inventors: Wensheng Yu, Edison, NJ (US); Joseph A. Kozlowski, Princeton, NJ (US); Dane James Clausen, Rahway, NJ (US); Jian Liu, Edison, NJ (US); James Fells, Hillsborough, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 235 days.

(21) Appl. No.: 17/438,479

(22) PCT Filed: Mar. 16, 2020

(86) PCT No.: PCT/US2020/022882
§ 371 (c)(1),
(2) Date: Sep. 13, 2021

(87) PCT Pub. No.: WO2020/190827
PCT Pub. Date: Sep. 24, 2020

(65) Prior Publication Data
US 2022/0144837 A1 May 12, 2022

Related U.S. Application Data
(60) Provisional application No. 62/821,505, filed on Mar. 21, 2019.

(51) Int. Cl.
*C07D 471/22* (2006.01)
*A61K 31/426* (2006.01)
*A61K 31/438* (2006.01)
*A61K 31/4418* (2006.01)
*A61K 31/4439* (2006.01)
*A61K 31/4748* (2006.01)
*A61K 31/505* (2006.01)
*A61K 31/506* (2006.01)
*A61K 31/513* (2006.01)
*A61K 31/52* (2006.01)
(Continued)

(52) U.S. Cl.
CPC .......... *C07D 471/22* (2013.01); *A61K 31/426* (2013.01); *A61K 31/438* (2013.01); *A61K 31/4418* (2013.01); *A61K 31/4439* (2013.01); *A61K 31/4748* (2013.01); *A61K 31/505* (2013.01); *A61K 31/506* (2013.01); *A61K 31/513* (2013.01); *A61K 31/52* (2013.01); *A61K 31/635* (2013.01); *A61K 31/685* (2013.01); *A61P 31/18* (2018.01); *C07D 487/08* (2013.01); *C07D 491/18* (2013.01); *C07D 498/22* (2013.01)

(58) Field of Classification Search
None
See application file for complete search history.

(56) References Cited

U.S. PATENT DOCUMENTS

| 2014/0135339 A1 | 5/2014 | Bailey et al. |
| 2015/0010541 A1 | 1/2015 | Liu et al. |

(Continued)

FOREIGN PATENT DOCUMENTS

| WO | 2006061638 A2 | 6/2006 |
| WO | 2008110583 A1 | 9/2008 |

(Continued)

OTHER PUBLICATIONS

Boulouard et al., Journal of Heterocyclic Chemistry, 34: 1219-1225 (1995) (Year: 1995).*

(Continued)

*Primary Examiner* — Jeffrey S Lundgren
*Assistant Examiner* — Anthony Joseph Seitz
(74) *Attorney, Agent, or Firm* — Eric Greenwald; John C. Todaro

(57) ABSTRACT

The present invention relates to Compounds of Formula I and Ia and pharmaceutically acceptable salts or prodrug thereof, wherein $R^1$, $R^2$, X, A and B are as defined herein. The present invention also relates to compositions comprising at least one compound of Formula I or Ia, and methods of using the compounds of Formula I or Ia for treating or preventing HIV infection in a subject.

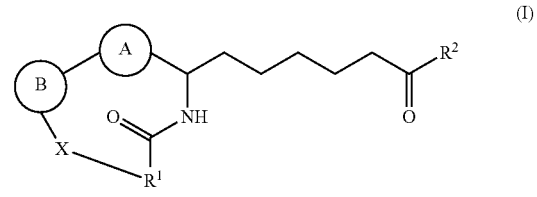

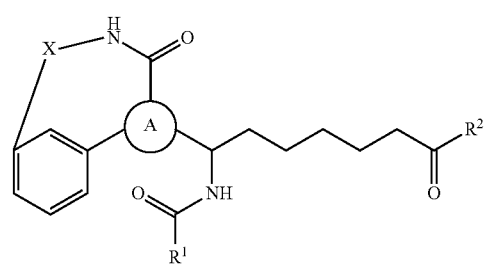

12 Claims, No Drawings

(51) Int. Cl.
*A61K 31/635* (2006.01)
*A61K 31/685* (2006.01)
*A61P 31/18* (2006.01)
*C07D 487/08* (2006.01)
*C07D 491/18* (2006.01)
*C07D 498/22* (2006.01)

(56) References Cited

U.S. PATENT DOCUMENTS

| | | |
|---|---|---|
| 2018/0057510 A1 | 3/2018 | Williams et al. |
| 2018/0230181 A1 | 8/2018 | Marshall et al. |
| 2018/0340009 A1 | 11/2018 | Guerlavais et al. |

FOREIGN PATENT DOCUMENTS

| | | | | |
|---|---|---|---|---|
| WO | 2010009334 A1 | 1/2010 | | |
| WO | WO-2010009334 A1 * | 1/2010 | ........... | A61K 31/429 |
| WO | 2011047926 A1 | 4/2011 | | |
| WO | WO-2011047926 A1 * | 4/2011 | ........... | C07D 245/04 |
| WO | 2014023754 A1 | 2/2014 | | |

OTHER PUBLICATIONS

International Search Report issued for PCT/US20/22882 dated Jun. 15, 2020, 3 pages.
Bresciani, Alberto et al., Improved Selective Class I HDAC and Novel Selective HDAC3 Inhibitors: Beyond Hydroxamic Acids and Benzamides, ACS Med. Chem. Lett., 2019, 481-486, 10(4).
Jones, Philip et al., A Novel Series of Potent and Selective Ketone Histone Deacetylase Inhibitors with Antitumor Activity in Vivo, J. Med. Chem., 2008, 2350-2353, 51(8).
Kinzel, Olaf et al., Discovery of a Potent Class I Selective Ketone Histone Deacetylase Inhibitor with Antitumor Activity in Vivo and Optimized Pharmacokinetic Properties, J. Med. Chem., 2009, 3453-3456, 52.
Marsault, Eric et al., Macrocycles Are Great Cycles: Applications, Opportunities, and Challenges of Synthetic Macrocycles in Drug Discovery, J. Med. Chem., 2011, 1961-2004, 54.
Pescatore, Giovanna et al., Optimization of a series of potent and selective ketone histone deacetylase inhibitors, Bioorganic & Medicinal Chemistry Letters, 2008, 5528-5532, 18.

* cited by examiner

INHIBITORS OF HISTONE DEACETYLASE USEFUL FOR THE TREATMENT OR PREVENTION OF HIV INFECTION

CROSS REFERENCE TO RELATED APPLICATIONS

This application is a U.S. National Phase application under 35 U.S.C. §371 of PCT Application No. PCT/US2020/022882 filed Mar. 16, 2020, which claims priority to U.S. Ser. No. 62/821,505 filed Mar. 21, 2019.

FIELD OF THE INVENTION

The present invention relates to inhibitors of histone deacetylase, compositions comprising at least one inhibitor of histone deacetylase, and methods of using the inhibitors of histone deacetylase for treating or preventing HIV infection in a subject.

BACKGROUND OF THE INVENTION

DNA in the nucleus of the cell exists as a hierarchy of compacted chromatin structures. The basic repeating unit in chromatin is the nucleosome, which consists of a histone octamer of proteins in the nucleus of the cell around which DNA is wrapped twice. The orderly packaging of DNA in the nucleus plays an important role in the functional aspects of gene regulation. Covalent modifications of the histones have a key role in altering chromatin higher order structure and function, and ultimately, gene expression. The covalent modification of histones, such as acetylation, occurs by enzymatically mediated process.

Regulation of gene expression through the inhibition of the nuclear enzyme histone deacetylase (HDAC) is one of the several possible regulatory mechanisms whereby chromatin actively can be affected. The dynamic homeostasis of the nuclear acetylation of histone can be regulated by the opposing activity of the enzymes histone acetyl transferase (HAT) and histone deacetylase (HDAC). Transcriptionally silent chromatin can be characterized by nucleosomes with low levels of acetylated histones. Acetylation reduces the positive charge of histones, thereby expanding the structure of the nucleosome and facilitating the interaction of transcription factors with the DNA. Removal of the acetyl group restores the positive charge, condensing the structure of the nucleosome. While histone acetylation can activate DNA transcription, enhancing gene expression, histone deacetylase can reverse the process and can serve to repress gene expression. Inhibition of the histone deacetylase (HDAC inhibition) can also increase the activation of DNA transcription. See, for example, Grunstein, Nature, 389, 349-352 (1997); Pazin et al., Cell 89, 325-328 (1997); Wade et al., Trends Biochem Sci. 22, 128-132 (1997); and Wolffe, Science 272, 371-372 (1996).

With the introduction of combination antiretroviral therapy (ART), HIV became a controllable chronic disease. The combination of ART (cART) targets specific stages of the viral life cycle, and is effective at combatting active viral load down to undetectable levels. However, HIV persists within the body of infected individuals undergoing therapy, and cessation of ART leads to a viral rebound within 3-4 weeks. The HIV can persist in resting memory and naïve CD4+ T cells and other long-lived cells, such as infected astrocytes and cells of macrophage lineage. HIV can persist in these resting cells by establishing a latent or "silent" infection. In these cells, virus is integrated into the host genome, but viral production does not occur as a result of inhibition of both viral transcriptions from proteins. However, these latently infected cells still do contain replication competent virus, and once cART is stopped, rebound in plasma HIV RNA is observed in nearly all patients.

One approach currently being explored to eliminate latently infected CD4+ T cells is to activate viral production from these cells in the presence of cART, when the production of the virus should kill the infected cells. Histone deacetylase inhibitors have shown promise in vitro in activating virus production from latent infected cells, and therefore this class of drugs is being studied as part of a strategy aimed at a cure of HIV.

Eleven members of the HDAC family has been identified in humans, which share a conserved catalytic domain and are grouped into two classes: class I (1,2,3,8), homologous to yeast Rpd3; and class IIa (4,5,7,9) and IIb (6, 10), homologous to yeast Hdal. HDAC 11 shares homology with both classes, but is at the same time distinct from all the other ten subtypes. The first generation of HDAC inhibitors (HDACi) are promising therapeutic agents against cancer and other diseases, and showed in vitro activation of virus production from latent infected cells. However, due to their poor selectivity, those that entered clinical trials, all show similar adverse effects. The poorly selective HDACi's are not suitable for healthy HIV patents on cART, thus the interest is high for the discovery and development of novel and subtype selective HDAC inhibitors.

SUMMARY OF THE INVENTION

In one aspect, the present invention provides Compounds of Formula I:

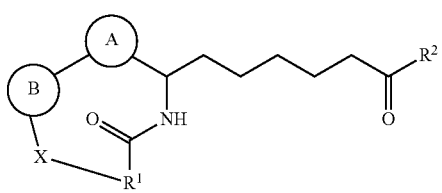

or a pharmaceutically acceptable salt thereof,
wherein

is a five-membered heteroaryl ring which is optionally substituted with halo, cyano or $C_{1-3}$ alkyl;

is heteroaryl, which may be bicyclic or tricyclic, is optionally substituted with one to three groups independently selected from the group consisting of halo, oxo, cyano, $R^3$ and $OR^3$;

$R^1$ is
(a) heterocyclyl, which may be monocyclic or bicyclic,
(b) —$C_{1-3}$ alkyl-N($R^3$)—,
wherein said heterocyclyl groups are optionally substituted with one to two groups independently selected from the group consisting of halo, cyano, oxo, $R^3$ and $OR^3$;
X is —$(CH_2)_n$—, —$(CH_2)_m CH=CH(CH_2)_p$— or —$(CH_2)_m$—O—$(CH_2)_p$—;
$R^2$ is $C_{1-6}$ alkyl;
each $R^3$ is independently hydrogen or $C_{1-6}$ alkyl, which is optionally substituted with one to three halo;
n is an integer between four and eight;
m is an integer between zero and four;
p is an integer between one and five.

In another aspect, the present invention provides Compounds of Formula Ia:

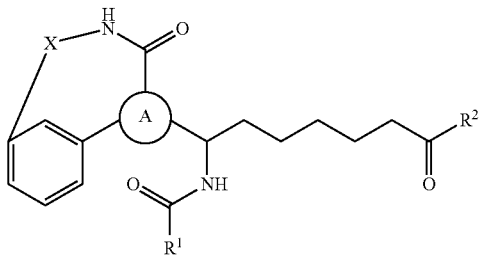

Ia or a pharmaceutically acceptable salt thereof,
wherein

Ⓐ is a five-membered heteroaryl ring which is optionally substituted with halo, cyano or $C_{1-3}$ alkyl;
$R^1$ is
(a) heterocyclyl, which may be monocyclic or bicyclic,
(b) —$C_{1-3}$ alkyl-N($R^3$)—,
wherein said heterocyclyl groups are optionally substituted with one to two groups independently selected from the group consisting of halo, cyano, oxo, $R^3$ and $OR^3$;
X is —$(CH_2)_n$—, —$(CH_2)_m CH=CH(CH_2)_p$— or —$(CH_2)_m$—O—$(CH_2)_p$—;
$R^2$ is $C_{1-6}$ alkyl;
each $R^3$ is independently hydrogen or $C_{1-6}$ alkyl, which is optionally substituted with one to three halo;
n is an integer between four and eight;
m is an integer between zero and four;
p is an integer between one and five.

The Compounds of Formula I and Ia and pharmaceutically acceptable salts or prodrugs thereof may be useful, for example, for activating HIV latency for potential complete cure of HIV infection alone or in combination with cART and/or other HIV treatments.

Accordingly, the present invention provides methods for treating or preventing HIV infection in a subject, comprising administering to the subject an effective amount of at least one compound of Formula I or Ia.

The details of the invention are set forth in the accompanying detailed description below.

Although any methods and materials similar to those described herein may be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes to inhibitors of histone deacetylase, compositions comprising at least one inhibitor of histone deacetylase, and methods of using the inhibitors of histone deacetylase for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of the compound of Formula I or Ia and/or an additional therapeutic agent, or a composition thereof that is effective in inhibiting HIV replication and in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The terms "treating" or "treatment" as used herein with respect to an HIV viral infection or AIDS, includes inhibiting the severity of HIV infection or AIDS, i.e., arresting or reducing the development of the HIV infection or AIDS or its clinical symptoms; or relieving the HIV infection or AIDS, i.e., causing regression of the severity of HIV infection or AIDS or its clinical symptoms.

The terms "preventing," or "prohylaxis," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "halo," as used herein, means —F, —Cl, —Br or —I.

The term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on. Bicyclic cycloalkyl ring systems include fused ring systems, where two rings share two atoms, and spiro ring systems, where two rings share one atom.

The term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: azaindolyl, benzoimidazolyl, benzisoxazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyrazolopyrimidinyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, dihydrobenzodioxinyl, dihydropyrazoloxazinyl, dihydropyrazolyothiazinedioxidyl, methylenedioxybenzene, benzothiazolyl, benzothienyl, quinolinyl, isoquinolinyl, oxazolyl, tetra-hydroquinoline and 3-oxo-3,4dihydro-2N-benzo[b][1,4]thiazine. If the heteroaryl contains nitrogen atoms, it is understood that the corresponding N-oxides thereof are also encompassed by this definition.

The term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: azaspirononanyl, azaspirooctanyl, azetidinyl, dioxanyl, oxadiazaspirodecenyl, oxaspirooctanyl, oxazolidinonyl, piperazinyl, piperidinyl, pyrrolidinyl, morpholinyl, thiomorpholinyl, tetrahydrofumayl, tetrahydropyranyl, dihydropiperidinyl, tetrahydrothiophenyl and the like. If the heterocycle contains a nitrogen, it is understood that the corresponding N-oxides thereof are also encompassed by this definition.

"Celite®" (Fluka) diatomite is diatomaceous earth, and can be referred to as "celite".

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., $R^3$) occurs more than one time in any constituent or in Formula I or Ia, its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a compound of Formula I or Ia or a pharmaceutically acceptable salt of the compound. The transformation may occur by various mechanisms (e.g., by metabolic or chemical processes), such as, for example, through hydrolysis in blood. For example, if a compound of Formula I or Ia or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as 3-dimethylaminoethyl), carbamoyl-($C_1$-$C_2$)alkyl, N,N-di($C_1$-$C_2$) alkylcarbamoyl-($C_1$-$C_2$)alkyl and piperidino-, pyrrolidino- or morpholino($C_2$-$C_3$)alkyl, and the like.

Similarly, if a compound of Formula I or Ia contains an alcohol functional group, a prodrug can be formed by the replacement of one or more of the hydrogen atoms of the alcohol groups with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a compound of Formula I or Ia incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$) alkyl, ($C_3$-$C_7$) cycloalkyl, benzyl, a natural a aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$) alkyl; carboxy ($C_1$-$C_6$)alkyl; amino($C_1$-$C_4$)alkyl or mono-N— or di-N,N—($C_1$-$C_6$)alkylaminoalkyl; —C(Y$^4$)Y$^5$ wherein Y$^4$ is H or methyl and Y$^5$ is mono-N— or di-N, N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or tri-phosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTech.*, 5(1), article 12 (2004); and A. L. Bingham et al, *Chem. Commun.*, 603-604 (2001). Atypical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The compound of Formula I or Ia can form salts which are also within the scope of this invention. Reference to a compound of Formula I or Ia herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I or Ia contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula I or Ia may be formed, for example, by reacting a compound of Formula I or Ia with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the compound of Formula I or Ia may be atropisomers (e.g., substituted biaryls) and are considered as part of this invention. Enantiomers can also be directly separated using chiral chromatographic techniques.

It is also possible that the compound of Formula I or Ia may exist in different tautomeric forms, and all such forms are embraced within the scope of the invention. For example, all keto-enol and imine-enamine forms of the compounds are included in the invention.

Unless otherwise indicated, all stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a compound of Formula I or Ia incorporates a double bond or a fused ring, both the cis- and trans-forms, as well as mixtures, are embraced within the scope of the invention.

When a substituent on a chiral carbon atom is depicted without specific stereochemistry (by using a straight line bond to a chiral center), it is to be understood that both the alpha and beta configurations of said substituent group are to be considered part of the present invention. For example, the compound of the present invention, which is drawn as follows:

is understood to encompass both stereoisomers at the indicated chiral center, the structures of which are as follows:

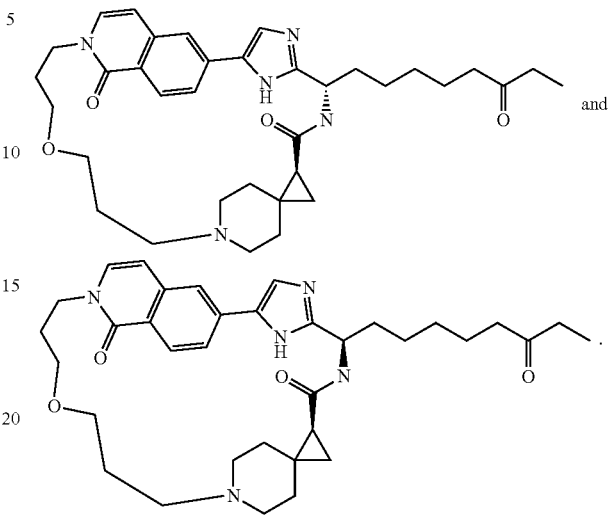

In the Examples section below, compounds of the present invention that have been purified as individual stereoisomers are sometimes depicted in non-stereospecific form but identified using one or more of the terms: "diastereomer 1," "diastereomer 2," "isomer 1," "isomer 2," "enantiomer A" and "enantiomer B." In this instance, the absolute stereochemistry of each isolated diastereomer and enantiomeric center has not been determined and the terms used above are used to represent each individual purified stereochemically pure compound.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula I and Ia, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I and Ia. For example, different isotopic forms of hydrogen (H) include protium ($^1$H) and deuterium ($^2$H). Protium is the predominant hydrogen isotope found in nature. Enriching for deuterium may provide certain therapeutic advantages, such as increasing in vivo half-life or reducing dosage requirements, or may provide a compound useful as a standard for characterization of biological samples. Isotopically-enriched Compounds of Formula I and Ia can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula I or Ia has one or more of its hydrogen atoms replaced with deuterium.

The compounds of Formula I and Ia may be useful in human and veterinary medicine for treating or preventing HIV infection in a subject. In one embodiment, the compounds of Formula I and Ia can be inhibitors of HIV viral replication. In a specific embodiment, the compounds of Formula I and Ia are inhibitors of HIV-1. Accordingly, the compounds of Formula I and Ia may be useful for treating HIV infections and AIDS. In accordance with the invention, the compounds of Formula I and Ia can be administered to a subject in need of treatment or prevention of HIV infection.

Accordingly, in one embodiment, the invention provides methods for treating HIV infection in a subject comprising administering to the subject an effective amount of at least one compound of Formula I or Ia or a pharmaceutically acceptable salt thereof. In a specific embodiment, the present invention provides methods for treating AIDS in a subject comprising administering to the subject an effective amount of at least one compound of Formula I or Ia or a pharmaceutically acceptable salt thereof.

The Compounds of Formula I and Ia

The present invention provides Compounds of Formula I:

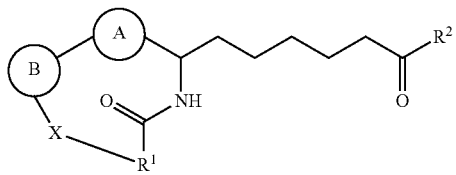

wherein

is a five-membered heteroaryl ring which is optionally substituted with halo, cyano or $C_{1-3}$ alkyl;

is heteroaryl, which may be bicyclic or tricyclic, is optionally substituted with one to three groups independently selected from the group consisting of halo, oxo, cyano, $R^3$ and $OR^3$;
$R^1$ is
(a) heterocyclyl, which may be monocyclic or bicyclic,
(b) —$C_{1-3}$ alkyl-N($R^3$)—,
wherein said heterocyclyl groups are optionally substituted with one to two groups independently selected from the group consisting of halo, cyano, oxo, $R^3$ and $OR^3$;
X is —$(CH_2)_n$—, —$(CH_2)_m CH=CH(CH_2)_p$— or —$(CH_2)_m$—O—$(CH_2)_p$—;
$R^2$ is $C_{1-6}$ alkyl;
each $R^3$ is independently hydrogen or $C_{1-6}$ alkyl, which is optionally substituted with one to three halo;
n is an integer between four and eight;
m is an integer between zero and four;
p is an integer between one and five;
or a pharmaceutically acceptable salt thereof.

The present invention also provides Compounds of Formula Ia:

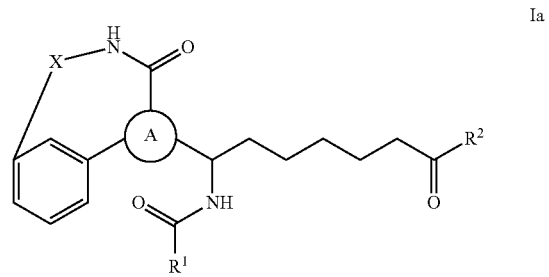

or a pharmaceutically acceptable salt thereof,
wherein

is a five-membered heteroaryl ring which is optionally substituted with halo, cyano or $C_{1-3}$ alkyl;
$R^1$ is
(a) heterocyclyl, which may be monocyclic or bicyclic,
(b) —$C_{1-3}$ alkyl-N($R^3$)—,
wherein said heterocyclyl groups are optionally substituted with one to two groups independently selected from the group consisting of halo, cyano, oxo, $R^3$ and $OR^3$;
X is —$(CH_2)_n$—, —$(CH_2)_m CH=CH(CH_2)_p$— or —$(CH_2)_m$—O—$(CH_2)_p$—;
$R^2$ is $C_{1-6}$ alkyl;
each $R^3$ is independently hydrogen or $C_{1-6}$ alkyl, which is optionally substituted with one to three halo;
n is an integer between four and eight;
m is an integer between zero and four;
p is an integer between one and five.
In an embodiment of the invention,

is imidazolyl or oxazolyl. In a class of the embodiment,

is imidazolyl. In another class of the embodiment,

is oxazofll.
In an embodiment of the invention,

is dihydroisoquinolinyl, tetrahydroepaminonaphthalenyl or quinolinyl, wherein said dihydroisoquinolinyl, tetrahydroepaminonaphthalenyl or quinolinyl groups are optionally substituted with oxo or $OR^3$. In a class of the embodiment, (B)

is dihydroisoquinolinyl, which is optionally substituted with $OCH_3$. In another class of the embodiment, (B)

is tetrahydroepaminonaphthalenyl. In another class of the embodiment, (B)

is quinolinyl.

In an embodiment of the invention, $R^1$ is azaspirooctanyl or —$CH_2N(CH_3)$—. In a class of the embodiment, $R^1$ is azaspirooctanyl. In another class of the embodiment, $R^1$ is —$CH_2N(CH_3)$—.

In an embodiment of the invention, $R^2$ is ethyl.

In an embodiment of the invention, $R^3$ is hydrogen or methyl. In a class of the embodiment, $R^3$ is hydrogen. In another class of the embodiment, $R^3$ is methyl.

In an embodiment of the invention, X is —$(CH_2)_n$—. In another embodiment of the invention, X is —$(CH_2)_m$CH=CH$(CH_2)_p$—. In another embodiment of the invention, X is —$(CH_2)_m$—O—$(CH_2)_p$—.

In an embodiment of the invention, n is four. In another embodiment of the invention, n is five. In another embodiment of the invention, n is six. In another embodiment of the invention, n is seven. In another embodiment of the invention, n is eight.

In an embodiment of the invention, m is zero. In another embodiment of the invention, m is one. In another embodiment of the invention, m is two. In another embodiment of the invention, m is three. In another embodiment of the invention, m is four.

In an embodiment of the invention, p is one. In another embodiment of the invention, p is two. In another embodiment of the invention, p is three. In another embodiment of the invention, p is four. In another embodiment of the invention, p is five.

In another embodiment, the Compounds of Formula I and Ia are in substantially purified form.

It is to be understood that any of the aforementioned embodiments may be combined with one or more separate embodiments.

Other embodiments of the present invention include the following:

(a) A pharmaceutical composition comprising an effective amount of a Compound of Formula I or Ia, and a pharmaceutically acceptable carrier.

(b) The pharmaceutical composition of (a), further comprising a second therapeutic agent selected from the group consisting of HIV antiviral agents, immunomodulators, anti-infective agents, vaccines, and antibodies.

(c) The pharmaceutical composition of (b), wherein the HIV antiviral agent is an antiviral selected from the group consisting of HIV protease inhibitors, HIV integrase inhibitors and HIV NNRTI inhibitors.

(d) A pharmaceutical combination that is (i) a Compound of Formula I or Ia and (ii) a second therapeutic agent selected from the group consisting of HIV antiviral agents, immunomodulators, and anti-infective agents, vaccines, and antibodies; wherein the Compound of Formula I or Ia and the second therapeutic agent are each employed in an amount that renders the combination effective for inhibiting HIV replication, or for treating HIV infection and/or reducing the likelihood or severity of symptoms of HIV infection, and eradicates HIV infection.

(e) The combination of (d), wherein the HIV antiviral agent is an antiviral selected from the group consisting of HIV protease inhibitors, HIV integrase inhibitors and HIV NNRTI inhibitors.

(f) A method of inhibiting HIV replication in a subject in need thereof which comprises administering to the subject an effective amount of a Compound of Formula I or Ia.

(g) A method of treating HIV infection and/or reducing the likelihood or severity of symptoms of HIV infection in a subject in need thereof which comprises administering to the subject an effective amount of a Compound of Formula I or Ia.

(h) The method of (g), wherein the Compound of Formula I or Ia is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, HIV integrase inhibitors and HIV NNRTI inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

Additional embodiments of the present invention include the following:

(l) A pharmaceutical composition comprising an effective amount of a pharmaceutically acceptable salt of a Compound of Formula I or Ia, and a pharmaceutically acceptable carrier.

(m) The pharmaceutical composition of (1), further comprising a second therapeutic agent selected from the group consisting of HIV antiviral agents, immunomodulators, anti-infective agents, vaccines and antibodies.

(n) The pharmaceutical composition of (m), wherein the HIV antiviral agent is an antiviral selected from the group consisting of HIV protease inhibitors and HIV NNRTI inhibitors.

(o) A pharmaceutical combination that is (i) a pharmaceutically acceptable salt of a Compound of Formula I or Ia and (ii) a second therapeutic agent selected from the group consisting of HIV antiviral agents, immunomodulators, and anti-infective agents; wherein the pharmaceutically acceptable salt of the Compound of Formula I or Ia and the second therapeutic agent are each employed in an amount that renders the combination effective for inhibiting HIV replication, or for treating HIV infection and/or reducing the likelihood or severity of symptoms of HIV infection.

(p) The combination of (o), wherein the HIV antiviral agent is an antiviral selected from the group consisting of HIV protease inhibitors and HIV NNRTI inhibitors.

(q) A method of inhibiting HIV replication in a subject in need thereof which comprises administering to the subject an effective amount of a pharmaceutically acceptable salt of a Compound of Formula I or Ia.

(r) A method of treating HIV infection and/or reducing the likelihood or severity of symptoms of HIV infection in a subject in need thereof which comprises administering to the subject an effective amount of a pharmaceutically acceptable salt of a Compound of Formula I or Ia.

(s) The method of (r), wherein the pharmaceutically acceptable salt of the Compound of Formula I or Ia is administered in combination with an effective amount of at least one second therapeutic agent selected from the group consisting of HIV antiviral agents, immunomodulators, and anti-infective agents.

(t) The method of (s), wherein the HIV antiviral agent is an antiviral selected from the group consisting of HIV protease inhibitors and HIV NS5B polymerase inhibitors.

(u) A method of inhibiting HIV replication in a subject in need thereof which comprises administering to the subject the pharmaceutical composition of (l), (m) or (n) or the combination of (o) or (p).

(v) A method of treating HIV infection and/or reducing the likelihood or severity of symptoms of HIV infection in a subject in need thereof which comprises administering to the subject the pharmaceutical composition of (l), (m) or (n) or the combination of (o) or (p).

Further embodiments of the present invention include the following:

(w) A pharmaceutical composition comprising an effective amount of a Compound of Formula I or Ia or a pharmaceutically acceptable salt thereof, and a pharmaceutically acceptable carrier.

(x) The pharmaceutical composition of (w), further comprising a second therapeutic agent selected from the group consisting of HIV antiviral agents, immunomodulators, and anti-infective agents.

(y) The pharmaceutical composition of (x), wherein the HIV antiviral agent is an antiviral selected from the group consisting of HIV protease inhibitors and HIV NNRTI inhibitors.

(z) A pharmaceutical combination that is (i) a Compound of Formula I or Ia and (ii) or a pharmaceutically acceptable salt thereof, a second therapeutic agent selected from the group consisting of HIV antiviral agents, immunomodulators, and anti-infective agents; wherein the Compound of Formula I or Ia and the second therapeutic agent are each employed in an amount that renders the combination effective for inhibiting HIV replication, or for treating HIV infection and/or reducing the likelihood or severity of symptoms of HIV infection.

(aa) The combination of (z), wherein the HIV antiviral agent is an antiviral selected from the group consisting of HIV protease inhibitors and HIV NNRTI inhibitors.

(bb) A method of inhibiting HIV replication in a subject in need thereof which comprises administering to the subject an effective amount of a Compound of Formula I or Ia or a pharmaceutically acceptable salt thereof.

(cc) A method of treating HIV infection and/or reducing the likelihood or severity of symptoms of HIV infection in a subject in need thereof which comprises administering to the subject an effective amount of a Compound of Formula I or Ia or a pharmaceutically acceptable salt thereof.

(dd) The method of (cc), wherein the Compound of Formula I or Ia or pharmaceutically acceptable salt thereof, is administered in combination with an effective amount of at least one second therapeutic agent selected from the group consisting of HIV antiviral agents, immunomodulators, and anti-infective agents.

(ee) The method of (dd), wherein the HIV antiviral agent is an antiviral selected from the group consisting of HIV protease inhibitors and HIV NNRTI inhibitors.

(ff) A method of inhibiting HIV replication in a subject in need thereof which comprises administering to the subject the pharmaceutical composition of (w), (x) or (y) or the combination of (z) or (aa).

(gg) A method of treating HIV infection and/or reducing the likelihood or severity of symptoms of HIV infection in a subject in need thereof which comprises administering to the subject the pharmaceutical composition of (w), (x) or (y) or the combination of (z) or (aa).

The present invention also includes a compound of the present invention for use I in, (ii) as a medicament for, or (iii) in the preparation of a medicament for: (a) medicine; (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(gg) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (gg) above are understood to include all embodiments of the compounds, including such embodiments as result from combinations of embodiments.

Non-limiting examples of the Compounds of Formula I and Ia include compounds 1-15 as set forth in the Examples below:

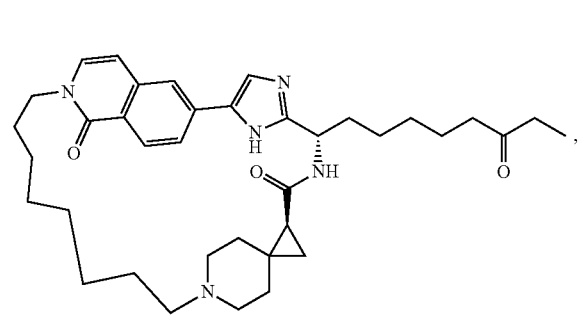

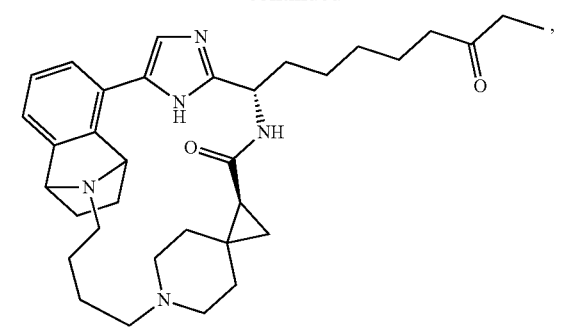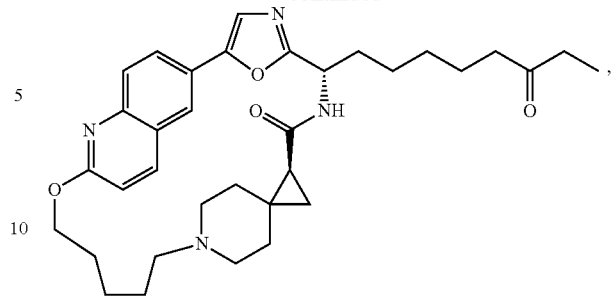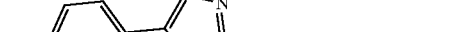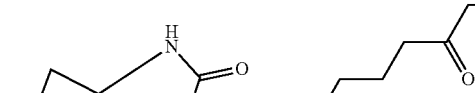

-continued and pharmaceutically acceptable salts thereof.

Methods for Making the Compounds of Formula I and Ia

The Compounds of Formula I and Ia may be prepared from known or readily prepared starting materials, following methods known to one skilled in the art of organic synthesis. Methods useful for making the Compounds of Formula I and Ia are set forth in the Examples below and generalized in the Schemes below. Alternative synthetic pathways and analogous structures will be apparent to those skilled in the art of organic synthesis.

General List of Abbreviations

Abbreviations and acronyms employed herein include the following:
Ac Acetyl
Aq Aqueous
ACN Acetonitrile
AUC Area under the curve
AIBN Azobisisobutyronitrile
BOC tert-butyloxycarbonyl
BPD Bis(pinacolato)diboron
Bu Butyl
Bz Benzoyl
DBU 1,8-Diazabicyclo[5.4.0]undec-7-ene
DCM Dichloromethane
DCE 1,2-Dichloroethane
DIBAL-H Diisobutylaluminium hydride
DIEA, DIPEA or Hünig's base N,N-diisopropylethylamine
DMAP 4-dimethylaminopyridine
DME dimethyoxyethane
DMF dimethylformamide
DMP Dess-Martin periodinane
Dppf 1,1'-Bis(diphenylphosphino)ferrocene
DMSO dimethyl sulfoxide
DTBPF 1,1'-bis(di-tert-butylphosphino)ferrocene
EA Ethyl Acetate
EDC 1-Ethyl-3-(3-dimethylaminopropyl)carbodiimide hydrochloride
EDCI N-ethyl-N'-(3-dimethylaminopropyl)carbodiimide hydrochloride
Et Ethyl
EtOH Ethanol
EtOAc ethyl acetate
G Grams
GI Gastrointenstinal
H Hour
HATU 1-[Bis(dimethylamino)methylene]-1H-1,2,3-triazolo[4,5-b]pyridinium 3-oxide hexafluorophosphate
HIV human immunodeficiency virus
HOBT, HOBt 1-Hydroxybenzotriazole hydrate
HPBCD hydroxypropyl β-cyclodextrin
HPLC high-performance liquid chromatography
mCPBA, CPBA meta-Chloroperoxybenzoic Hz Hertz
IPA Isopropanol
IV Intravenous
iPr Isopropyl
L Liter
LC liquid chromatography
LC/MS liquid chromatography mass spectrometry
LDA Lithium diisopropylamide
LED light-emitting diode
LiHMDS lithium bis(trimethylsilyl)amide
Me Methyl
MeOH Methanol
Mg Milligrams
MHz Megahertz
Min Minute
μL Microliters
mL Milliliters
Mmol Millimoles
MOM-Cl chloromethyl methyl ether
MPLC medium pressure liquid chromatography
MS mass spectrometry
MsCl Methanesulfonyl chloride
NBS N-Bromosuccinimide
NCS N-Chlorosuccinimide
NHS normal human serum
NIS N-Iodosuccinimide
NMO 4-methylmorpholine N-oxide
NMR nuclear magnetic resonance spectroscopy
PBMC peripheral blood mononuclear cell
$Pd_2(dba)_3$ Tris(dibenzylideneacetone)dipalladium(O)
Ph Phenyl
P.O. Oral
PPTS Pyridinium p-toluenesulfonate
PTSA para-toluenesulfonic acid
Pr Propyl
PyBOP Benzotriazol-1-yl-oxytripyrrolidinophosphonium hexafluorophosphate
Rpm revolutions per minute
RT or rt room temperature (ambient, about 25° C.)
sat or sat'd Saturated
SEMCl 2-Chloromethoxyethyl)trimethylsilane
SFC supercritical fluid chromatography
T3P, $T_3P$ 1-Propanephosphonic anhydride solution
TBAF Tetra-n-butylammonium fluoride
tBu tert-butyl
TEA triethylamine ($Et_3N$)
TEMED Tetramethylethylenediamine
TFA trifluoroacetic acid
TFV Tenofovir
TFV-MP Tenofovir monophosphoate
TFV-DP Tenofovir diphosphate
THF Tetrahydrofuran
TMS Tetramethylsilane
Ts Tosyl
UPLC ultrahigh pressure liquid chromatography
UV Ultraviolet
UV/VIS ultraviolet/visible
W Watt
XPhos 2-Dicyclohexylphosphino-2',4',6'-triisopropylbiphenyl General Procedures Starting materials and intermediates are purchased or are made using known procedures, or as otherwise illustrated. The general route applied to the synthesis of compounds of Formula I and Ia is described in the Schemes that follows.

In some cases the order of carrying out the reaction steps in the schemes may be varied to facilitate the reaction or to avoid unwanted reaction products.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC/MS).

Typically the analytical LC-MS system used consisted of a Waters ZQ™ platform with electrospray ionization in positive ion detection mode with an Agilent 1100 series HPLC with autosampler. The column was commonly a Waters Xterra MS C18, 3.0×50 mm, 5 μm or a Waters Acquity UPLC® BEH C18 1.0×50 mm, 1.7 μm. The flow rate was 1 mL/min, and the injection volume was 10 μL. UV detection was in the range 210-400 nm. The mobile phase consisted of solvent A (water plus 0.05% TFA) and solvent B (MeCN plus 0.05% TFA) with a gradient of 100% solvent A for 0.7 min changing to 100% solvent B over 3.75 min, maintained for 1.1 min, then reverting to 100% solvent A over 0.2 min. Alternatively, the column was commonly a Waters Acquity UPLC® BEH C18 1.0×50 mm, 1.7 μm. The flow rate was 0.3 mL/min, and the injection volume was 0.5 μL. UV detection was 215 or 254 nm. Either the mobile phase consisted of solvent A (water plus 0.05% TFA) and solvent B (MeCN plus 0.05% TFA) with a gradient of 90% solvent A changing to 99% solvent B over 1.6 min, maintained for 0.4 min, then reverting to 90% solvent A over 0.1 min or the mobile phase consisted of solvent A (water plus 0.05% TFA) and solvent B (MeCN plus 0.05% TFA) with a gradient of 97% solvent A changing to 4% then 50% solvent B over 0.5 min and 0.9 min, 50%-99% solvent B over 0.2 min, maintained for 0.4 min, then reverting to 90% solvent A over 0.1 min.

Preparative HPLC purifications were usually performed using either a mass spectrometry directed system or a non-mass guided system. Usually they were performed on a Waters Chromatography Workstation configured with LC-MS System consisting of: Waters ZQ™ single quad MS system with Electrospray Ionization, Waters 2525 Gradient Pump, Waters 2767 Injecto/Collector, Waters 996 PDA Detector, the MS Conditions of: 150-750 amu, Positive Electrospray, Collection Triggered by MS, and a Waters SUNFIRE® C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 L, and the UV detection range was 210-400 nm. An alternate preparative HPLC system used was a Gilson Workstation consisting of: Gilson GX-281 Injector/Collector, Gilson UV/VIS-155 Detector, Gilson 322, 333, and 334 Pumps, and a Phenomenex Gemini-NX C-18 5 micron, 50 mm (id)×250 mm column, a Waters XBridge™ C-18 5 micron OBD™, 30 mm (id)×250 mm column, or a Waters SUNFIRE™ C-18 OBD™ 10 micron, 30 mm (id)×150 mm column. The mobile phases consisted of mixtures of acetonitrile (0-90%) in water containing 0.1% or 0.05% TFA. Flow rates were maintained at 50 mL/min for the Waters Xbridge™ column, 90 mL/min for the Phenomenex Gemini column, and 30 mL/min for the Waters SUNFIRE™ column. The injection volume ranged from 1000-8000 μL, and the UV detection range was 210-400 nm. Mobile phase gradients were optimized for the individual compounds. Reactions performed using microwave irradiation were normally carried out using an Emrys Optimizer manufactured by Personal Chemistry, or an Initiator manufactured by Biotage. Reactions performed using photon irradiation were normally carried out using either a second generation Merck photoreactor or a Kessil 34 W blue LED lamp. Concentration of solutions was carried out on a rotary evaporator under reduced pressure. Flash chromatography was usually performed using either a Biotage® Flash Chromatography apparatus (Dyax Corp.), an ISCO CombiFlash® Rf apparatus, or an ISCO Combi-Flash® Companion XL on silica gel (32-63 microns, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CDCl$_3$ solutions, and residual CH$_3$OH peak or TMS was used as internal reference in CD$_3$OD solutions. Coupling constants (J) were reported in hertz (Hz). Chiral analytical chromatography was most commonly performed on one of CHIRALPAK© AS, CHIRALPAK©AD, CHIRALCEL© OD, CHIRAL-CEL® IA, or CHIRALCEL© OJ columns (250×4.6 mm) (Daicel Chemical Industries, Ltd.) with noted percentage of ethanol in hexane (% EtOH/Hex), isopropanol in heptane (% IPA/Hep), ethanol in carbon dioxide (% EtOH/CO$_2$), or isopropanol in carbon dioxide (0% IPA/CO$_2$) as isocratic solvent systems. Chiral preparative chromatography was conducted on one of CHIRALPAK AS, of CHIRALPAK AD, CHIRALCEL® OD, CHIRALCEL® IA, CHIRAL-CEL® OJ columns (20×250 mm) (Daicel Chemical Industries, Ltd.) with desired isocratic solvent systems identified on chiral analytical chromatography or by supercritical fluid (SFC) conditions.

Catalysts are used in the following procedures. "Grubbs II" is also known as (1,3-Bis(2,4,6-trimethylphenyl)-2-imidazolidinylidene)dichloro(phenylmethylene) (tricyclohexylphosphine)ruthenium. "PdCl$_2$(dppf)" is also known as [1,1'-Bis(diphenylphosphino)ferrocene]dichloropalladium (II). "PdCl$_2$(DTBPF)" is also known as [1,1'-Bis(di-tert butylphosphino)ferrocene]dichloropalladium(II). These catalysts are all available from Sigma Aldrich. "M71-S1Pr" is also known as "Umicore Hoveyda Grubbs Catalyst M71 S1Pr" and [1,3-Bis(2,6-diisopropylphenyl)-2-imidazolidinylidene]dichloro[(2-isopropoxy)(5-trifluoroacetamido) benzylidene]ruthenium(II). It is available from Umicore Precious Metals Chemistry USA, LLC, 1305 Main Parkway Catoosa, Okla. 74015.

Several methods for preparing the compounds of this invention are also described in the Examples. Starting materials and intermediates were purchased commercially from common catalog sources or were made using known procedures, or as otherwise illustrated.

Example 1

Preparation of Intermediate A1

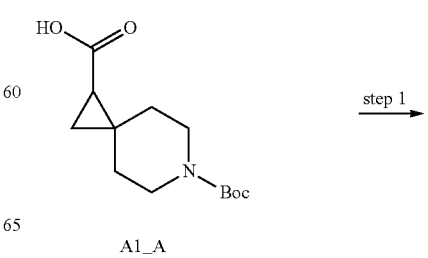

A1_A step 1

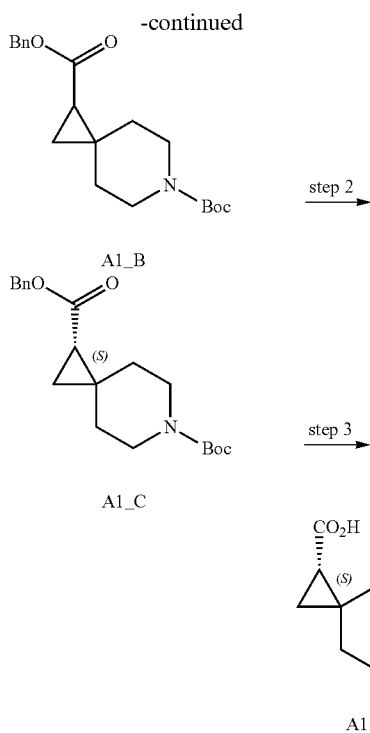

instrument. The racemate was dissolved in isopropanol/DCM. The separation was accomplished using 20% MeOH/$CO_2$, flow rate 200 mL/min, 100 bar, 38° C. The $2^{nd}$ peak is the S isomer A1_C. $^1$H NMR-P2 (400 MHz, $CDCl_3$) δ 7.43-7.29 (m, 5H), 5.18-5.07 (m, 2H), 3.54-3.36 (m, 3H), 3.26-3.16 (m, 1H), 1.73-1.60 (m, 3H), 1.53-1.34 (m, 11H), 1.21 (t, J=5.1 Hz, 1H), 0.96 (dd, J=4.4, 7.9 Hz, 1H).

Step 3: (S)-6-(tert-butoxycarbonyl)-6-azaspiro[2.5]octane-1-carboxylic acid (A1)

A mixture of (S)-1-benzyl 6-tert-butyl 6-azaspiro[2.5]octane-1,6-dicarboxylate (A1_C, 5 g, 14.47 mmol), 10% Pd/C (0.154 g, 1.447 mmol) in MeOH (30 mL) was hydrogenated under $H_2$ (20 psi) at room temperature for 18 h. The mixture was filtered, and the filter cake was washed with MeOH (30×3 mL). The filtrate was concentrated to dryness to give (S)-6-(tert-butoxycarbonyl)-6-azaspiro[2.5]octane-1-carboxylic acid (A1) which was used without further purification. LCMS (ESI) calc'd for $C_{13}H_{21}NO_4$ $[M+H]^+$: 256.2, found: 200.1 (M-55).

Example 2

Preparation of Intermediate A2

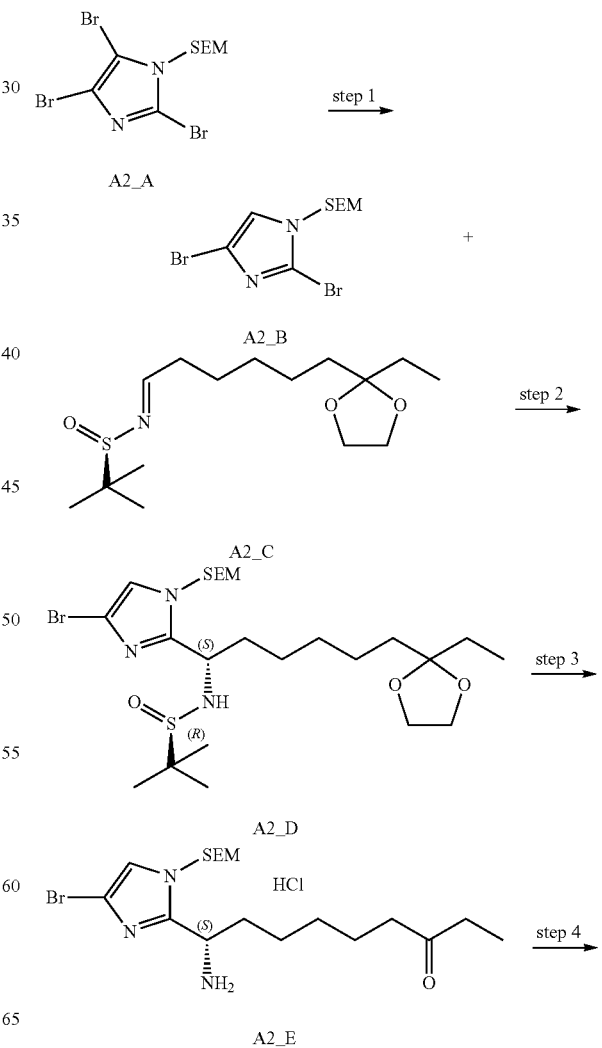

Step 1: 1-benzyl 6-tert-butyl 6-azaspiro[2.5]octane-1,6-dicarboxylate (A1_A)

DBU (235 g, 1.55 mol, 233 mL) was added in one portion to a solution of 6-(tert-butoxycarbonyl)-6-azaspiro[2.5]octane-1-carboxylic acid (A1_A, 330 g, 1.29 mol) in $CH_3CN$ (3.3 L) at 20° C. Benzyl bromide (242 g, 1.42 mol, 168 mL) was added to the suspension at 20° C. which was stirred at 20° C. for 4 h. This reaction was repeated, and the two reactions were combined and concentrated. The residual was dissolved in ethyl acetate (5.5 L) and the precipitate was filtered. The filter cake was washed with ethyl acetate (300 mL*3). The organic phase was washed sequentially with citric acid (10% w/w, 3 L*2), sat. $NaHCO_3$ aqueous (3 L*2), water (2 L), and brine (2 L). The organic phase was dried over $Na_2SO_4$, filtered and concentrated to give a crude product. The crude product was dissolved with petroleum ether (7 L) and the solution was put in a dry ice-acetone bath for 12 h. The solution was decanted and the solid with stirred with petroleum ether (600 mL) for 1 hour. The suspension was filtered, and the filter cake was washed with petroleum ether (30 mL*2) to get the filter cake (400 g). The filtrate was combined and concentrated, and the process was repeated. The solid was combined to give 1-benzyl 6-tert-butyl 6-azaspiro[2.5]octane-1,6-dicarboxylate (A1_B). $^1$H NMR (400 MHz, $CDCl_3$) δ 7.41-7.31 (m, 5H), 5.19-5.07 (m, 2H), 3.55-3.36 (m, 3H), 3.28-3.17 (m, 1H), 1.77-1.61 (m, 3H), 1.49-1.37 (m, 11H), 1.21 (t, J=4.9 Hz, 1H), 0.96 (dd, J=4.5, 7.6 Hz, 1H).

Step 2: (S)-1-benzyl 6-tert-butyl 6-azaspiro[2.5]octane-1,6-dicarboxylate (A1_C)

Racemic 1-benzyl 6-tert-butyl 6-azaspiro[2.5]octane-1,6-dicarboxylate (A1_B) was resolved on a ChiralPak AD column (300×50 mm) under supercritical fluid chromatography (SFC) conditions on a Thar 200 preparative SFC -continued

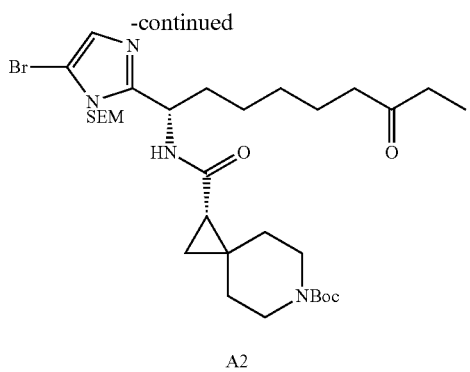

A2

Step 1: Preparation of 2,4-dibromo-1-((2-(trimethyl-silyl)ethoxy)methyl)-1H-imidazole (A2_B)

Into a 10 L 3-necked round-bottom flask which was purged and maintained with an inert atmosphere of nitrogen, was charged with a solution of 2,4,5-tribromo-1-[[2-(trimethylsilyl)ethoxy]methyl]-1H-imidazole (A2_A, 420 g, 965.46 mmol) in tetrahydrofuran (4000 mL). This was followed by the addition of n-BuLi (783 mL, 2.02 equiv) dropwise with stirring at −78° C. The mixture was stirred at −78° C. for 10 min. To this mixture, water was added (17.4 g, 966.67 mmol) at −78° C. The mixture was slowly warmed to −50° C. over 1 h. The mixture was cooled to −78° C. again and Br$_2$ (170 g, 1.06 mol, 1.20 equiv) was added. The mixture was stirred at −78° C. for 30 min. The reaction was then quenched by the addition of 2 L of water. The resulting solution was extracted with 3×2 L of ethyl acetate. The organic layers were combined, washed with 1×1 L of brine, dried over anhydrous sodium sulfate, and concentrated under vacuum. The residue was applied onto a silica gel column with ethyl acetate/petroleum ether (1:30) to afford 2,4-dibromo-1-[[2-(trimethylsilyl)ethoxy]methyl]-1H-imidazole (A2_B).

Step 2: Preparation of (R)-N-((S)-1-(4-bromo-1-((2-(trimethylsilyl)ethoxy)methyl)-1H-imidazol-2-yl)-6-(2-ethyl-1,3-dioxolan-2-yl)hexyl)-2-methylpropane-2-sulfinamide (A2_C)

A 5 L 3-necked round-bottom flask was purged and maintained with an inert atmosphere of nitrogen. A solution of 2,4-dibromo-1-[[2-(trimethylsilyl)ethoxy]methyl]-1H-imidazole (A2_B, 120 g, 336.96 mmol) in tetrahydrofuran (1200 mL) was added. n-BuLi (138 g, 2.15 mol, 1.02 equiv) was then added dropwise with stirring at −78° C. To this was added (R)-N-[(1E)-6-(2-ethyl-1,3-dioxolan-2-yl)hexylidene]-2-methylpropane-2-sulfinamide (A2_C, 102 g, 336.12 mmol, prepared by the procedures described in Tetrahedron, 2009, 65 (45), 9487-9493) at −78° C. The resulting solution was stirred for 30 min at −30° C. The reaction was then quenched by the addition of 1 L of water. The resulting solution was extracted with 3×1 L of ethyl acetate and the organic layers were combined, washed with 1×500 mL of brine, dried over anhydrous sodium sulfate, and concentrated under vacuum. The crude product was purified by silica gel column. Mobile phase, ACN/water (50% to 70%, with addition of 0.5% NH$_4$HCO$_3$) to give the product. The product was further purified by Chiral SFC (column: CHIRALPAK IA-SFC-0, 25 cm*25 cm, mobile phase, 20% MeOH) to give (R)-N-[(1S)-1-(4-bromo-1-[[2-(trimethylsilyl)ethoxy]methyl]-1H-imidazol-2-yl)-6-(2-ethyl-1,3-dioxolan-2-yl)hexyl]-2-methylpropane-2-sulfinamide (A2_D).

Step 3: Preparation of (S)-9-amino-9-(4-bromo-1-((2-(trimethylsilyl)ethoxy)methyl)-1H-imidazol-2-yl)nonan-3-one (A2_E)

A 3-L 3-necked round-bottom flask was purged and maintained with an inert atmosphere of nitrogen, and solution of (R)-N-[(1S)-1-(4-bromo-1-[[2-(trimethylsilyl)ethoxy]methyl]-1H-imidazol-2-yl)-6-(2-ethyl-1,3-dioxolan-2-yl)hexyl]-2-methylpropane-2-sulfinamide (A2_D, 130 g, 223.87 mmol) in tetrahydrofuran (1300 mL) was added, followed by the addition of hydrogen chloride (24 g, 1.10 equiv) dropwise with stirring at 0-5° C. The resulting solution was stirred at room temperature for 8 h. The resulting solution was diluted with 1000 mL of ice water. The resulting solution was extracted with 3×500 mL of ethyl acetate and the organic layers combined, washed with 1×500 mL of brine, dried over anhydrous sodium sulfate, and concentrated under vacuum. The residue was purified with a silica gel column with DCM/EtOH (30/1) as the mobile phase. The product was diluted with DCM (500 mL) and washed with sat. aqueous Na$_2$CO$_3$ and brine. To the solution was added conc. HCl (16 g/100 mL). The mixture was washed with brine, dried over Na$_2$SO$_4$, and concentrated to afford (9S)-9-amino-9-(4-bromo-1-[[2-(trimethylsilyl)ethoxy]methyl]-1H-imidazol-2-yl)nonan-3-one hydrochloride (A2_E). LCMS (ESI) calc'd for $C_{18}H_{34}BrN_3O_2Si$ [M+H]$^+$: 432.2, found: 434.0. H NMR (300 MHz, DMSO) δ 8.29 (brs, 3H), 7.51 (s, 1H), 5.54 (d, J=11.1 Hz, 1H), 5.23 (d, J=11.2 Hz, 1H), 4.40 (t, J=6.9 Hz, 1H), 3.44 (m, 2H), 2.41-2.26 (m, 4H), 1.84 (brs, 2H), 1.36 (m, 2H), 1.11 (m, 5H), 0.94-0.68 (m, 5H), −0.06 (s, 9H).

Step 4: (S)-tert-butyl 1-(((S)-1-(5-bromo-1-((2-(trimethylsilyl)ethoxy)methyl)-1H-imidazol-2-yl)-7-oxononyl)carbamoyl)-6-azaspiro[2.5]octane-6-carboxylate (A2)

T$_3$P (50% in EtOAc, 14.71 g, 23.12 mmol) was added to a stirred mixture of (S)-9-amino-9-(5-bromo-1-((2-(trimethylsilyl)ethoxy)methyl)-1H-imidazol-2-yl)nonan-3-one (A2_E, 5 g, 11.56 mmol), (S)-6-(tert-butoxycarbonyl)-6-azaspiro[2.5]octane-1-carboxylic acid (A1, 3.54 g, 13.87 mmol) and DIPEA (6 mL, 34.4 mmol) in THF (50 mL) at room temperature. The mixture was stirred at room temperature for 18 h. The reaction was quenched with water (50 mL) and extracted with ethyl acetate (4×50 mL). The combined organic layers were washed with brine (saturated, 2×40 mL), dried over Na$_2$SO$_4$, filtered, and the solvent was evaporated under reduced pressure. The residue was purified by silica gel column flash chromatography, eluting with petroleum ether/EtOAc=1:1 to give (S)-tert-butyl 1-(((S)-1-(5-bromo-1-((2-(trimethylsilyl)ethoxy)methyl)-1H-imidazol-2-yl)-7-oxononyl)carbamoyl)-6-azaspiro[2.5]octane-6-carboxylate (A2). LCMS (ESI) calc'd for $C_{31}H_{53}BrN_4O_5Si$ [M+H]$^+$: 669.3, found: 670.8.

The following intermediate was prepared in a similar manner as intermediate A2 using appropriate starting materials

| Intermediate | Structure | [M + H]+ |
|---|---|---|
| A6 | 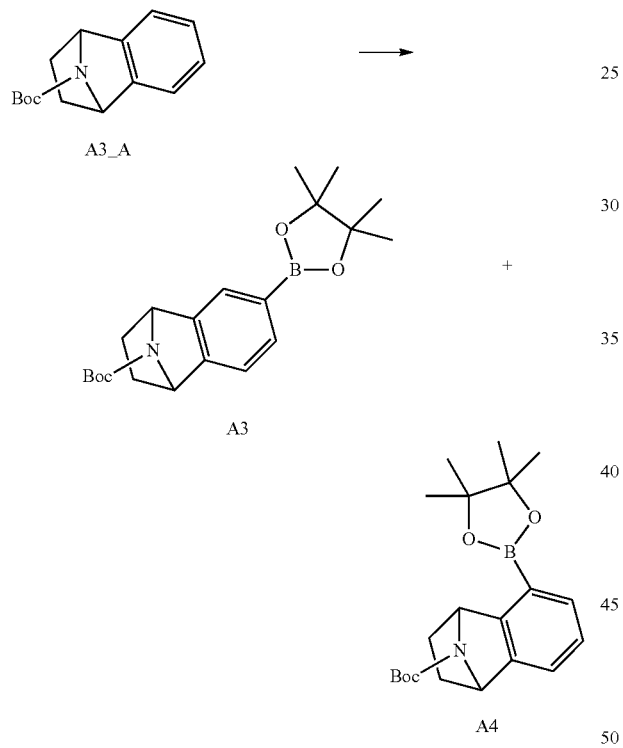 | 540.2 |

Example 3

Preparation of Intermediate A3 and A4

To a degassed solution of tert-butyl 1,2,3,4-tetrahydro-1,4-epiminonaphthalene-9-carboxylate (100 mg, 0.408 mmol), 4,4,4',4',5,5,5',5'-octamethyl-2,2'-bi(1,3,2-dioxaborolane) (A3_A, 311 mg, 1.223 mmol) and (R)-(+)-2,2'-bis[di(3,5-xylyl)phosphino]-6,6'-dimethoxy-1,1'-biphenyl (28.3 mg, 0.041 mmol) in hexane (3.0 mL) was added (1,5-cyclooctadiene)(methoxy)iridium(I) dimer (13.51 mg, 0.020 mmol) under N2. The mixture was stirred at 90° C. for 16 h under N2 and then concentrated. The residue was purified by preparative HPLC (reverse phase C-18 column), eluting with acetonitrile/water+0.225% HCOOH, to give tert-butyl 6-(4,4,5,5-tetramethyl-1,3,2-dioxaborolan-2-yl)-1,2,3,4-tetrahydro-1,4-epiminonaphthalene-9-carboxylate (A3). LCMS (ESI) calc'd for $C_{21}H_{30}BNO_4$ [M+H]+: 372.2, found: 316.1 and tert-butyl 5-(4,4,5,5-tetramethyl-1,3,2-dioxaborolan-2-yl)-1,2,3,4-tetrahydro-1,4-epiminonaphthalene-9-carboxylate (A4). LCMS (ESI) calc'd for $C_{21}H_{30}BNO_4$ [M+H]+: 372.2, found: 272.1.

Example 4

Preparation of Intermediate A5

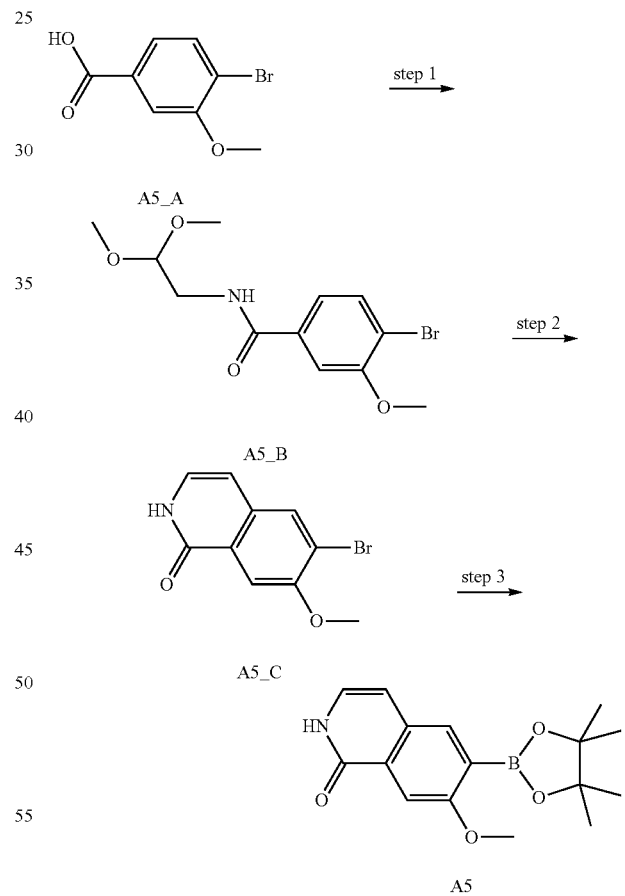

Step 1: Preparation of 4-bromo-N-(2,2-dimethoxyethyl)-3-methoxybenzamide (A5_B)

HATU (3.61 g, 9.5 mmol) and TEA (1.042 g, 10.32 mmol) were added to a stirred mixture of 4-bromo-3-methoxybenzoic acid (2 g, 8.6 mmol) in DCM (20 mL) at room temperature and the mixture was stirred at room temperature for 15 min. Then, 4-bromo-3-methoxyaniline (C18_A, 997 mg, 9.5 mmol) was added. The solution was stirred for 1 h. The solvent was removed to give the title compound (C18_B) which was used to the next step without further purification.

Step 2: Preparation of 6-bromo-7-methoxyisoquinolin-1(2H)-one (A5_C)

H₂SO₄ (20 mL) was added slowly to a stirring round-bottomed flask charged with 4-bromo-N-(2,2-dimethoxy-ethyl)-3-methoxybenzamide (C18_B, 2.72 g crude, 8.6 mmol) at room temperature and the mixture was stirred at room temperature around for 2 h. The reaction was poured into ice water, the resulting precipitate was collected by filtration and the filter cake was washed with water (50 mL) and dried to afford the title compound (C18_C) which was used directly in the next step.

Step 3: Preparation of 7-methoxy-6-(4,4,5,5-tetramethyl-1,3,2-dioxaborolan-2-yl)isoquinolin-1(2H)-one (A5)

PdCl₂(dppf) (112 mg, 0.153 mmol) was added to a stirred mixture of 6-bromo-7-methoxyisoquinolin-1(2H)-one (380 mg, 1.496 mmol), BPD (780 mg, 3.07 mmol) and potassium acetate (632 mg, 6.44 mmol) in 1,4-Dioxane (4 ml) at 29° C. and the mixture was stirred at 90° C. for 3 h under N2 protection. TLC on silica showed starting material was consumed and new product formed. The solvent was evaporated under reduced pressure. The residue was purified by silica gel column flash chromatography, eluting with EtOAc/petroleum ether=0~95% to give 7-methoxy-6-(4,4,5,5-tetramethyl-1,3,2-dioxaborolan-2-yl)isoquinolin-1(2H)-one. LCMS (ESI) calc'd for C16H20BNO4 [M+H]⁺: 302.2, found: 302.1.

Example 5

(3S,6S)-6-(6-oxooctyl)-5,8,18,27,34-pentaazahexa-cyclo[25.2.2.1~7,10~.1~11,15~.1~14,18~.0~1,3~]tetratriaconta-7,9,11(33),12,14,16-hexaene-4,32-dione (1)

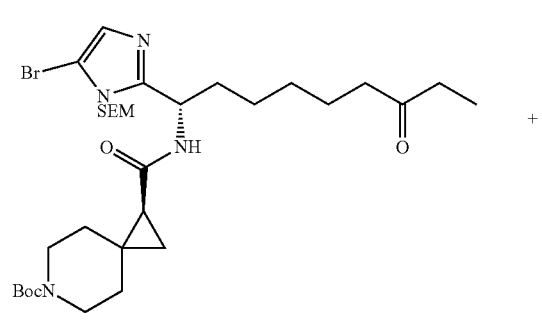

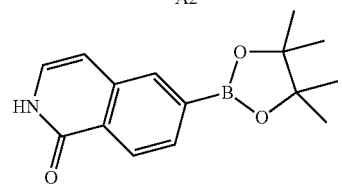

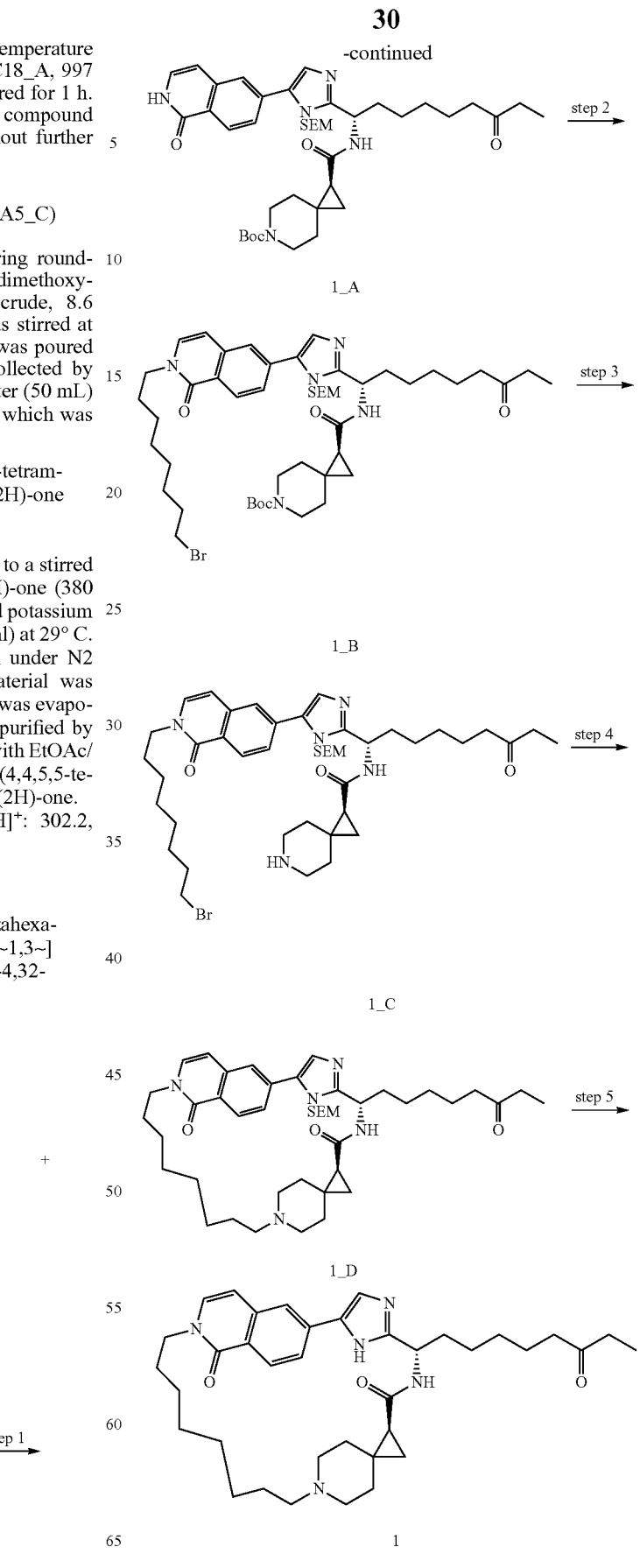

Step 1: (S)-tert-butyl 1-(((S)-7-oxo-1-(5-(1-oxo-1,2-dihydroisoquinolin-6-yl)-1-((2-(trimethylsilyl)ethoxy)methyl)-1H-imidazol-2-yl)nonyl)carbamoyl)-6-azaspiro[2.5]octane-6-carboxylate (1_A)

PdCl$_2$(DTBPF) (19.46 mg, 0.030 mmol) was added to a stirred mixture of 6-(4,4,5,5-tetramethyl-1,3,2-dioxaborolan-2-yl)isoquinolin-1(2H)-one (A5, 121 mg, 0.448 mmol) (S)-tert-butyl 1-(((S)-1-(5-bromo-1-((2-(trimethylsilyl)ethoxy)methyl)-1H-imidazol-2-yl)-7-oxononyl)carbamoyl)-6-azaspiro[2.5]octane-6-carboxylate (A2, 200 mg, 0.299 mmol), K$_3$PO$_4$ (158 mg, 0.747 mmol) in THF (5 mL)/water (1 mL) at room temperature and the mixture was heated with stirring at 75° C. for 3 h. The mixture was cooled and extracted with ethyl acetate (2×30 mL). The combined organic fractions were washed with brine (saturated, 2×30 mL), dried (Na$_2$SO$_4$), filtered and the solvent was evaporated under reduced pressure. The residue was purified by silica gel column flash chromatography, eluting with petroleum ether/EtOAc=1:1 to give (S)-tert-butyl 1-(((S)-7-oxo-1-(5-(1-oxo-1,2-dihydroisoquinolin-6-yl)-1-((2-(trimethylsilyl)ethoxy)methyl)-1H-imidazol-2-yl)nonyl)carbamoyl)-6-azaspiro[2.5]octane-6-carboxylate (1_A). LCMS (ESI) calc'd for C$_{40}$H$_{59}$N$_5$O$_6$Si [M+H]$^+$: 734.4, found: 734.5.

Step 2: (S)-tert-butyl 1-(((S)-1-(5-(2-(8-bromooctyl)-1-oxo-1,2-dihydroisoquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (1_B)

1,8-dibromooctane (82 mg, 0.300 mmol) was added to a stirred mixture of (S)-tert-butyl 1-(((S)-7-oxo-1-(5-(1-oxo-1,2-dihydroisoquinolin-6-yl)-1-((2-(trimethylsilyl)ethoxy)methyl)-1H-imidazol-2-yl)nonyl)carbamoyl)-6-azaspiro[2.5]octane-6-carboxylate (1_A, 200 mg, 0.272 mmol), Cs$_2$CO$_3$ (222 mg, 0.681 mmol) in MeCN (5 mL) at room temperature and the mixture was heated with stirring at 75° C. for 2 h. The mixture was extracted with ethyl acetate (30×2 mL). The combined organic fractions were washed with brine (saturated, 30×2 mL), dried (Na$_2$SO$_4$), filtered and the solvent was evaporated under reduced pressure. The residue was purified by silica gel column flash chromatography, eluting with petroleum ether/EtOAc=1:2 to give (S)-tert-butyl 1-(((S)-1-(5-(2-(8-bromooctyl)-1-oxo-1,2-dihydroisoquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (1_B). LCMS (ESI) calc'd for C$_{48}$H$_{74}$BrN$_5$O$_6$Si [M+H]$^+$: 924.5, found: 926.5

Step 3: (S)-N-((S)-1-(5-(2-(8-bromooctyl)-1-oxo-1,2-dihydroisoquinolin-6-yl)-1-((2-(trimethylsilyl)ethoxy)methyl)-1H-imidazol-2-yl)-7-oxononyl)-6-azaspiro[2.5]octane-1-carboxamide (1_C)

HCl/MeOH (0.1 mL, 0.4 mmol) was added to a stirred mixture of (S)-tert-butyl 1-(((S)-1-(5-(2-(8-bromooctyl)-1-oxo-1,2-dihydroisoquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (1_B, 160 mg, 0.173 mmol) in MeOH (2 mL) at room temperature and the mixture was stirred at room temperature for 4 h. The mixture was filtered and the filter cake was washed with MeOH (3×30 mL). The filtrate was concentrated to dryness to give (S)-N-((S)-1-(5-(2-(8-bromooctyl)-1-oxo-1,2-dihydroisoquinolin-6-yl)-1-((2-(trimethylsilyl)ethoxy)methyl)-1H-imidazol-2-yl)-7-oxononyl)-6-azaspiro[2.5]octane-1-carboxamide (1_C) which was used in the next step without further purification. LCMS (ESI) calc'd for C$_{43}$H$_{66}$BrN$_5$O$_4$Si [M+H]$^+$: 824.4, found: 826.5.

Step 4: (11S,4S)-4-(6-oxooctyl)-5$^1$-((2-(trimethylsilyl)ethoxy)methyl)-6$^1$,6$^2$-dihydro-5$^1$H-3-aza-6(6,2)-isoquinolina-1$^5$(4,1)-piperidina-5(2,5)-imidazola-1(1,2)-cyclopropanapentadecaphane-6$^1$,2-dione (1_D)

NaI (21.80 mg, 0.145 mmol) was added to a stirred mixture of (S)-N-((S)-1-(5-(2-(8-bromooctyl)-1-oxo-1,2-dihydroisoquinolin-6-yl)-1-((2-(trimethylsilyl)ethoxy)methyl)-1H-imidazol-2-yl)-7-oxononyl)-6-azaspiro[2.5]octane-1-carboxamide (1_C, 120 mg, 0.145 mmol) and DIEA (0.1 mL, 0.573 mmol) in acetonitrile (2 mL) at room temperature and the mixture was stirred at 90° C. for 12 h. The mixture was concentrated. The residue was purified by silica gel column flash chromatography eluting with DCM/MeOH= 10:1 to give compound 1_D. LCMS (ESI) calc'd for C$_{43}$H$_{65}$N$_5$O$_4$Si [M+H]+: 744.5, found: 744.5.

Step 5: (11S,4S)-4-(6-oxooctyl)-6$^1$,6$^2$-dihydro-5$^1$H-3-aza-6(6,2)-isoquinolina-1$^5$(4,1)-piperidina-5(2,5)-imidazola-1(1,2)-cyclopropanapentadecaphane-6$^1$,2-dione (1)

TFA (1 mL, 12.98 mmol) was added to a stirred mixture of 1_D (40 mg, 0.054 mmol) in DCM (2 mL) at room temperature and the mixture was stirred at room temperature for 18 h. The mixture was concentrated and the residue was purified by preparative HPLC (reverse phase C-18 column) eluting with acetonitrile/water+0.1% TFA, to give compound 1. LCMS (ESI) calc'd for C$_{37}$H$_{51}$N$_5$O$_3$ [M+H]+: 614.4, found: 614.4. $^1$H NMR (400 MHz, MeOD) δ 8.37 (d, J=8.41 Hz, 1H), 8.17 (brs, 1H), 7.81-7.87 (m, 2H), 7.49 (d, J=7.43 Hz, 1H), 6.71 (d, J=7.24 Hz, 1H), 5.00 (t, J=7.82 Hz, 1H), 3.40 (d, J=11.74 Hz, 1H), 3.09 (t, J=11.25 Hz, 1H), 2.85 (d, J=11.35 Hz, 1H), 2.37-2.53 (m, 5H), 2.05-2.22 (m, 4H), 1.71-1.91 (m, 6H), 1.50-1.64 (m, 4H), 1.14-1.42 (m, 10H), 0.95-1.04 (m, 5H), 0.89 (d, J=4.89 Hz, 2H), 0.44-0.65 (m, 2H).

Example 6

(11S,4S)-4-(6-oxooctyl)-6$^1$,6$^2$,6$^3$,6$^4$-tetrahydro-5$^1$H-3-aza-6(5,9)-1,4-epiminonaphthalena-1$^1$(4,1)-piperidina-5(2,5)-imidazola-1(1,2)-cyclopropanaundecaphan-2-one (2)

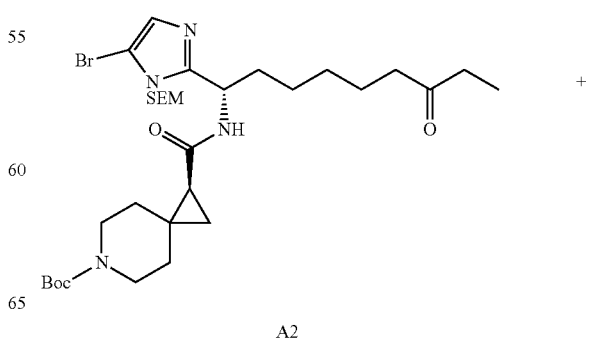

A2

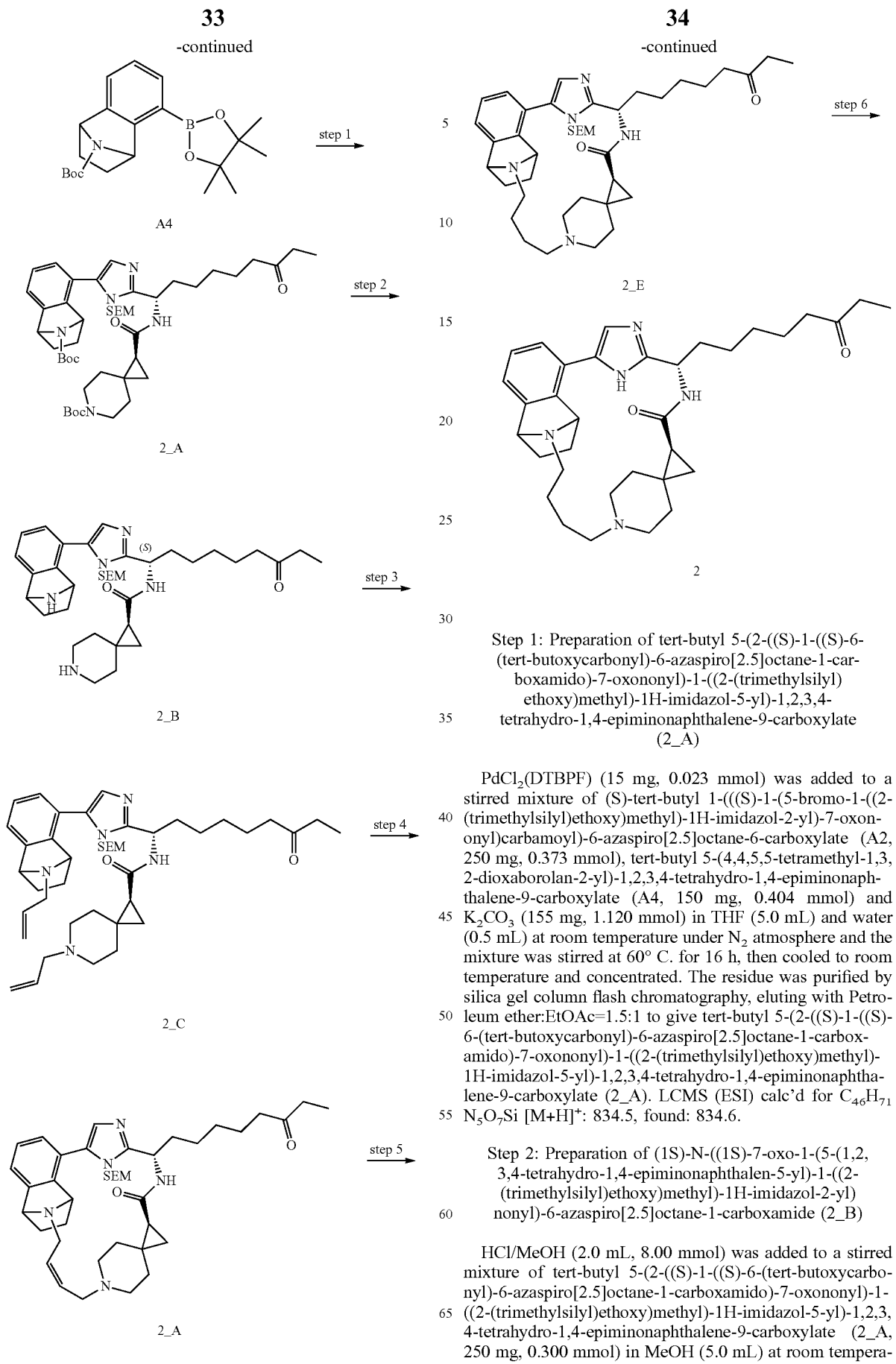

Step 1: Preparation of tert-butyl 5-(2-((S)-1-((S)-6-(tert-butoxycarbonyl)-6-azaspiro[2.5]octane-1-carboxamido)-7-oxononyl)-1-((2-(trimethylsilyl)ethoxy)methyl)-1H-imidazol-5-yl)-1,2,3,4-tetrahydro-1,4-epiminonaphthalene-9-carboxylate (2_A)

PdCl$_2$(DTBPF) (15 mg, 0.023 mmol) was added to a stirred mixture of (S)-tert-butyl 1-(((S)-1-(5-bromo-1-((2-(trimethylsilyl)ethoxy)methyl)-1H-imidazol-2-yl)-7-oxononyl)carbamoyl)-6-azaspiro[2.5]octane-6-carboxylate (A2, 250 mg, 0.373 mmol), tert-butyl 5-(4,4,5,5-tetramethyl-1,3,2-dioxaborolan-2-yl)-1,2,3,4-tetrahydro-1,4-epiminonaphthalene-9-carboxylate (A4, 150 mg, 0.404 mmol) and K$_2$CO$_3$ (155 mg, 1.120 mmol) in THF (5.0 mL) and water (0.5 mL) at room temperature under N$_2$ atmosphere and the mixture was stirred at 60° C. for 16 h, then cooled to room temperature and concentrated. The residue was purified by silica gel column flash chromatography, eluting with Petroleum ether:EtOAc=1.5:1 to give tert-butyl 5-(2-((S)-1-((S)-6-(tert-butoxycarbonyl)-6-azaspiro[2.5]octane-1-carboxamido)-7-oxononyl)-1-((2-(trimethylsilyl)ethoxy)methyl)-1H-imidazol-5-yl)-1,2,3,4-tetrahydro-1,4-epiminonaphthalene-9-carboxylate (2_A). LCMS (ESI) calc'd for C$_{46}$H$_{71}$N$_5$O$_7$Si [M+H]$^+$: 834.5, found: 834.6.

Step 2: Preparation of (1S)-N-((1S)-7-oxo-1-(5-(1,2,3,4-tetrahydro-1,4-epiminonaphthalen-5-yl)-1-((2-(trimethylsilyl)ethoxy)methyl)-1H-imidazol-2-yl)nonyl)-6-azaspiro[2.5]octane-1-carboxamide (2_B)

HCl/MeOH (2.0 mL, 8.00 mmol) was added to a stirred mixture of tert-butyl 5-(2-((S)-1-((S)-6-(tert-butoxycarbonyl)-6-azaspiro[2.5]octane-1-carboxamido)-7-oxononyl)-1-((2-(trimethylsilyl)ethoxy)methyl)-1H-imidazol-5-yl)-1,2,3,4-tetrahydro-1,4-epiminonaphthalene-9-carboxylate (2_A, 250 mg, 0.300 mmol) in MeOH (5.0 mL) at room temperature and the mixture was stirred at rt for 4 h, then adjusted to pH 8 with NaHCO₃ solution, extracted with EtOAc (10 mL*2), washed with brine (10 mL), dried over Na₂SO₄, filtered and concentrated to afford (1S)-N-((1S)-7-oxo-1-(5-(1,2,3,4-tetrahydro-1,4-epiminonaphthalen-5-yl)-1-((2-(trimethylsilyl)ethoxy)methyl)-1H-imidazol-2-yl)nonyl)-6-azaspiro[2.5]octane-1-carboxamide (2_B) without further purification. LCMS (ESI) calc'd for $C_{36}H_{55}N_5O_3Si$ [M+H]⁺: 634.4, found: 634.4.

Step 3: Preparation of (1S)-6-allyl-N-((1S)-1-(5-(9-allyl-1,2,3,4-tetrahydro-1,4-epiminonaphthalen-5-yl)-1-((2-(trimethylsilyl)ethoxy)methyl)-1H-imidazol-2-yl)-7-oxononyl)-6-azaspiro[2.5]octane-1-carboxamide (2_C)

3-bromoprop-1-ene (67 mg, 0.554 mmol) was added to a stirred mixture of (1S)-N-((1S)-7-oxo-1-(5-(1,2,3,4-tetrahydro-1,4-epiminonaphthalen-5-yl)-1-((2-(trimethylsilyl)ethoxy)methyl)-1H-imidazol-2-yl)nonyl)-6-azaspiro[2.5]octane-1-carboxamide (2_B, 170 mg, 0.268 mmol) and DIPEA (0.141 mL, 0.804 mmol) in MeCN (3.0 mL) at room temperature and the mixture was stirred at rt for 4 h. The mixture was diluted with ethyl acetate (10 mL), washed with brine (saturated, 5 mL), dried (Na₂SO₄), filtered and the solvent was evaporated under reduced pressure. The residue was purified by preparative TLC on silica gel, eluting with DCM:MeOH=10:1 to give (1S)-6-allyl-N-((1S)-1-(5-(9-allyl-1,2,3,4-tetrahydro-1,4-epiminonaphthalen-5-yl)-1-((2-(trimethylsilyl)ethoxy)methyl)-1H-imidazol-2-yl)-7-oxononyl)-6-azaspiro[2.5]octane-1-carboxamide (2_C). LCMS (ESI) calc'd for $C_{42}H_{63}N_5O_3Si$ [M+H]⁺: 714.5, found: 714.5.

Step 4: Preparation of (1¹S,4S,Z)-4-(6-oxooctyl)-5¹-((2-(trimethylsilyl)ethoxy)methyl)-6¹,6²,6³,6⁴-tetrahydro-5¹H-3-aza-6(5,9)-1,4-epiminonaphthalena-11(4,1)-piperidina-5(2,5)-imidazola-1(1,2)-cyclopropanaundecaphan-8-en-2-one (2_D)

Grubbs II (10 mg, 0.012 mmol) was added to a stirred mixture of (1S)-6-allyl-N-((1S)-1-(5-(9-allyl-1,2,3,4-tetrahydro-1,4-epiminonaphthalen-5-yl)-1-((2-(trimethylsilyl)ethoxy)methyl)-1H-imidazol-2-yl)-7-oxononyl)-6-azaspiro[2.5]octane-1-carboxamide (2_C, 50 mg, 0.07 mmol) in DCM (5.0 mL) under N2 atmosphere at room temperature and the mixture was stirred at 50° C. for 18 h, then concentrated. The residue was purified by preparative silica gel TLC, eluting with DCM/MeOH=10:1 to give the title compound (2_D). LCMS (ESI) calc'd for $C_{40}H_{59}N_5O_3Si$ [M+H]⁺: 686.4, found: 686.4.

Step 5: Preparation of (1¹S,4S)-4-(6-oxooctyl)-6¹,6²,6³,6⁴-tetrahydro-5¹H-3-aza-6(5,9)-1,4-epiminonaphthalena-11(4,1)-piperidina-5(2,5)-imidazola-1(1,2)-cyclopropanaundecaphan-2-one (2_E)

A solution of 2_D (20 mg, 0.029 mmol) in MeOH (5.0 mL) was added to a 50 mL round-bottom flask and then Pd—C (20 mg, 0.019 mmol) (10%, wet) was added under Ar. The suspension was degassed under vacuum and purged with N2 several times. The mixture was stirred under H₂ (pressure: 15 psi) at rt for 4 h and filtered, the filtrate was concentrated to afford the title compound (2_E) without further purification. LCMS (ESI) calc'd for $C_{40}H_{61}N_5O_3Si$ [M+H]⁺: 688.5, found: 688.5.

Step 6: Preparation of (1¹S,4S)-4-(6-oxooctyl)-6¹,6²,6³,6⁴-tetrahydro-5¹H-3-aza-6(5,9)-1,4-epiminonaphthalena-11(4,1)-piperidina-5(2,5)-imidazola-1(1,2)-cyclopropanaundecaphan-2-one (2)

TFA (0.5 mL, 6.49 mmol) was added to a stirred mixture of 2_E (20 mg, 0.029 mmol) in DCM (0.2 mL) at room temperature and the mixture was stirred at room temperature for 4 h and concentrated. The residue was purified by preparative HPLC (reverse phase C-18 column), eluting with acetonitrile/water+0.1% TFA, to give a crude 2, which was further separated by preparative TLC (DCM:MeOH=10:1) to afford 2. LCMS (ESI) calc'd for $C_{34}H_{47}N_5O_2$ [M+H]⁺: 558.4, found: 558.2.

Example 7

(1¹S,4S,E)-4-(6-oxooctyl)-6¹,6²,6³,6⁴-tetrahydro-5¹H-3-aza-6(6,9)-1,4-epiminonaphthalena-11(4,1)-piperidina-5(2,5)-imidazola-1(1,2)-cyclopropanaundecaphan-8-en-2-one (3)

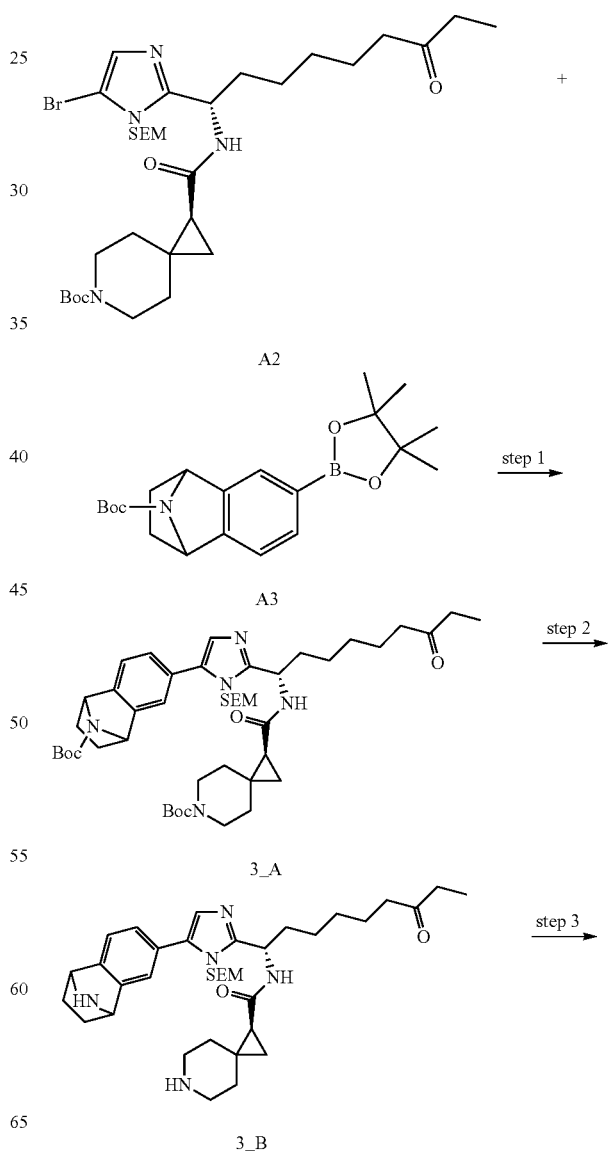

-continued

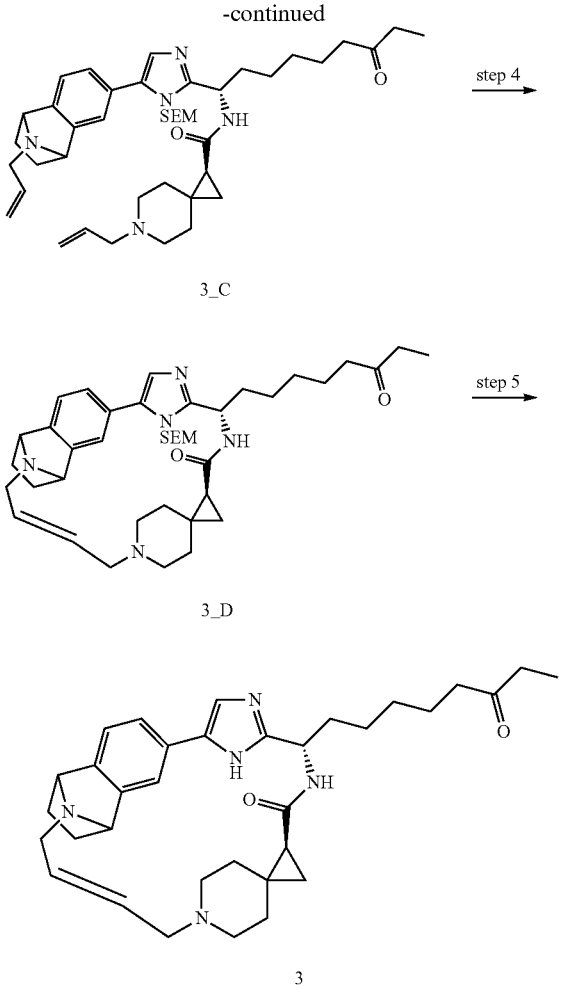

Step 1: Preparation of tert-butyl 6-(2-((S)-1-((S)-6-(tert-butoxycarbonyl)-6-azaspiro[2.5]octane-1-carboxamido)-7-oxononyl)-1-((2-(trimethylsilyl)ethoxy)methyl)-1H-imidazol-5-yl)-1,2,3,4-tetrahydro-1,4-epiminonaphthalene-9-carboxylate (3_A)

PdCl$_2$(DTBPF) (36.0 mg, 0.055 mmol) was added to a stirred mixture of (S)-tert-butyl 1-(((S)-1-(5-bromo-1-((2-(trimethylsilyl)ethoxy)methyl)-1H-imidazol-2-yl)-7-oxononyl)carbamoyl)-6-azaspiro[2.5]octane-6-carboxylate (A2, 370 mg, 0.552 mmol), tert-butyl 6-(4,4,5,5-tetramethyl-1,3,2-dioxaborolan-2-yl)-1,2,3,4-tetrahydro-1,4-epiminonaphthalene-9-carboxylate (A3, 220 mg, 0.593 mmol) and K$_2$CO$_3$ (229 mg, 1.657 mmol) in THF (5.0 mL) and water (0.5 mL) at room temperature under N$_2$ atmosphere and the mixture was stirred at 65° C. for 16 h, then cooled to room temperature and concentrated. The residue was purified by silica gel column flash chromatography, eluting with Petroleum ether:EtOAc=1.5:1 to give tert-butyl 6-(2-((S)-1-((S)-6-(tert-butoxycarbonyl)-6-azaspiro[2.5]octane-1-carboxamido)-7-oxononyl)-1-((2-(trimethylsilyl)ethoxy)methyl)-1H-imidazol-5-yl)-1,2,3,4-tetrahydro-1,4-epiminonaphthalene-9-carboxylate (3_A). LCMS (ESI) calc'd for C$_{46}$H$_{71}$N$_5$O$_7$Si [M+H]$^+$: 834.5, found: 834.7.

Step 2: Preparation of (1S)-N-((1S)-7-oxo-1-(5-(1,2,3,4-tetrahydro-1,4-epiminonaphthalen-6-yl)-1-((2-(trimethylsilyl)ethoxy)methyl)-1H-imidazol-2-yl)nonyl)-6-azaspiro[2.5]octane-1-carboxamide (3_B)

HCl/MeOH (2.0 mL, 8.00 mmol) was added to a stirred mixture of tert-butyl 6-(2-((S)-1-((S)-6-(tert-butoxycarbonyl)-6-azaspiro[2.5]octane-1-carboxamido)-7-oxononyl)-1-((2-(trimethylsilyl)ethoxy)methyl)-1H-imidazol-5-yl)-1,2,3,4-tetrahydro-1,4-epiminonaphthalene-9-carboxylate (3_A, 380 mg, 0.456 mmol) in MeOH (5.0 mL) at room temperature and the mixture was stirred at rt for 1 h. The mixture was concentrated at room temperature, adjusted to pH 9 with NaHCO$_3$ solution, and the mixture was extracted with ethyl acetate (2×20 mL). The combined organic fractions were washed with brine (saturated, 10 mL), dried (Na$_2$SO$_4$), filtered and the solvent was evaporated under reduced pressure to give (1S)-N-((1S)-7-oxo-1-(5-(1,2,3,4-tetrahydro-1,4-epiminonaphthalen-6-yl)-1-((2-(trimethylsilyl)ethoxy)methyl)-1H-imidazol-2-yl)nonyl)-6-azaspiro[2.5]octane-1-carboxamide (3_B) without further purification. LCMS (ESI) calc'd for C$_{36}$H$_{55}$N$_5$O$_3$Si [M+H]+: 634.4, found: 634.5.

Step 3: Preparation of (1S)-6-allyl-N-((1S)-1-(5-(9-allyl-1,2,3,4-tetrahydro-1,4-epiminonaphthalen-6-yl)-1-((2-(trimethylsilyl)ethoxy)methyl)-1H-imidazol-2-yl)-7-oxononyl)-6-azaspiro[2.5]octane-1-carboxamide (3_C)

DIEA (0.207 ml, 1.183 mmol) was added to a stirred mixture of (1S)-N-((1S)-7-oxo-1-(5-(1,2,3,4-tetrahydro-1,4-epiminonaphthalen-6-yl)-1-((2-(trimethylsilyl)ethoxy)methyl)-1H-imidazol-2-yl)nonyl)-6-azaspiro[2.5]octane-1-carboxamide (3_B, 250 mg, 0.394 mmol) and 3-bromoprop-1-ene (95 mg, 0.789 mmol) in acetonitrile (10 mL) at room temperature and the mixture was stirred at rt for 2 h, then water (10 mL) was added and the mixture was extracted with ethyl acetate (20 mL). The combined organic fractions were washed with brine (saturated, 10 mL), dried (Na$_2$SO$_4$), filtered and the solvent was evaporated under reduced pressure. The residue was purified by preparative TLC on silica gel, eluting with DCM/MeOH=10:1 to give (1S)-6-allyl-N-((1S)-1-(5-(9-allyl-1,2,3,4-tetrahydro-1,4-epiminonaphthalen-6-yl)-1-((2-(trimethylsilyl)ethoxy)methyl)-1H-imidazol-2-yl)-7-oxononyl)-6-azaspiro[2.5]octane-1-carboxamide (3_C). LCMS (ESI) calc'd for C$_{42}$H$_{63}$N$_5$O$_3$Si [M+H]$^+$: 714.5, found: 714.5.

Step 4: Preparation of (1'S,4S,E)-4-(6-oxooctyl)-5¹-((2-(trimethylsilyl)ethoxy)methyl)-6¹,6²,6³,6⁴-tetrahydro-5¹H-3-aza-6(6,9)-1,4-epiminonaphthalena-11(4,1)-piperidina-5(2,5)-imidazola-1(1,2)-cyclopropanaundecaphan-8-en-2-one 3_D Grubbs II (15 mg, 0.018 mmol) was added to a stirred mixture of (1S)-6-allyl-N-((1S)-1-(5-(9-allyl-1,2,3,4-tetrahydro-1,4-epiminonaphthalen-6-yl)-1-((2-(trimethylsilyl)ethoxy)methyl)-1H-imidazol-2-yl)-7-oxononyl)-6-azaspiro[2.5]octane-1-carboxamide (3_C, 50 mg, 0.070 mmol) in ClCH$_2$CH$_2$Cl (25 mL) under N2 atmosphere at room temperature and the mixture was stirred at 50° C. for 18 h. Grubbs II (15 mg, 0.018 mmol) was again added and the mixture was stirred at 85° C. for another 18 h, then concentrated. The residue was purified by preparative TLC on silica gel, eluting with DCM/MeOH=10:1 to give the title compound (3_D). LCMS (ESI) calc'd for $C_{40}H_{59}N_5O_3Si$ [M+H]+: 686.4, found: 686.5.

Step 2: Preparation of (1'S,4S,E)-4-(6-oxooctyl)-$6^1$,$6^2$,$6^3$,$6^4$-tetrahydro-$5^1$H-3-aza-6(6,9)-1,4-epiminonaphthalena-11(4,1)-piperidina-5(2,5)-imidazola-1(1,2)-cyclopropanaundecaphan-8-en-2-one 3

TFA (0.5 mL, 6.49 mmol) was added to a stirred mixture of 3_D (8 mg, 0.012 mmol) in DCM (0.2 mL) at room temperature and the mixture was stirred at rt for 3 h, then left to stand overnight and concentrated. The residue was purified by preparative TLC on silica gel, eluting with DCM/MeOH=10:1 to give compound 3. LCMS (ESI) calc'd for $C_{34}H_{45}N_5O_2$ [M+H]+: 556.4, found: 556.4. $^1$H NMR (400 MHz, MeOD) δ 8.10 (s, 1H), 7.60 (d, J=6.8 Hz, 1H), 7.39-7.42 (m, 2), 5.95-6.05 (m, 1H), 5.75-5.85 (m, 1H), 4.95-5.01 (m, 1H), 4.50-4.72 (m, 4H), 3.72-3.75 (m, 1H), 2.95-3.25 (m, 3H), 2.75 (brs, 1H), 2.10-2.46 (m, 12H), 1.75-1.90 (m, 4H), 1.50-1.60 (m, 5H), 1.20-1.30 (m, 1H), 0.95-1.05 (m, 4H), 0.75-0.85 (m, 2H).

Example 8

($1^1$S,4S)-4-(6-oxooctyl)-$6^1$,$6^2$-dihydro-$5^1$H-9-oxa-3-aza-6(6,2)-isoquinolina-12(4,1)-piperidina-5(2,5)-imidazola-1(1,2)-cyclopropanadodecaphane-$6^1$,2-dione (4)

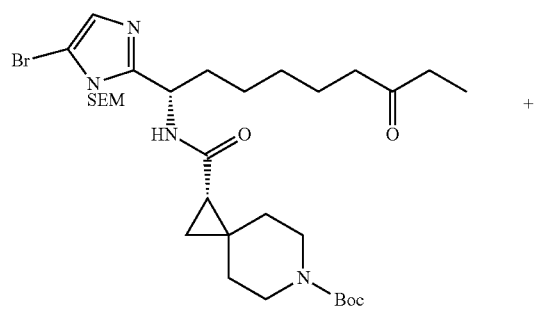

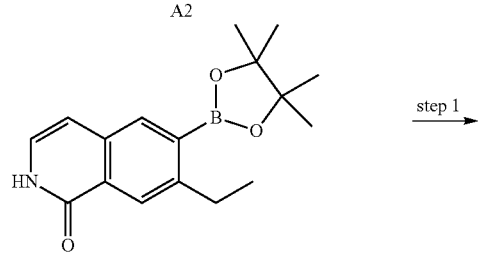

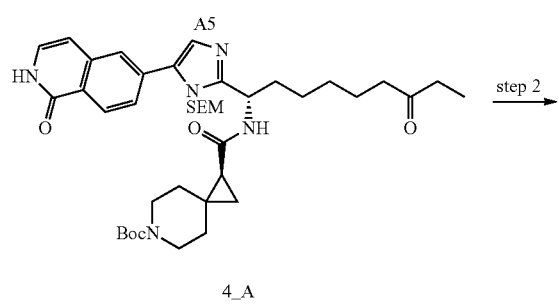

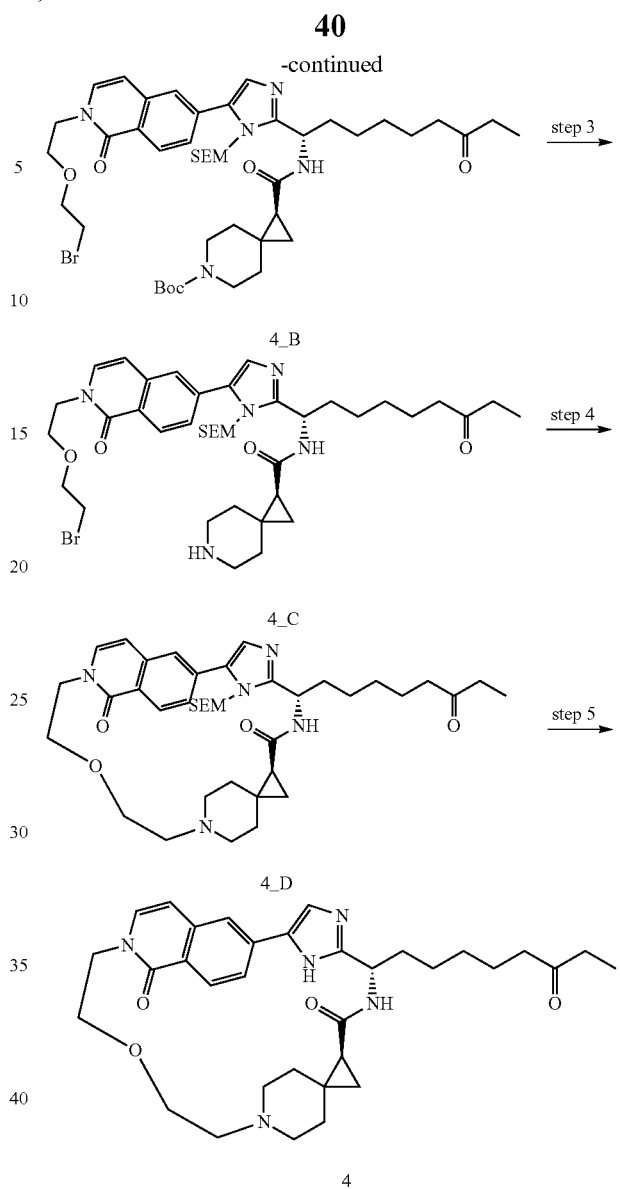

Step 1: (S)-tert-butyl 1-(((S)-1-(5-(7-methoxy-1-oxo-1,2-dihydroisoquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (4_A)

PdCl$_2$(DTBPF) (25 mg, 0.038 mmol) was added to a mixture of (S)-tert-butyl 1-(((S)-1-(5-bromo-1-((2-(trimethylsilyl)ethoxy)methyl)-1H-imidazol-2-yl)-7-oxononyl)carbamoyl)-6-azaspiro[2.5]octane-6-carboxylate (A2, 129 mg, 0.193 mmol), 7-methoxy-6-(4,4,5,5-tetramethyl-1,3,2-dioxaborolan-2-yl)isoquinolin-1(2H)-one (A5, 120 mg, 0.239 mmol) and K$_3$PO$_4$ (150 mg, 0.707 mmol) in co-solvents of THF (2 mL) and water (0.2 mL) at 27° C. and the mixture was stirred at 80° C. for 3 h. The mixture was cooled, diluted with water (15 mL), and extracted with DCM (3×10 mL). The combined organic fractions were washed with brine (saturated, 10 mL), dried (Na$_2$SO$_4$), filtered and the solvent was evaporated under reduced pressure. The residue was purified by silica gel column flash chromatography, eluting with petroleum EtOAc/ether=0~42%~90% to give (S)-tertbutyl 1-(((S)-1-(5-(7-methoxy-1-oxo-1,2-dihydroisoquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (4_A). LCMS (ESI) calc'd for $C_{41}H_{61}N_5O_7Si$ [M+H]+: 764.4, found: 764.4.

Step 2: Preparation of (S)-tert-butyl 1-(((S)-1-(5-(2-(2-(2-bromoethoxy)ethyl)-1-oxo-1,2-dihydroisoquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (4_B)

1-bromo-2-(2-bromoethoxy)ethane (506 mg, 2.180 mmol) was added to a stirred mixture of $Cs_2CO_3$ (1420 mg, 4.36 mmol), and (S)-tert-butyl 1-(((S)-7-oxo-1-(5-(1-oxo-1,2-dihydroisoquinolin-6-yl)-1-((2-(trimethylsilyl)ethoxy)methyl)-1H-imidazol-2-yl)nonyl)carbamoyl)-6-azaspiro[2.5]octane-6-carboxylate (4_A, 800 mg, 1.090 mmol) in MeCN (6 mL) at room temperature and the mixture was stirred at 70° C. for 3 h. The mixture was cooled, diluted with ethyl acetate (10 mL), washed with brine (saturated, 3×10 mL), dried ($Na_2SO_4$), filtered and the solvent was evaporated under reduced pressure. The residue was purified by silica gel column flash chromatography, eluting with EtOAc/petroleum ether=30-100% to give (S)-tert-butyl 1-(((S)-1-(5-(2-(2-(2-bromoethoxy)ethyl)-1-oxo-1,2-dihydroisoquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (4_B). LCMS (ESI) calc'd for $C_{44}H_{66}BrN_5O_7Si$ [M+H]+: 884.4, found: 886.4.

Step 3: Preparation of (S)-N-((S)-1-(5-(2-(2-(2-bromoethoxy)ethyl)-1-oxo-1,2-dihydroisoquinolin-6-yl)-1-((2-(trimethylsilyl)ethoxy)methyl)-1H-imidazol-2-yl)-7-oxononyl)-6-azaspiro[2.5]octane-1-carboxamide (4_C)

HCl/MeOH (1.5 mL, 6.00 mmol) was added to a stirred mixture of (S)-tert-butyl 1-(((S)-1-(5-(2-(2-(2-bromoethoxy)ethyl)-1-oxo-1,2-dihydroisoquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (4_B, 530 mg, 0.599 mmol) in DCM (7 mL) at room temperature and the mixture was stirred at room temperature for 2 h. Aqueous sodium hydrogen carbonate (saturated, 5 mL) was added and the mixture was extracted with dichloromethane (3×10 mL). The combined organic fractions were washed with brine (saturated, 1×15 mL), dried ($Na_2SO_4$), filtered and the solvent was evaporated under reduced pressure. The residue was concentrated to give (S)-N-((S)-1-(5-(2-(2-(2-bromoethoxy)ethyl)-1-oxo-1,2-dihydroisoquinolin-6-yl)-1-((2-(trimethylsilyl)ethoxy)methyl)-1H-imidazol-2-yl)-7-oxononyl)-6-azaspiro[2.5]octane-1-carboxamide (4_C) which was used to the next step without further purification. LCMS (ESI) calc'd for $C_{39}H_{58}BrN_5O_5Si$ [M+H]+: 784.3, found: 786.4.

Step 4: Preparation of (1'S,4S)-4-(6-oxooctyl)-5¹-((2-(trimethylsilyl)ethoxy)methyl)-6¹,6²-dihydro-5¹H-9-oxa-3-aza-6(6,2)-isoquinolina-12(4,1)-piperidina-5(2,5)-imidazola-1(1,2)-cyclopropanadodecaphane-61,2-dione (4_D)

Sodium iodide (90 mg, 0.599 mmol) was added to a stirred mixture of DIEA (0.4 mL, 2.290 mmol), and (S)-N-((S)-1-(5-(2-(2-(2-bromoethoxy)ethyl)-1-oxo-1,2-dihydroisoquinolin-6-yl)-1-((2-(trimethylsilyl)ethoxy)methyl)-1H-imidazol-2-yl)-7-oxononyl)-6-azaspiro[2.5]octane-1-carboxamide (4_C, 470 mg, 0.599 mmol) in MeCN (40 mL) at room temperature and the mixture was stirred at 70° C. for 12 h. The mixture was cooled, MeCN was removed, it was diluted with dichloromethane (10 mL), washed with brine (saturated, 3×10 mL), dried ($Na_2SO_4$), filtered and the solvent was evaporated under reduced pressure. The residue was concentrated to give compound 4_D which was used to the next step without further purification. LCMS (ESI) calc'd for $C_{39}H_{57}N_5O_5Si$ [M+H]+: 704.4, found: 704.9.

Step 5: Preparation of (1¹S,4S)-4-(6-oxooctyl)-6¹,6²-dihydro-5¹H-9-oxa-3-aza-6(6,2)-isoquinolina-12(4,1)-piperidina-5(2,5)-imidazola-1(1,2)-cyclopropanadodecaphane-6¹,2-dione (4)

Compound 4_D (360 mg, 0.511 mmol) was dissolved in TFA (2 mL, 26.0 mmol) at room temperature and the mixture was stirred at rt for 2 h. Aqueous sodium hydroxide (saturated, 5 mL) was added and the mixture was extracted with dichloromethane (3×5 mL). The combined organic fractions were washed with brine (saturated, 1×10 mL), dried ($Na_2SO_4$), filtered and the solvent was evaporated under reduced pressure. The residue was purified by preparative HPLC, eluting with acetonitrile/water+0.05% $NH_4OH$, to give compound 4.

L-(+)-tartaric acid (16 mg, 0.107 mmol) in water (2 mL) was added to a stirred mixture of compound 4 (60 mg, 0.105 mmol) in MeCN (2 mL) at room temperature and the mixture was lyophilizated to give the tartarate salt of 4. LCMS (ESI) calc'd for $C_{33}H_{43}N_5O_4$ [M+H]+: 574.3, found: 574.4. ¹H NMR (400 MHz, MeOD) δ 8.09 (brs, 1H), 7.66 (s, 3H), 7.09 (brs, 1H), 6.41 (d, J=7.0 Hz, 1H), 5.08 (brs, 1H), 4.49 (s, 2H), 4.07-4.37 (m, 1H), 3.96 (brs, 1H), 3.73 (brs, 2H), 3.58 (brs, 1H), 3.37 (brs, 1H), 3.17 (brs, 1H), 2.41-2.50 (m, 4H), 2.30 (m, 1H), 1.91-2.09 (m, 3H), 1.80-1.90 (m, 2H), 1.79 (brs, 1H), 1.43-1.60 (m, 3H), 1.21-1.39 (m, 5H), 1.19 (brs, 1H), 0.98 (t, J=7.4 Hz, 4H).

Example 9

(1¹S,4S)-6⁷-methoxy-4-(6-oxooctyl)-6¹,6²-dihydro-5¹H-3-aza-6(6,2)-isoquinolina-15(4,1)-piperidina-5(2,5)-imidazola-1(1,2)-cyclopropanapentadecaphane-6¹,2-dione (5)

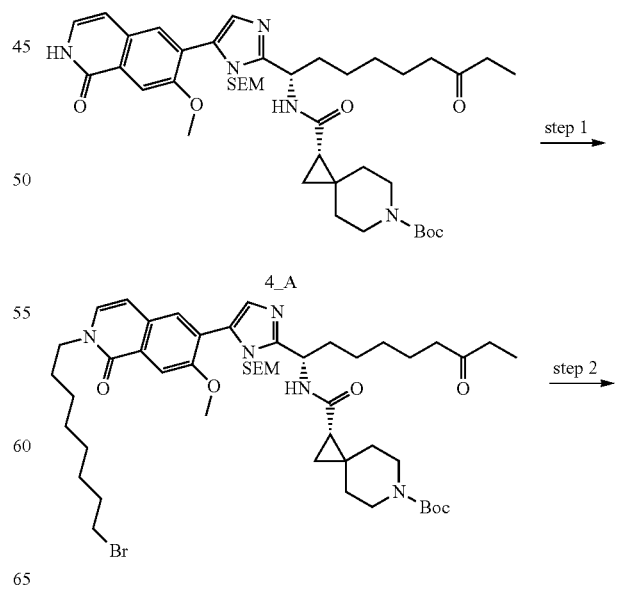

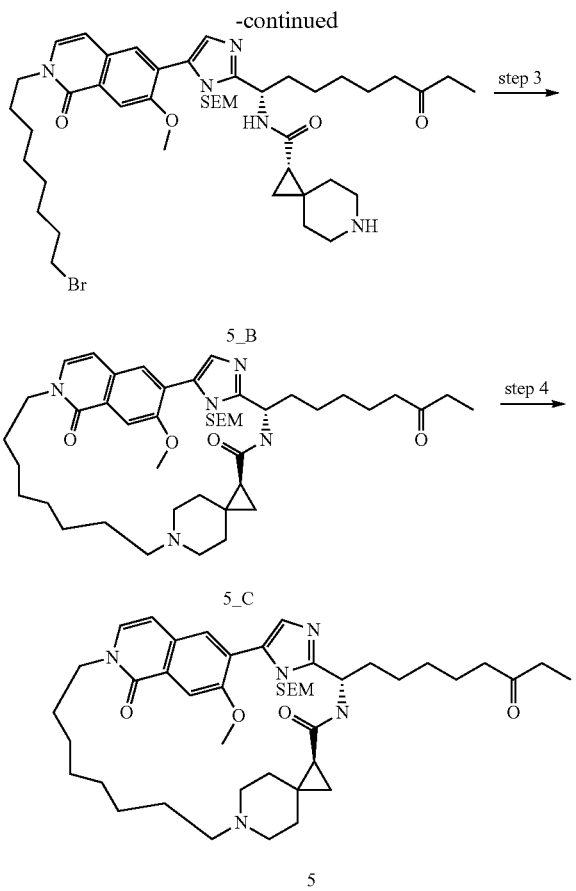

Step 1: (S)-tert-butyl 1-(((S)-1-(5-(2-(8-bromooctyl)-7-methoxy-1-oxo-1,2-dihydroisoquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (5_A)

1,8-dibromooctane (116 mg, 0.426 mmol) was added to a mixture of (S)-tert-butyl 1-(((S)-1-(5-(7-methoxy-1-oxo-1,2-dihydroisoquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (4_A, 100 mg, 0.131 mmol) and $Cs_2CO_3$ (225 mg, 0.691 mmol) in acetonitrile (3 mL) at 28° C. and the mixture was stirred at 70° C. for 4 h. The mixture was concentrated in vacuo. The residue was purified by silica gel column flash chromatography, eluting with EtOAc/petroleum ether=0~47% to give (S)-tert-butyl 1-(((S)-1-(5-(2-(8-bromooctyl)-7-methoxy-1-oxo-1,2-dihydroisoquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (5_A). LCMS (ESI) calc'd for $C_{49}H_{76}BrN_5O_7Si$ [M+H]$^+$: 954.5, found: 954.4.

Step 2: (S)-N-((S)-1-(5-(2-(8-bromooctyl)-7-methoxy-1-oxo-1,2-dihydroisoquinolin-6-yl)-1-((2-(trimethylsilyl)ethoxy)methyl)-1H-imidazol-2-yl)-7-oxononyl)-6-azaspiro[2.5]octane-1-carboxamide (5_B)

HCl/MeOH (3 mL, 12.00 mmol) was added to a stirred mixture of (S)-tert-butyl 1-(((S)-1-(5-(2-(8-bromooctyl)-7-methoxy-1-oxo-1,2-dihydroisoquinolin-6-yl)-1-((2-(trim-ethylsilyl)ethoxy)methyl)-1H-imidazol-2-yl)-7-oxononyl)carbamoyl)-6-azaspiro[2.5]octane-6-carboxylate (5_A, 80 mg, 0.084 mmol) in DCM (6 mL) at 27° C. and the mixture was stirred at 27° C. for 1 h. The solvent was evaporated under reduced pressure to give (S)-N-((S)-1-(5-(2-(8-bromooctyl)-7-methoxy-1-oxo-1,2-dihydroisoquinolin-6-yl)-1-((2-(trimethylsilyl)ethoxy)methyl)-1H-imidazol-2-yl)-7-oxononyl)-6-azaspiro[2.5]octane-1-carboxamide (5_B) which was used to the next step without further purification. LCMS (ESI) calc'd for $C_{44}H_{66}BrN_5O_5Si$ [M+H]$^+$: 856.4, found: 856.4.

Step 3: (1 S,4S)-6$^7$-methoxy-4-(6-oxooctyl)-5$^1$-((2-(trimethylsilyl)ethoxy)methyl)-6$^1$,6$^2$-dihydro-5$^1$H-3-aza-6(6,2)-isoquinolina-15(4,1)-piperidina-5(2,5)-imidazola-1(1,2)-cyclopropanapentadecaphane-6$^1$,2-dione 5_C NaI (50 mg, 0.334 mmol) was added to a stirred mixture of (S)-N-((S)-1-(5-(2-(8-bromooctyl)-7-methoxy-1-oxo-1,2-dihydroisoquinolin-6-yl)-1-((2-(trimethylsilyl)ethoxy)methyl)-1H-imidazol-2-yl)-7-oxononyl)-6-azaspiro[2.5]octane-1-carboxamide (5_B, 71 mg, 0.083 mmol) and DIEA (0.2 mL, 1.145 mmol) in acetonitrile (20 mL) at 27° C. and the mixture was stirred at 80° C. for 15 h. The mixture was concentrated in vacuo to give a residue, then dissolved in ethyl acetate (40 mL). The combined organic fractions were washed with water (3×8 mL), brine (saturated, 8 mL), dried ($Na_2SO_4$), filtered and the solvent was evaporated under reduced pressure to give compound 5_C which was used to the next step without further purification. LCMS (ESI) calc'd for $C_{44}H_{67}N_5O_5Si$ [M+H]$^+$: 774.5, found: 774.5.

Step 4: (1$^1$S,4S)-6$^7$-methoxy-4-(6-oxooctyl)-6$^1$,6$^2$-dihydro-5$^1$H-3-aza-6(6,2)-isoquinolina-15(4,1)-piperidina-5(2,5)-imidazola-1(1,2)-cyclopropanapentadecaphane-6$^1$,2-dione (5)

TFA (4 mL, 51.9 mmol) was added to a stirred mixture of 5_C (48 mg, 0.062 mmol) at 23° C. and the mixture was stirred at 23° C. for 2.5 h. The mixture was concentrated in vacuo. The residue was dissolved in DMF (3 mL) and filtered. The residue was purified by preparative HPLC (reverse phase C-18 column), eluting with acetonitrile/water+0.1% TFA, and then re-purified by preparative HPLC (reverse phase C-18 column), eluting with acetonitrile/water+0.05% $NH_3.H_2O$, to give compound 5. LCMS (ESI) calc'd for $C_{38}H_{53}N_5O_4$ [M+H]+: 644.4, found: 644.4. L-(+)-tartaric acid (6 mg, 0.040 mmol) was added to a stirred mixture of 5 (20 mg, 0.031 mmol) in water (5 mL) at 24° C. and the mixture was stirred at 24° C. for 15 min. The mixture was lyophilized to give the tartrate salt of 5. $^1$H NMR (400 MHz, $D_2O$) δ 7.65 (s, 1H), 7.58 (s, 1H), 7.49 (s, 1H), 7.16 (d, J=7.43 Hz, 1H), 6.62 (d, J=7.43 Hz, 1H), 4.87 (d, J=7.83 Hz, 1H), 4.39 (s, 2H), 3.82 (s, 3H), 3.19-3.30 (m, 1H), 2.66-2.75 (m, 1H), 2.55-2.66 (m, 1H), 2.32-2.45 (m, 4H), 2.06-2.19 (m, 1H), 1.74-2.03 (m, 4H), 1.48-1.73 (m, 6H), 1.30-1.46 (m, 4H), 1.13-1.27 (m, 4H), 0.95-1.11 (m, 4H), 0.75-0.92 (m, 8H), 0.52-0.71 (brs, 2H), 0.35 (brs, 1H), 0.14 (brs, 1H).

Example 10

(3S)-7-methyl-3-(6-oxooctyl)-11,12-dihydro-21H-12-oxa-4,7-diaza-1(6,2)-isoquinolina-2(5,2)-imidazolacyclohexadecaphane-11,5-dione (6)

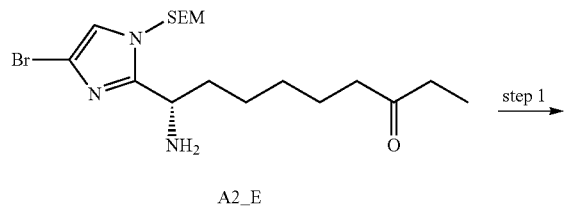

Step 1: Preparation of (S)-tert-butyl (2-((1-(4-bromo-1-((2-(trimethylsilyl)ethoxy)methyl)-1H-imidazol-2-yl)-7-oxononyl)amino)-2-oxoethyl)(methyl)carbamate (6_A)

EDCI (887 mg, 4.62 mmol) and HOBT (354 mg, 2.312 mmol) were added to a stirred mixture of (S)-9-amino-9-(4-bromo-1-((2-(trimethylsilyl)ethoxy)methyl)-1H-imidazol-2-yl)nonan-3-one (A2_E, 1.0 g, 2.312 mmol), 2-((tert-butoxycarbonyl)(methyl)amino)acetic acid (438 mg, 2.315 mmol) and DIPEA (0.8 mL, 4.58 mmol) in DMF (10 mL) at room temperature and the mixture was stirred at room temperature for 16 h. Water (10 mL) was added and the mixture was extracted with ethyl acetate (3×10 mL). The combined organic fractions were washed with brine (saturated, 1×10 mL), dried (Na$_2$SO$_4$), filtered and the solvent was evaporated under reduced pressure. The residue was purified by silica gel column flash chromatography, eluting with petroleum ether/EtOAc=4/1 to give (S)-tert-butyl (2-((1-(4-bromo-1-((2-(trimethylsilyl)ethoxy)methyl)-1H-imidazol-2-yl)-7-oxononyl)amino)-2-oxoethyl)(methyl)carbamate (6_A). LCMS (ESI) calc'd for C$_{26}$H$_{47}$BrN$_4$O$_5$Si [M+H]+: 603.3, 605.3, found: 603.3, 605.3. $^1$H NMR (400 MHz, CDCl$_3$) δ 6.88 (s, 1H), 6.59 (brs, 1H), 5.57 (d, J=10.4 Hz, 1H), 5.02-5.23 (m, 2H), 3.81 (brs, 2H), 3.41-3.57 (m, 2H), 2.30-2.45 (m, 4H), 1.80-1.99 (m, 5H), 1.32-1.62 (m, 14H), 1.03 (t, J=7.34 Hz, 3H), 0.80-0.97 (m, 2H), 0.00 (s, 9H).

Step 2: Preparation of (S)-tert-butyl methyl(2-oxo-2-((7-oxo-1-(4-(1-oxo-1,2-dihydroisoquinolin-6-yl)-1-((2-(trimethylsilyl)ethoxy)methyl)-1H-imidazol-2-yl)nonyl)amino)ethyl)carbamate (6_B)

PdCl$_2$(DTBPF) (65 mg, 0.100 mmol) was added to a stirred mixture of (S)-tert-butyl (2-((1-(4-bromo-1-((2-(trimethylsilyl)ethoxy)methyl)-1H-imidazol-2-yl)-7-oxononyl)amino)-2-oxoethyl)(methyl)carbamate (6_A, 600 mg, 0.994 mmol), 6-(4,4,5,5-tetramethyl-1,3,2-dioxaborolan-2-yl)isoquinolin-1(2H)-one (296 mg, 1.093 mmol) and potassium phosphate (633 mg, 2.98 mmol) in THF (6 mL) and water (0.6 mL) at room temperature and the mixture was stirred at 70° C. for 3 h. 6-(4,4,5,5-tetramethyl-1,3,2-dioxaborolan-2-yl)isoquinolin-1(2H)-one (150 mg, 0.545 mmol) was added and it was stirred at 70° C. for another 2 h. Water (10 mL) was added and the mixture was extracted with ethyl acetate (3×10 mL). The combined organic fractions were washed with brine (saturated, 1×10 mL), dried ($Na_2SO_4$), filtered and the solvent was evaporated under reduced pressure. The residue was purified by silica gel column flash chromatography, eluting with petroleum ether/EtOAc=1/2 to give (S)-tert-butyl methyl(2-oxo-2-((7-oxo-1-(4-(1-oxo-1,2-dihydroisoquinolin-6-yl)-1-((2-(trimethylsilyl)ethoxy)methyl)-1H-imidazol-2-yl)nonyl)amino)ethyl)carbamate (6_B). LCMS (ESI) calc'd for $C_{35}H_{53}N_5O_6Si$ [M+H]$^+$: 668.4, found: 668.4.

Step 3: Preparation of (S)-tert-butyl (2-((1-(4-(2-(4-(4-chlorobutoxy)butyl)-1-oxo-1,2-dihydroisoquinolin-6-yl)-1-((2-(trimethylsilyl)ethoxy)methyl)-1H-imidazol-2-yl)-7-oxononyl)amino)-2-oxoethyl)(methyl)carbamate (6_C)

1-chloro-4-(4-chlorobutoxy)butane (240 mg, 1.205 mmol) was added to a stirred mixture of (S)-tert-butyl methyl(2-oxo-2-((7-oxo-1-(4-(1-oxo-1,2-dihydroisoquinolin-6-yl)-1-((2-(trimethylsilyl)ethoxy)methyl)-1H-imidazol-2-yl)nonyl)amino)ethyl)carbamate (6_B, 400 mg, 0.599 mmol) and $Cs_2CO_3$ (488 mg, 1.497 mmol) in acetonitrile (8 mL) at room temperature and the mixture was heated with stirring at 70° C. for 5 h. The mixture was filtered and the filter cake was washed with ethyl acetate (3×10 mL). The filtrate was concentrated to dryness. The residue was purified by silica gel flash chromatography (ISCORF75; Sepa flash column), eluting with petroleum ether/EtOAc=0~60% to give (S)-tert-butyl (2-((1-(4-(2-(4-(4-chlorobutoxy)butyl)-1-oxo-1,2-dihydroisoquinolin-6-yl)-1-((2-(trimethylsilyl)ethoxy)methyl)-1H-imidazol-2-yl)-7-oxononyl)amino)-2-oxoethyl)(methyl)carbamate (6_C). LCMS (ESI) calc'd for $C_{43}H_{68}ClN_5O_7Si$ [M+H]$^+$: 830.5, found: 830.5. $^1$H NMR (400 MHz, CDCl$_3$) δ 8.38 (d, J=8.2 Hz, 1H), 7.91 (s, 1H), 7.77 (d, J=7.8 Hz, 1H), 7.33 (s, 1H), 7.06 (d, J=7.4 Hz, 1H), 6.88 (d, J=8.6 Hz, 1H), 6.52 (d, J=7.4 Hz, 1H), 5.60 (d, J=10.2 Hz, 1H), 5.22-5.29 (m, 1H), 5.19 (d, J=10.9 Hz, 1H), 4.02 (t, J=7.2 Hz, 2H), 3.85 (brs, 2H), 3.50-3.60 (m, 4H), 3.37-3.48 (m, 4H), 2.92 (brs, 3H), 2.32-2.41 (m, 4H), 1.77-1.87 (m, 8H), 1.50-1.74 (m, 7H), 1.29-1.40 (m, 9H), 1.01 (t, J=7.4 Hz, 3H), 0.86-0.98 (m, 2H), 0.00 (s, 9H).

Step 4: Preparation of (S)-N-(1-(4-(2-(4-(4-chlorobutoxy)butyl)-1-oxo-1,2-dihydroisoquinolin-6-yl)-1-((2-(trimethylsilyl)ethoxy)methyl)-1H-imidazol-2-yl)-7-oxononyl)-2-(methylamino)acetamide (6_D)

HCl/MeOH (1.5 mL, 6.00 mmol) was added to a stirred mixture of (S)-tert-butyl (2-((1-(4-(2-(4-(4-chlorobutoxy)butyl)-1-oxo-1,2-dihydroisoquinolin-6-yl)-1-((2-(trimethylsilyl)ethoxy)methyl)-1H-imidazol-2-yl)-7-oxononyl)amino)-2-oxoethyl)(methyl)carbamate (6_C, 290 mg, 0.349 mmol) in DCM (30 mL) at room temperature and the mixture was stirred at room temperature for 3 h. Aqueous $NaHCO_3$ (saturated, 3 mL) was added to neutralize it then water (10 mL) was added, and the mixture was extracted with DCM (3×20 mL). The combined organic fractions were washed with brine (saturated, 1×20 mL), dried ($Na_2SO_4$), filtered and the solvent was evaporated under reduced pressure to give crude (S)-N-(1-(4-(2-(4-(4-chlorobutoxy)butyl)-1-oxo-1,2-dihydroisoquinolin-6-yl)-1-((2-(trimethylsilyl)ethoxy)methyl)-1H-imidazol-2-yl)-7-oxononyl)-2-(methylamino)acetamide (6_D) which was used the next step without further purification. LCMS (ESI) calc'd for $C_{38}H_{60}ClN_5O_5Si$ [M+H]$^+$: 730.4, found: 730.4.

Step 5: Preparation of Compound 6_E

NaI (246 mg, 1.643 mmol) was added to a stirred mixture of (S)-N-(1-(4-(2-(4-(4-chlorobutoxy)butyl)-1-oxo-1,2-dihydroisoquinolin-6-yl)-1-((2-(trimethylsilyl)ethoxy)methyl)-1H-imidazol-2-yl)-7-oxononyl)-2-(methylamino)acetamide (6_D, 240 mg, 0.329 mmol) and DIPEA (0.28 mL, 1.603 mmol) in acetonitrile (40 mL) at room temperature and the mixture was heated with stirring at 85° C. for 36 h. Acetonitrile was removed by evaporator, then water (10 mL) was added and the mixture was extracted with ethyl acetate (3×10 mL). The combined organic fractions were washed with brine (saturated, 1×10 mL), dried ($Na_2SO_4$), filtered and the solvent was evaporated under reduced pressure. The residue was purified by silica gel flash chromatography (ISCORF75; Sepa flash column), eluting with EtOAc/MeOH=0~10% to give 6_E which was used to the next step without further purification. LCMS (ESI) calc'd for $C_{38}H_{59}N_5O_5Si$ [M+H]$^+$: 694.4, found: 694.8.

Step 6: Preparation of Compound 6

TFA (1.9 mL, 24.66 mmol) was added to a stirred mixture of 6_E (190 mg, 0.274 mmol) in DCM (2 mL) at room temperature and the mixture was stirred at room temperature for 2 h. All the volatiles were removed by evaporator. The residue was purified by preparative HPLC (reverse phase C-18 column), eluting with acetonitrile/water+0.10% TFA, to give the crude product, then it was dissolved in MeOH and neutralized with $NaHCO_3$ (sat.). The mixture was purified by preparative HPLC (reverse phase C-18 column), eluting with acetonitrile/water+0.05% $NH_3 \cdot H_2O$, to give compound 6. L-(+)-tartaric acid (15 mg, 0.100 mmol) was added to a stirred mixture of 6 (54 mg, 0.096 mmol) in acetonitrile (2 mL) and water (2 mL) at room temperature and the mixture was made dry by lyophilization to give the tartrate of 6. LCMS (ESI) calc'd for $C_{32}H_{45}N_5O_4$ [M+H]$^+$: 564.4, found: 564.2. $^1$H NMR (400 MHz, MeOD) δ 8.05-8.17 (m, 1H), 7.77-7.95 (m, 1H), 7.64-7.94 (m, 1H), 7.49-7.58 (m, 1H), 7.04-7.20 (m, 1H), 6.39-6.50 (m, 1H), 5.06-5.15 (m, 1H), 4.50 (s, 3H), 4.42-4.54 (m, 1H), 3.99-4.18 (m, 2H), 3.69-3.84 (m, 2H), 3.38-3.49 (m, 4H), 3.18-3.26 (m, 2H), 2.91 (s, 3H), 2.36-2.45 (m, 4H), 1.80-2.00 (m, 4H), 1.60-1.76 (m, 4H), 1.47-1.58 (m, 4H), 1.23-1.44 (m, 4H), 0.96 (t, J=7.2 Hz, 3H).

Example 11

(11S,4S)-4-(6-oxooctyl)-61,62-dihydro-3-aza-5(2,5)-oxazola-6(6,1)-quinolina-12(4,1)-piperidina-1(1,2)-cyclopropanadodecaphane-62,2-dione & (11S,4S)-4-(6-oxooctyl)-61,62-dihydro-3-aza-5(2,5)-oxazola-6(6,1)-quinolina-12(4,1)-piperidina-1(1,2)-cyclopropanadodecaphane-62,2-dione (7 & 8)

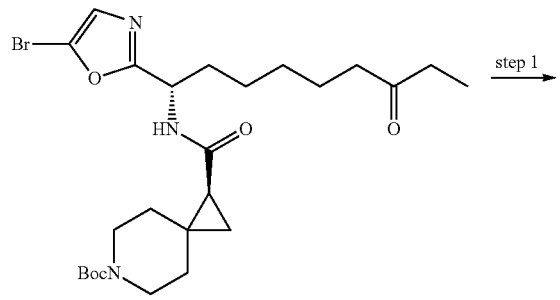

A6

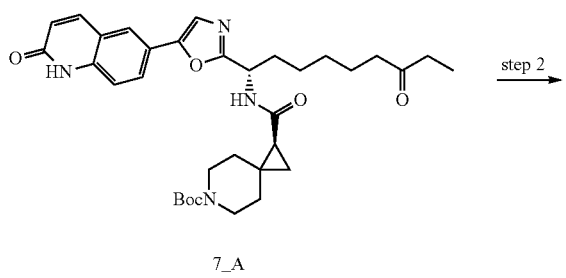

7_A

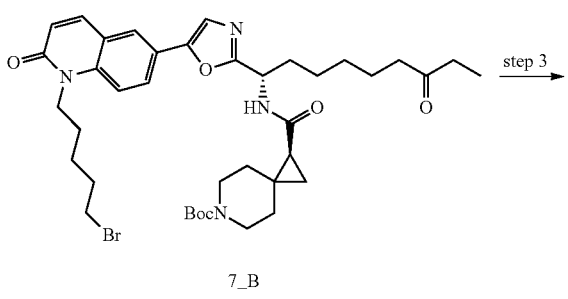

7_B

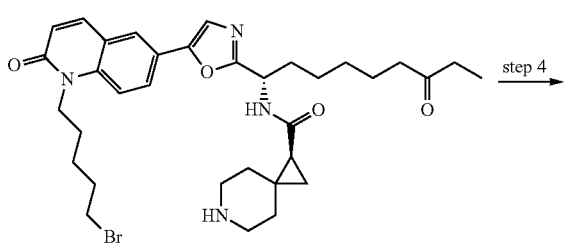

7_C

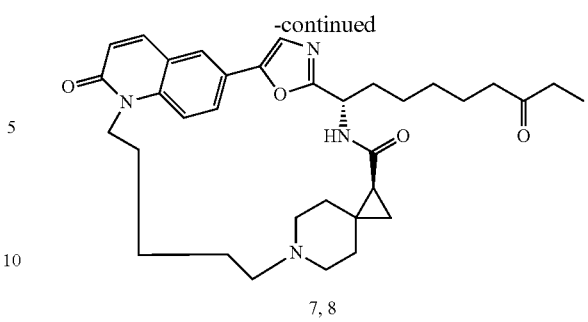

7, 8

Step 1: Preparation of (S)-tert-butyl 1-(((S)-7-oxo-1-(5-(2-oxo-1,2-dihydroquinolin-6-yl)oxazol-2-yl)nonyl)carbamoyl)-6-azaspiro[2.5]octane-6-carboxylate (7_A)

PdCl$_2$(DTBPF) (72 mg, 0.110 mmol) was added to a stirred mixture of K$_3$PO$_4$ (589 mg, 2.78 mmol), (S)-tert-butyl 1-(((S)-1-(5-bromooxazol-2-yl)-7-oxononyl)carbamoyl)-6-azaspiro[2.5]octane-6-carboxylate (A6, 600 mg, 1.110 mmol) and 6-(4,4,5,5-tetramethyl-1,3,2-dioxaborolan-2-yl)quinolin-2(1H)-one (602 mg, 2.220 mmol) in THF (12 mL), water (2.5 mL) at room temperature and the mixture was stirred at 80° C. for 6 h under N2. The mixture was cooled to room temperature, and extracted with ethyl acetate (3×30 mL). The combined organic fractions were washed with brine (saturated, 2×30 mL), dried (Na$_2$SO$_4$), filtered and the solvent was evaporated under reduced pressure. The residue was purified by silica gel column flash chromatography, eluting with petroleum ether/EtOAc=50~80% to give (S)-tert-butyl 1-(((S)-7-oxo-1-(5-(2-oxo-1,2-dihydroquinolin-6-yl)oxazol-2-yl)nonyl)carbamoyl)-6-azaspiro[2.5]octane-6-carboxylate (7_A). LCMS (ESI) calc'd for C$_{34}$H$_{44}$N$_4$O$_6$ [M+H]$^+$: 605.4, found: 605.4.

Step 2: Preparation of (S)-tert-butyl 1-(((S)-1-(5-(1-(5-bromopentyl)-2-oxo-1,2-dihydroquinolin-6-yl)oxazol-2-yl)-7-oxononyl)carbamoyl)-6-azaspiro[2.5]octane-6-carboxylate (7_B)

Cs$_2$CO$_3$ (337 mg, 1.034 mmol) was added to a stirred mixture of 1,5-dibromopentane (285 mg, 1.240 mmol) and (S)-tert-butyl 1-(((S)-7-oxo-1-(5-(2-oxo-1,2-dihydroquinolin-6-yl)oxazol-2-yl)nonyl)carbamoyl)-6-azaspiro[2.5]octane-6-carboxylate (7_A, 250 mg, 0.413 mmol) in MeCN (8 mL) at room temperature and the mixture was heated with stirring at 65° C. for 4 h. The mixture was extracted with ethyl acetate (3×10 mL). The combined organic fractions were washed with brine (saturated, 3×5 mL), dried (Na$_2$SO$_4$), filtered and the solvent was evaporated under reduced pressure. The residue was purified by silica gel column flash chromatography, eluting with petroleum ether/EtOAc=0~60% to give (S)-tert-butyl 1-(((S)-1-(5-(1-(5-bromopentyl)-2-oxo-1,2-dihydroquinolin-6-yl)oxazol-2-yl)-7-oxononyl)carbamoyl)-6-azaspiro[2.5]octane-6-carboxylate (7_B) and (S)-tert-butyl 1-(((S)-1-(5-(2-((5-bromopentyl)oxy)quinolin-6-yl)oxazol-2-yl)-7-oxononyl)carbamoyl)-6-azaspiro[2.5]octane-6-carboxylate. LCMS (ESI) calc'd for C$_{39}$H$_{53}$BrN$_4$O$_6$ [M+H]$^+$: 754.3, found: 755.3.

Step 3: Preparation of (S)-N-((S)-1-(5-(1-(5-bromopentyl)-2-oxo-1,2-dihydroquinolin-6-yl)oxazol-2-yl)-7-oxononyl)-6-azaspiro[2.5]octane-1-carboxamide (7_C)

HCl (1 mL, 12.18 mmol) was added to a stirred mixture of (S)-tert-butyl 1-(((S)-1-(5-(1-(5-bromopentyl)-2-oxo-1,2- dihydroquinolin-6-yl)oxazol-2-yl)-7-oxononyl)carbamoyl)-6-azaspiro[2.5]octane-6-carboxylate (7_B, 150 mg, 0.199 mmol) in DCM at room temperature and the mixture was stirred at room temperature for 2 h. The mixture was filtered and the filter cake was washed with MeOH (30 mL). The filtrate was concentrated to dryness to afford the title compound which was used to the next step without further purification. LCMS (ESI) calc'd for $C_{34}H_{45}BrN_4O_4$ [M+H]$^+$: 654.3, found: 655.3.

Step 4: Preparation of Compounds 7 and 8

NaI (30 mg, 0.200 mmol) was added to a stirred mixture of (S)-N-((S)-1-(5-(1-(5-bromopentyl)-2-oxo-1,2-dihydroquinolin-6-yl)oxazol-2-yl)-7-oxononyl)-6-azaspiro[2.5]octane-1-carboxamide (7_C, 130 mg, 0.199 mmol) and DIEA (0.135 mL, 0.774 mmol) in MeCN (3 mL) at room temperature and the mixture was stirred at 75° C. for 3 h. The mixture was concentrated. The residue was purified by preparative HPLC (reverse phase C-18 column), eluting with acetonitrile/water+0.1% TFA, to give the title compounds.

7, first peak. LCMS (ESI) calc'd for $C_{35}H_{46}N_4O_4$ [M+H]$^+$: 573.3, found: 573.1. $^1$H NMR (400 MHz, MeOD) δ 7.94-8.09 (m, 2H), 7.89 (d, J=8.8 Hz, 1H), 7.38-7.61 (m, 1H), 6.75 (d, J=9.7 Hz, 1H), 5.00-5.46 (m, 1H), 3.36-3.51 (m, 1H), 2.98-3.28 (m, 1H), 2.77-3.01 (m, 1H), 2.50 (q, J=7.48 Hz, 4H), 2.17 (d, J=1.3 Hz, 4H), 1.74-1.99 (m, 3H), 1.48-1.72 (m, 6H), 1.29-1.46 (m, 5H), 0.25-1.15 (m, 3H).

8, second peak. LCMS (ESI) calc'd for $C_{35}H_{46}N_4O_4$ [M+H]$^+$: 573.3, found: 573.2. $^1$H NMR (400 MHz, MeOD) δ 8.04 (s, 1H), 7.87-7.98 (m, 2H), 7.47-7.61 (m, 2H), 6.71 (d, J=9.5 Hz, 1H), 5.23 (d, J=6.4 Hz, 1H), 2.69-2.89 (m, 1H), 2.47 (q, J=7.20 Hz, 5H), 2.10 (brs, 3H), 1.98 (brs, 3H), 1.73 (brs, 2H), 1.60 (d, J=6.4 Hz, 3H), 1.41 (brs, 1H), 1.26-1.32 (m, 3H), 1.21 (brs, 2H), 1.08 (brs, 3H), 1.01 (t, J=7.4 Hz, 5H), 0.87 (brs, 2H).

Compound 9 was prepared using a similar procedure as described above and starting from the byproduct in step 2.

Example 12

(3S,6S)-6-(6-oxooctyl)-5,8,20,25,31-pentaazaheptacyclo[23.2.2.1~7,10~.1~11,15~.0~1,3~.0~14,19~.0.0~16,20~]hentriaconta-7,9,11(30),12,14-pentaen-4-one (10)

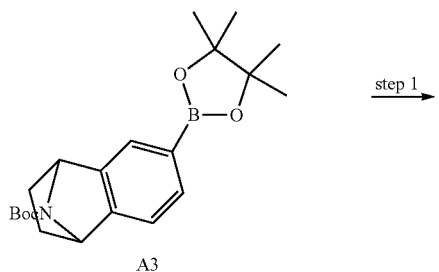

A3 step 1

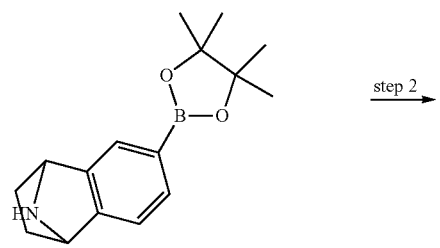

10_A step 2

| Structure | Exact Mass [M + H]$^+$ | Observed [M + H]$^+$ |
|---|---|---|
| 9 | Calc'd 573.3, found | 573.2 |

-continued

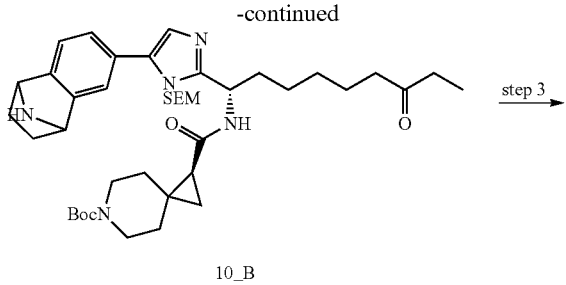

10_B

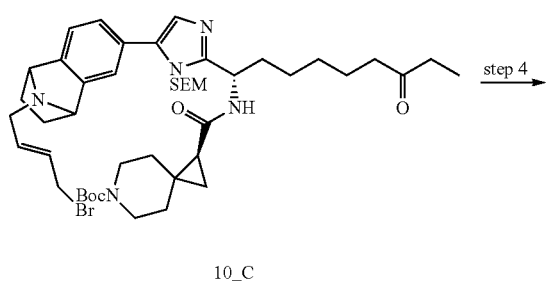

10_C

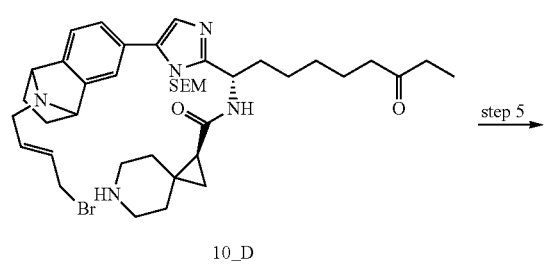

10_D

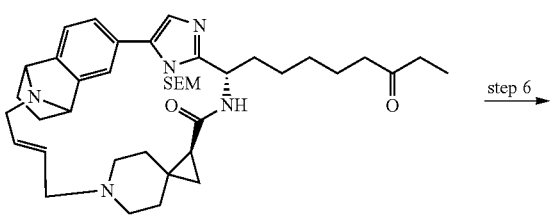

10_E

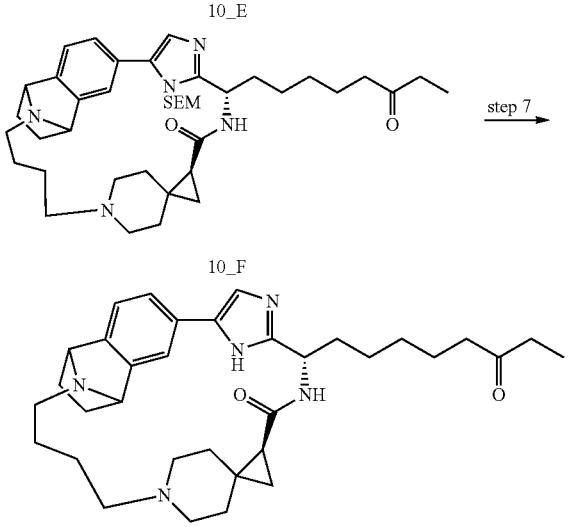

10_F

Step 1: Preparation of 6-(4,4,5,5-tetramethyl-1,3,2-dioxaborolan-2-yl)-1,2,3,4-tetrahydro-1,4-epiminonaphthalene (10_A)

TFA (1.5 mL, 19.47 mmol) was added to a stirred mixture of tert-butyl 6-(4,4,5,5-tetramethyl-1,3,2-dioxaborolan-2-yl)-1,2,3,4-tetrahydro-1,4-epiminonaphthalene-9-carboxylate (A3, 500 mg, 1.347 mmol) in DCM (5.0 mL) at room temperature and the mixture was stirred at 26° C. for 2 h. The mixture was concentrated, adjusted to pH 8 with NaHCO₃ solution, extracted with EtOAc (2*10 mL), washed with brine (5 mL), dried over Na₂SO₄, filtered and concentrated to afford 6-(4,4,5,5-tetramethyl-1,3,2-dioxaborolan-2-yl)-1,2,3,4-tetrahydro-1,4-epiminonaphthalene (10_A) which was used to the next step without further purification. LCMS (ESI) calc'd for $C_{16}H_{22}BNO_2$ [M+H]⁺: 272.2, found: 272.1.

Step 2: Preparation of (1S)-tert-butyl 1-(((1S)-7-oxo-1-(5-(1,2,3,4-tetrahydro-1,4-epiminonaphthalen-6-yl)-1-((2-(trimethylsilyl)ethoxy)methyl)-1H-imidazol-2-yl)nonyl)carbamoyl)-6-azaspiro[2.5]octane-6-carboxylate (10_B)

PdCl₂(DTBPF) (40 mg, 0.061 mmol) was added to a stirred mixture of (S)-tert-butyl 1-(((S)-1-(5-bromo-1-((2-(trimethylsilyl)ethoxy)methyl)-1H-imidazol-2-yl)-7-oxononyl)carbamoyl)-6-azaspiro[2.5]octane-6-carboxylate (A2, 500 mg, 0.747 mmol), 6-(4,4,5,5-tetramethyl-1,3,2-dioxaborolan-2-yl)-1,2,3,4-tetrahydro-1,4-epiminonaphthalene (10_A, 304 mg, 1.120 mmol), and potassium carbonate (310 mg, 2.240 mmol) in THF (10 mL) and water (2 mL) at room temperature and the mixture was stirred at 80° C. for 8 h under N2. Then it was filtered and concentrated. The residue was purified by silica gel column flash chromatography, eluting with DCM/MeOH=50:1 to 10:1 to give (1S)-tert-butyl 1-(((1S)-7-oxo-1-(5-(1,2,3,4-tetrahydro-1,4-epiminonaphthalen-6-yl)-1-((2-(trimethylsilyl)ethoxy)methyl)-1H-imidazol-2-yl)nonyl)carbamoyl)-6-azaspiro[2.5]octane-6-carboxylate (10_B). LCMS (ESI) calc'd for $C_{41}H_{63}N_5O_5Si$ [M+H]⁺: 734.5, found: 734.4.

Step 3: Preparation of (1S)-tert-butyl 1-(((1S)-1-(5-(9-((E)-4-bromobut-2-en-1-yl)-1,2,3,4-tetrahydro-1,4-epiminonaphthalen-6-yl)-1-((2-(trimethylsilyl)ethoxy)methyl)-1H-imidazol-2-yl)-7-oxononyl)carbamoyl)-6-azaspiro[2.5]octane-6-carboxylate (10_C)

(E)-1,4-dibromobut-2-ene (37.9 mg, 0.177 mmol) in 0.3 mL of CH₃CN was added to a stirred mixture of (1S)-tert-butyl 1-(((1S)-7-oxo-1-(5-(1,2,3,4-tetrahydro-1,4-epiminonaphthalen-6-yl)-1-((2-(trimethylsilyl)ethoxy)methyl)-1H-imidazol-2-yl)nonyl)carbamoyl)-6-azaspiro[2.5]octane-6-carboxylate (10_B, 130 mg, 0.177 mmol) and DIPEA (62 μL, 0.355 mmol) in acetonitrile (3.0 mL) at room temperature and the mixture was stirred at 26° C. for 30 min. Water (5.0 mL) was added and the mixture was extracted with ethyl acetate (20 mL). The combined organic fractions were washed with brine (saturated, 5.0 mL), dried (Na₂SO₄), filtered and the solvent was evaporated under reduced pressure. The residue was purified by preparative TLC on silica gel, eluting with DCM/MeOH=10:1 to give (1S)-tert-butyl 1-(((1S)-1-(5-(9-((E)-4-bromobut-2-en-1-yl)-1,2,3,4-tetrahydro-1,4-epiminonaphthalen-6-yl)-1-((2-(trimethylsilyl)ethoxy)methyl)-1H-imidazol-2-yl)-7-oxononyl)carbamoyl)-

6-azaspiro[2.5]octane-6-carboxylate (10_C) which was used in the next step without further purification.

Step 4: Preparation of (1S)-N-((1S)-1-(5-(9-((E)-4-bromobut-2-en-1-yl)-1,2,3,4-tetrahydro-1,4-epiminonaphthalen-6-yl)-1-((2-(trimethylsilyl)ethoxy)methyl)-1H-imidazol-2-yl)-7-oxononyl)-6-azaspiro[2.5]octane-1-carboxamide (10_D)

HCl/MeOH (3.0 mL, 12.00 mmol) was added to a stirred mixture of (1S)-tert-butyl 1-(((1S)-1-(5-(9-((E)-4-bromobut-2-en-1-yl)-1,2,3,4-tetrahydro-1,4-epiminonaphthalen-6-yl)-1-((2-(trimethylsilyl)ethoxy)methyl)-1H-imidazol-2-yl)-7-oxononyl)carbamoyl)-6-azaspiro[2.5]octane-6-carboxylate (10_C, 50 mg, 0.058 mmol) in DCM (3.0 mL) at room temperature and the mixture was stirred at 26° C. for 3 h. The mixture was concentrated with N2 flow to afford (1S)-N-((1S)-1-(5-(9-((E)-4-bromobut-2-en-1-yl)-1,2,3,4-tetrahydro-1,4-epiminonaphthalen-6-yl)-1-((2-(trimethylsilyl)ethoxy)methyl)-1H-imidazol-2-yl)-7-oxononyl)-6-azaspiro[2.5]octane-1-carboxamide (10_D) which was used in the next step without further purification. LCMS (ESI) calc'd for $C_{40}H_{60}BrN_5O_3Si$ [M+H]$^+$: 766.4, found: 790.5.

Step 8: Preparation of Compound 10_E

DIPEA (40 μL, 0.229 mmol) was added to a stirred mixture of (1S)-N-((1S)-1-(5-(9-((E)-4-bromobut-2-en-1-yl)-1,2,3,4-tetrahydro-1,4-epiminonaphthalen-6-yl)-1-((2-(trimethylsilyl)ethoxy)methyl)-1H-imidazol-2-yl)-7-oxononyl)-6-azaspiro[2.5]octane-1-carboxamide (10_D, 44 mg, 0.057 mmol) in acetonitrile (3.0 mL) at room temperature and the mixture was stirred at 26° C. for 2 h. The mixture was concentrated with N2 flow, and the residue was purified by preparative TLC on silica gel, eluting with DCM/MeOH (TEA)=10:1 (5 drops) to give product 10_E. LCMS (ESI) calc'd for $C_{40}H_{59}N_5O_3Si$ [M+H]$^+$: 686.4, found: 686.4.

Step 9: Preparation of Compound 10_F

To a solution of 10_E (22 mg, 0.032 mmol) in MeOH (2.0 mL) was added Pd—C (10 mg, 0.094 mmol) (10%, wet) under Ar. The suspension was degassed under vacuum and purged with N2 several times. The mixture was then stirred under H$_2$ (Pressure: 15 psi) at 26° C. for 1 h. The mixture was then filtered and concentrated to afford 10_F which was used in the next step without further purification. LCMS (ESI) calc'd for $C_{40}H_{61}N_5O_3Si$ [M+H]$^+$: 688.5, found: 688.4.

Step 10: Preparation of 10

TFA (1.0 mL, 12.98 mmol) was added to a stirred mixture of 10_F (20 mg, 0.029 mmol) in DCM (1.0 mL) at room temperature and the mixture was stirred at 26° C. for 2 h, then concentrated. The residue was purified by preparative HPLC (reverse phase C-18 column), eluting with acetonitrile/water+0.1% TFA, to give compound 10. LCMS (ESI) calc'd for $C_{34}H_{47}N_5O_2$ [M+H]$^+$: 558.4, found: 558.2. $^1$H NMR (400 MHz, MeOD) δ 8.31 (brs, 1H), 7.76-7.94 (m, 2H), 7.58-7.72 (m, 1H), 5.33 (brs, 1H), 5.22 (brs, 1H), 5.16-5.41 (m, 1H), 4.94-5.12 (m, 4H), 3.49-3.67 (m, 1H), 2.79-3.33 (m, 10H), 2.75-3.32 (m, 1H), 2.35-2.68 (m, 7H), 1.96-2.72 (m, 1H), 1.93-2.34 (m, 3H), 2.32 (br s, 1H), 1.82 (brs, 4H), 1.52-1.68 (m, 4H), 1.52-1.92 (m, 1H), 1.15-1.46 (m, 6H), 0.96-1.11 (m, 4H).

Example 13

(3S,6S)-6-(6-oxooctyl)-21-oxa-5,8,18,25,32-pentaazahexacyclo[23.2.2.1~7,10~0.1~11,15~0.1~14,18~0.0~1,3~] dotriaconta-7,9,11(31),12,14,16-hexaene-4,30-dione (11)

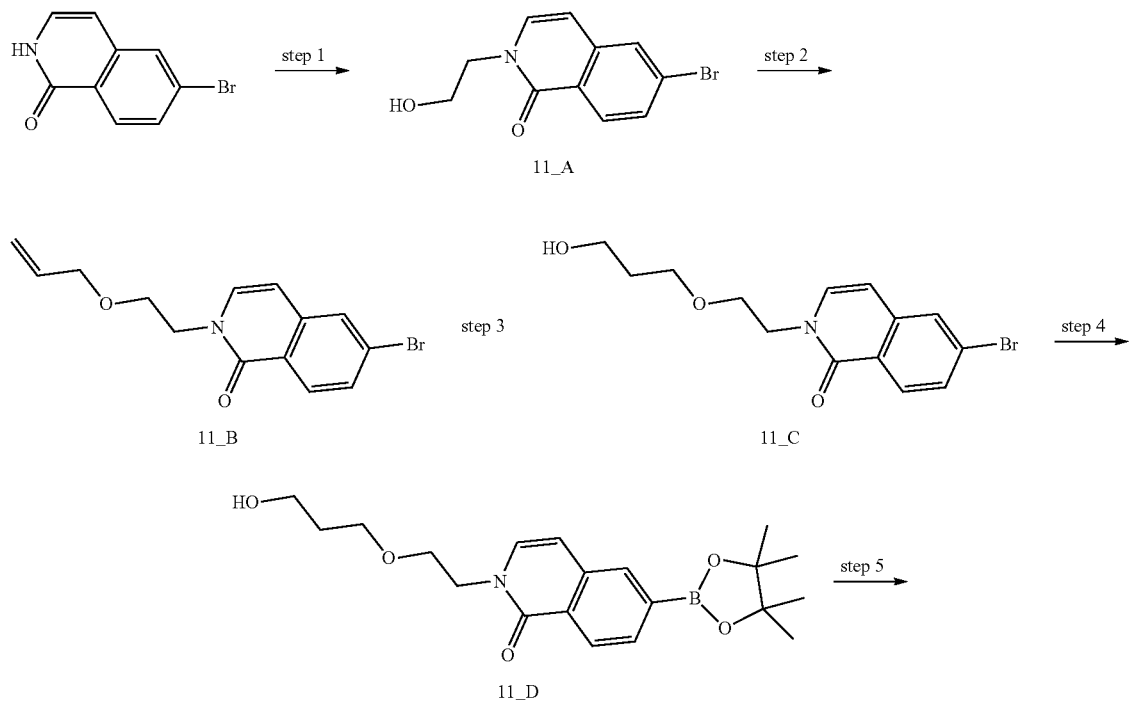

-continued
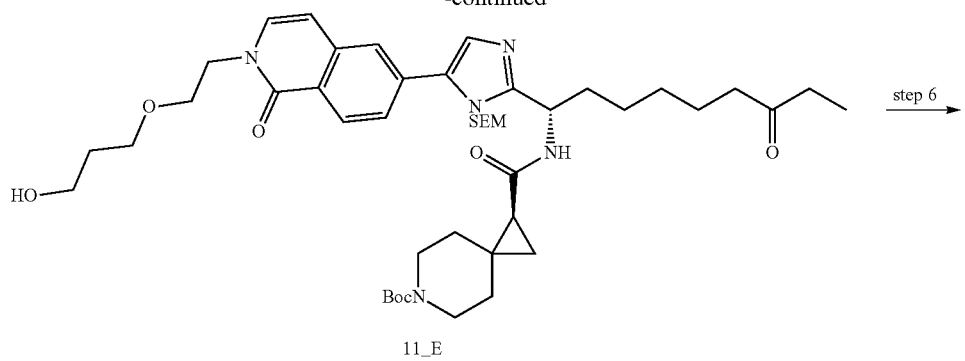# step 6
11_E
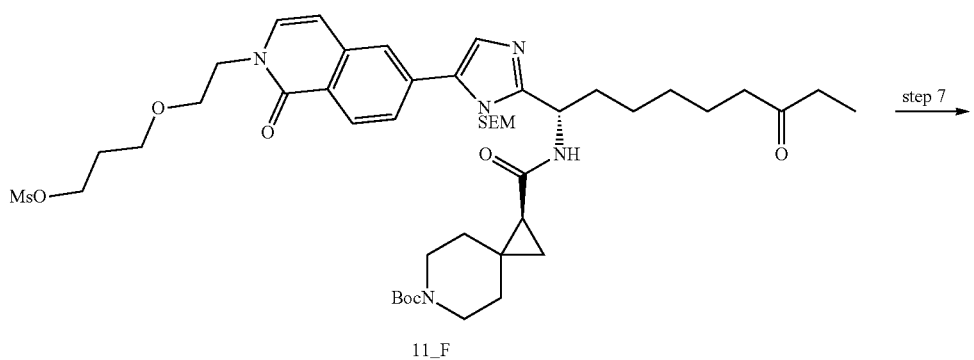# step 7
11_F
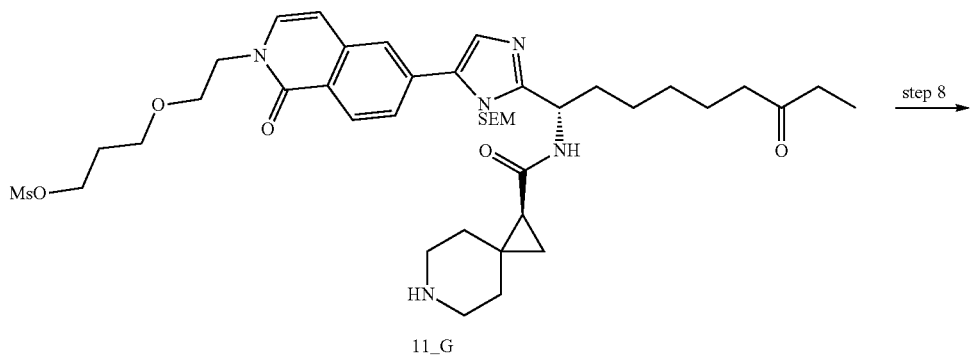# step 8
11_G
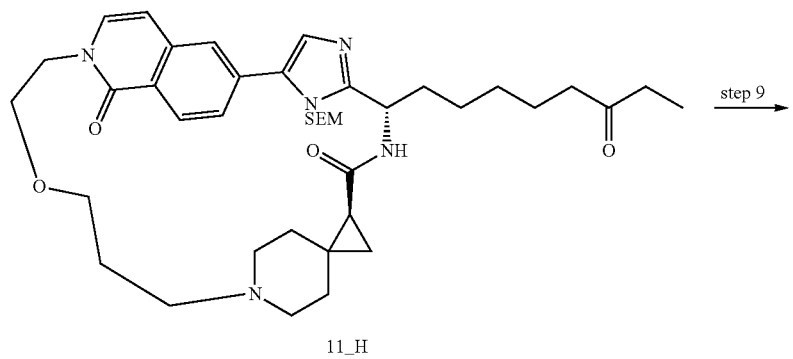# step 9
11_H

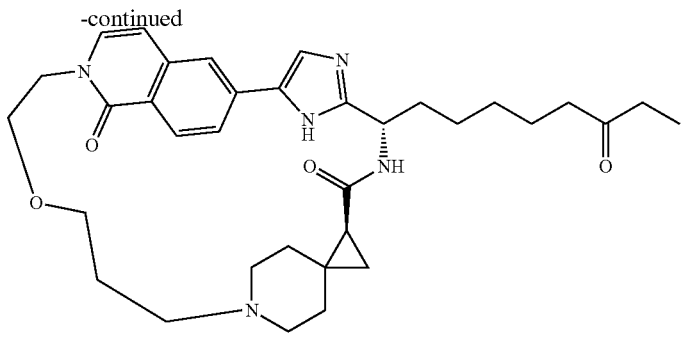

11

Step 1: 6-bromo-2-(2-hydroxyethyl)isoquinolin-1(2H)-one (11_A)

2-bromoethanol (60 mg, 0.480 mmol) was added to a stirred mixture of 6-bromoisoquinolin-1(2H)-one (100 mg, 0.446 mmol) and $Cs_2CO_3$ (175 mg, 0.536 mmol) in DMF (5 mL). The mixture was stirred at 80° C. for 10 h. The mixture was cooled, water (20 mL) was added and the mixture was extracted with ethyl acetate (2×10 mL). The combined organic fractions were washed with brine (saturated, 30 mL), dried ($Na_2SO_4$), filtered and the solvent was evaporated under reduced pressure. The residue was purified by silica gel column flash chromatography, eluting with petroleum ether/EtOAc=0 to 50% to give 6-bromo-2-(2-hydroxyethyl)isoquinolin-1(2H)-one (11_A). LCMS (ESI) calc'd for $C_{11}H_{10}BrNO_2$ $[M+H]^+$: 267.9, 269.9, found: 267.8, 269.8.

Step 2: 2-(2-(allyloxy)ethyl)-6-bromoisoquinolin-1(2H)-one (11_B)

NaH (155 mg, 3.88 mmol) was added to a stirred solution of 6-bromo-2-(2-hydroxyethyl)isoquinolin-1(2H)-one (11_A, 800 mg, 2.98 mmol) in DMF (3 mL) at 0° C. in an ice water bath and the mixture was stirred at this temperature for 30 min. Then, 3-bromoprop-1-ene (433 mg, 3.58 mmol) was added to the stirred mixture and the mixture was stirred at 0° C. for 1 h. Water (10 mL) was added and the mixture was extracted with ethyl acetate (2×20 mL). The combined organic fractions were washed with brine (20 mL), dried ($Na_2SO_4$), filtered and the solvent was evaporated under reduced pressure. The residue was purified by silica gel column flash chromatography, eluting with petroleum ether/EtOAc=100 to 1:1 give 2-(2-(allyloxy)ethyl)-6-bromoisoquinolin-1(2H)-one (11_B). LCMS (ESI) calc'd for $C_{14}H_{14}BrNO_2$ $[M+H]^+$: 308.0, 310.0, found: 307.7, 309.7.

Step 3: 6-bromo-2-(2-(3-hydroxypropoxy)ethyl)isoquinolin-1(2H)-one (11_C)

2-(2-(allyloxy)ethyl)-6-bromoisoquinolin-1(2H)-one (11_B, 400 mg, 1.298 mmol) in THF (5 mL) was cooled at 0° C. and 9-BBN (10 mL, 5.00 mmol) was added. The mixture was stirred at 80° C. for 12 h. Then it was cooled to 0° C., hydrogen peroxide (10 mL, 30%) was added followed by sodium hydroxide (10 ml, 20%) and the mixture stirred for 30 min. The THF was evaporated and aqueous $NaHCO_3$ (saturated, 20 mL) was added and the mixture was extracted with DCM (20×2 mL). The combined organic fractions were washed with brine (saturated, 20 mL), dried ($Na_2SO_4$), filtered and the solvent was evaporated under reduced pressure. The residue was purified by preparative TLC on silica gel, eluting with petroleum ether/EtOAc=1:1 to give 6-bromo-2-(2-(3-hydroxypropoxy)ethyl)isoquinolin-1(2H)-one (11_C). LCMS (ESI) calc'd for $C_{14}H_{16}BrNO_3$ $[M+H]^+$: 326.0, 328.0, found: 326.0, 328.0, tR=1.033 min.

Step 4: 2-(2-(3-hydroxypropoxy)ethyl)-6-(4,4,5,5-tetramethyl-1,3,2-dioxaborolan-2-yl)isoquinolin-1(2H)-one (11_D)

Potassium acetate (298 mg, 3.04 mmol) and BPD (334 mg, 1.315 mmol) were added to a stirred mixture of 6-bromo-2-(2-(3-hydroxypropoxy)ethyl)isoquinolin-1(2H)-one (11_C, 330 mg, 1.012 mmol) in 1,4-dioxane (5 mL) at room temperature, the mixture was replaced with N2, then $PdCl_2$(dppf) (74 mg, 0.101 mmol) was added. The mixture was heated with stirring at 100° C. for 2 h under N2. The mixture was cooled to room temperature and concentrated. Then, petroleum ether/EtOAc=5:1 was added and the mixture was stirred for 30 min, filtered and the solvent was evaporated under reduced pressure. The residue was purified by Pre-TLC on silica gel, eluting with petroleum ether/EtOAc=1:2 to give 2-(2-(3-hydroxypropoxy)ethyl)-6-(4,4,5,5-tetramethyl-1,3,2-dioxaborolan-2-yl)isoquinolin-1(2H)-one (11_D). LCMS (ESI) calc'd for $C_{20}H_{28}BNO_5$ $[M+H]^+$: 374.2, found: 374.2.

Step 5: (S)-tert-butvl 1-(((S)-1-(5-(2-(2-(3-hydroxypropoxy)ethyl)-1-oxo-1,2-dihydroisoquinolin-6-yl)-1-(2-(trimethylsilyl)ethoxy)methyl)-1H-imidazol-2-yl)-7-oxononyl)carbamoyl)-6-azaspiro[2.5]octane-6-carboxylate (11_E)

$PdCl_2$(DTBPF) (35 mg, 0.054 mmol) was added to a mixture of 2-(2-(3-hydroxypropoxy)ethyl)-6-(4,4,5,5-tetramethyl-1,3,2-dioxaborolan-2-yl)isoquinolin-1(2H)-one (11_D, 200 mg, 0.536 mmol), (S)-tert-butyl 1-(((S)-1-(5-bromo-1-((2-(trimethylsilyl)ethoxy)methyl)-1H-imidazol-2-yl)-7-oxononyl)carbamoyl)-6-azaspiro[2.5]octane-6-carboxylate (D1, 431 mg, 0.643 mmol) and $K_3PO_4$ (341 mg, 1.607 mmol) in co-solvents of THF (5 mL) and water (1 mL) at 24° C. and the mixture was stirred at 80° C. for 2 h. The mixture was diluted with water (10 mL), and extracted with ethyl acetate (3×20 mL). The combined organic fractions were washed with brine (saturated, 20 mL), dried ($Na_2SO_4$), filtered and the solvent was evaporated under reduced pressure. The residue was purified by preparative TLC on silica gel, eluting with petroleum ether/EtOAc=1:100 to give (S)-tert-butyl 1-(((S)-1-(5-(2-(2-(3-hydroxypropoxy)ethyl)-1-oxo-1,2-dihydroisoquinolin-6-yl)-1-((2-(trimethylsilyl)

ethoxy)methyl)-1H-imidazol-2-yl)-7-oxononyl)carbamoyl)-6-azaspiro[2.5]octane-6-carboxylate (11_E). LCMS (ESI) calc'd for $C_{45}H_{69}N_5O_8Si$ [M+H]$^+$: 836.4, found: 836.6.

Step 6: (S)-tert-butvl 1-(((S)-1-(5-(2-(2-(3-((methyl-sulfonyl)oxy)propoxy)ethyl)-1-oxo-1,2-dihydroiso-quinolin-6-yl)-1-((2-(trimethylsilyl)ethoxy)methyl)-1H-imidazol-2-yl)-7-oxononyl)carbamoyl)-6-azaspiro[2.5]octane-6-carboxylate (11_F)

MsCl (320 mg, 2.79 mmol) was added to the mixture of TEA (0.2 mL, 1.435 mmol) and (S)-tert-butyl 1-(((S)-1-(5-(2-(2-(3-hydroxypropoxy)ethyl)-1-oxo-1,2-dihydroisoqui-nolin-6-yl)-1-((2-(trimethylsilyl)ethoxy)methyl)-1H-imidazol-2-yl)-7-oxononyl)carbamoyl)-6-azaspiro[2.5]octane-6-carboxylate (11_E, 200 mg, 0.239 mmol) in DCM (2 mL) at 0° C. The resultant mixture was stirred at 25° C. for 1 h. The mixture was cooled, diluted with DCM (4 mL), washed with aqueous NaHCO$_3$ (saturated, 5 mL), dried (Na$_2$SO$_4$), filtered and the solvent was evaporated under reduced pressure. The residue was purified by preparative TLC on silica gel, eluting with petroleum ether/EtOAc=1:2 to give (S)-tert-butyl 1-(((S)-1-(5-(2-(2-(3-((methylsulfonyl)oxy)propoxy) ethyl)-1-oxo-1,2-dihydroisoquinolin-6-yl)-1-((2-(trimethyl-silyl)ethoxy)methyl)-1H-imidazol-2-yl)-7-oxononyl) carbamoyl)-6-azaspiro[2.5]octane-6-carboxylate (11_F). LCMS (ESI) calc'd for $C_{46}H_{71}N_5O_{10}SSi$ [M+H]$^+$: 914.4, found: 914.6.

Step 7: 3-(2-(1-oxo-6-(2-((S)-7-oxo-1-((S)-6-azaspiro[2.5]octane-1-carboxamido)nonyl)-1-((2-(trimethylsilyl)ethoxy)methyl)-1H-imidazol-5-yl) isoquinolin-2(1H)-yl)ethoxy)propyl methanesulfonate (11_G)

TFA (1 mL, 12.98 mmol) was added to a stirred mixture of (S)-tert-butyl 1-(((S)-1-(5-(2-(2-(3-((methylsulfonyl)oxy) propoxy)ethyl)-1-oxo-1,2-dihydroisoquinolin-6-yl)-1-((2-(trimethylsilyl)ethoxy)methyl)-1H-imidazol-2-yl)-7-ox-ononyl)carbamoyl)-6-azaspiro[2.5]octane-6-carboxylate (11_F, 150 mg, 0.164 mmol) in DCM (5 mL) at 25° C. The resulting mixture was stirred at room temperature for 40 min. Aqueous NaHCO$_3$ (saturated, 3 mL) was added and the mixture was extracted with DCM (2×4 mL). The combined organic fractions were washed with brine (saturated, 2 mL), dried (Na$_2$SO$_4$), filtered and the solvent was evaporated under reduced pressure to give 3-(2-(1-oxo-6-(2-((S)-7-oxo-1-((S)-6-azaspiro[2.5]octane-1-carboxamido)nonyl)-1-((2-(trimethylsilyl)ethoxy)methyl)-1H-imidazol-5-yl)isoquino-lin-2(1H)-yl)ethoxy)propyl methanesulfonate (11_G). LCMS (ESI) calc'd for $C_{41}H_{63}N_5O_8SSi$ [M+H]$^+$: 814.1, found: 814.5.

Step 8: Compound 11_H

Cs$_2$CO$_3$ (53 mg, 0.163 mmol) was added to a stirred mixture of 3-(2-(1-oxo-6-(2-((S)-7-oxo-1-((S)-6-azaspiro [2.5]octane-1-carboxamido)nonyl)-1-((2-(trimethylsilyl) ethoxy)methyl)-1H-imidazol-5-yl)isoquinolin-2(1H)-yl) ethoxy)propyl methanesulfonate (11_G, 110 mg, 0.135 mmol) and sodium iodide (21 mg, 0.140 mmol) in acetoni-trile (10 mL) at 25° C. The resulting mixture was stirred at 80° C. for 12 h. The mixture was diluted with DCM (30 mL), washed with water (saturated, 2×10 mL), dried (Na$_2$SO$_4$), filtered and the solvent was evaporated under reduced pres-sure to give compound 11_H. LCMS (ESI) calc'd for $C_{40}H_{59}N_5O_5Si$ [M+H]$^+$: 718.4, found: 718.5.

Step 9: Compound 11

TFA (0.4 mL, 0.139 mmol) was added to a stirred mixture of 11_H (100 mg, 0.139 mmol) in DCM (0.2 mL) at 25° C. The resulting mixture was stirred at room temperature for 1 h. The mixture was concentrated to dryness. The residue was purified by preparative HPLC (reverse phase C-18 column), eluting with acetonitrile/water+0.1% TFA, to give 11. It was re-purified by Pre-TLC (DCM:MeOH=5:1) and preparative HPLC (reverse phase C-18 column), eluting with acetoni-trile/water+0.1% TFA, to give 11. LCMS (ESI) calc'd for $C_{34}H_{45}N_5O_4$ [M+H]$^+$: 588.4, found: 588.2. $^1$H NMR (400 MHz, MeOD) δ 7.95-8.17 (m, 1H), 7.74-7.94 (m, 2H), 7.41-7.53 (m, 1H), 7.17-7.36 (m, 1H), 6.25-6.52 (m, 1H), 5.05-5.18 (m, 1H), 4.03-4.20 (m, 1H), 3.78-3.91 (m, 1H), 3.55-3.75 (m, 3H), 3.39-3.50 (m, 1H), 3.23-3.29 (m, 1H), 3.08-3.22 (m, 2H), 2.79-3.07 (m, 1H), 2.47 (s, 5H), 1.87-2.20 (m, 5H), 1.71-1.85 (m, 1H), 1.45-1.69 (m, 5H), 1.21-1.43 (m, 5H), 1.00 (m, 4H).

Example 14

(3S,6S)-6-(6-oxooctyl)-22-oxa-5,8,18,26,33-pen-taazahexacyclo[24.2.2.1~7,10~0.1~11,15~0.1~14, 18~0.0~1,3~]tritriaconta-7,9,11(32),12,14,16-hexaene-4,31-dione (12)

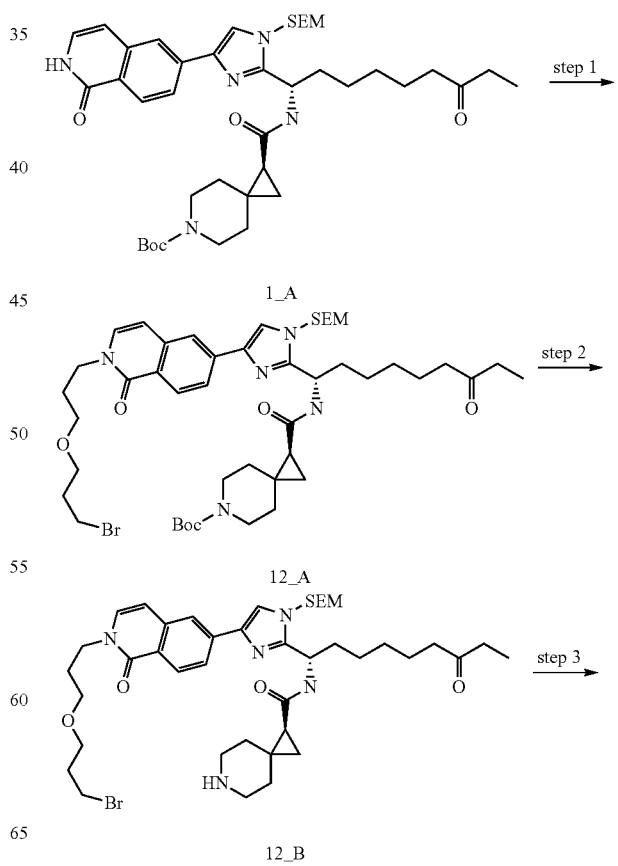

-continued

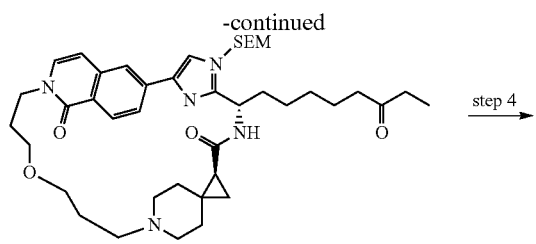

12_C

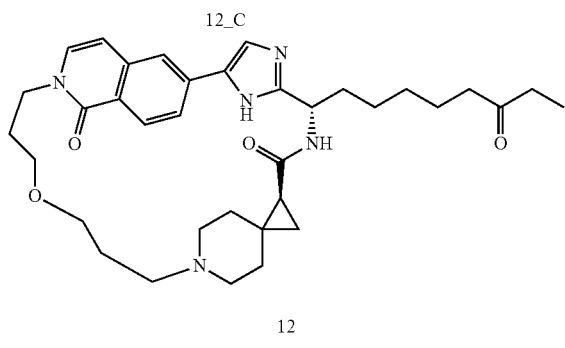

12

Step 1: Preparation of (S)-tert-butyl 1-(((S)-1-(4-(2-(3-(3-bromopropoxy)propyl)-1-oxo-1,2-dihydroisoquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (12_A)

Sodium iodide (0.359 g, 2.398 mmol) was added to a stirred mixture of Cs₂CO₃ (4.69 g, 14.39 mmol), (S)-tert-butyl 1-(((S)-7-oxo-1-(4-(1-oxo-1,2-dihydroisoquinolin-6-yl)-1-((2-(trimethylsilyl)ethoxy)methyl)-1H-imidazol-2-yl)nonyl)carbamoyl)-6-azaspiro[2.5]octane-6-carboxylate (1_A, 1.76 g, 2.398 mmol) and 1-bromo-3-(3-bromopropoxy)propane (2.493 g, 9.59 mmol) in MeCN (20 mL) at room temperature and the mixture was stirred at 50° C. for 6 h. The mixture was cooled, diluted with ethyl acetate (20 mL), washed with brine (saturated, 3×20 mL), dried (Na₂SO₄), filtered and the solvent was evaporated under reduced pressure. The residue was purified by silica gel column flash chromatography, eluting with EtOAc/petroleum ether=0-60% to give (S)-tert-butyl 1-(((S)-1-(4-(2-(3-(3-bromopropoxy)propyl)-1-oxo-1,2-dihydroisoquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (12_A). LCMS (ESI) calc'd for C₄₆H₇₀BrN₅O₇Si [M+H]⁺: 912.4, found: 914.4. ¹H NMR (400 MHz, CDCl₃) δ 8.40 (dd, J=4.4, 8.3 Hz, 1H), 7.92 (s, 1H), 7.78 (d, J=6.6 Hz, 1H), 7.35 (s, 1H), 7.14-7.22 (m, 1H), 7.14-7.22 (m, 1H), 6.43-6.58 (m, 2H), 5.62 (d, J=10.5 Hz, 1H), 5.11-5.29 (m, 2H), 4.28-4.40 (m, 1H), 3.88-4.08 (m, 1H), 3.18-3.79 (m, 10H), 2.34-2.44 (m, 4H), 1.98 (s, 1H), 1.71 (s, 6H), 1.53-1.65 (m, 6H), 1.45-1.51 (m, 1H), 1.44 (brs, 1H), 1.17-1.29 (m, 5H), 1.03 (t, J=7.5 Hz, 3H), 0.92-0.98 (m, 1H), 0.91 (s, 1H), 0.84 (dd, J=4.6, 8.11 Hz, 1H), −0.01-0.04 (m, 1H), 0.01 (s, 9H).

Step 2: Preparation of (S)-N-((S)-1-(4-(2-(3-(3-bromopropoxy)propyl)-1-oxo-1,2-dihydroisoquinolin-6-yl)-1-((2-(trimethylsilyl)ethoxy)methyl)-1H-imidazol-2-yl)-7-oxononyl)-6-azaspiro[2.5]octane-1-carboxamide (12_B)

HCl (1 mL, 4.00 mmol) was added to a stirred mixture of (S)-tert-butyl 1-(((S)-1-(4-(2-(3-(3-bromopropoxy)propyl)-1-oxo-1,2-dihydroisoquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (12_A, 100 mg, 0.110 mmol) in DCM (3 mL) at room temperature and the mixture was stirred at rt for 2 h. The mixture was concentrated to give (S)-N-((S)-1-(4-(2-(3-(3-bromopropoxy)propyl)-1-oxo-1,2-dihydroisoquinolin-6-yl)-1-((2-(trimethylsilyl)ethoxy)methyl)-1H-imidazol-2-yl)-7-oxononyl)-6-azaspiro[2.5]octane-1-carboxamide (12_B) which was used in the next step without further purification. LCMS (ESI) calc'd for C₄₁H₆₂BrN₅O₅Si [M+H]⁺: 812.4, found: 814.4.

Step 3: Preparation of 12_C

Potassium carbonate (70 mg, 0.506 mmol) was added to a stirred mixture of sodium iodide (20 mg, 0.133 mmol), and (S)-N-((S)-1-(4-(2-(3-(3-bromopropoxy)propyl)-1-oxo-1,2-dihydroisoquinolin-6-yl)-1-((2-(trimethylsilyl)ethoxy)methyl)-1H-imidazol-2-yl)-7-oxononyl)-6-azaspiro[2.5]octane-1-carboxamide (12_B, 100 mg, 0.123 mmol) in MeCN (20 mL) at room temperature and the mixture was stirred at 80° C. for 12 h. The mixture was cooled, diluted with dichloromethane (10 mL), washed with brine (saturated, 3×10 mL), dried (Na₂SO₄), filtered and the solvent was evaporated under reduced pressure. The residue was purified by silica gel column flash chromatography, eluting with MeOH/DCM=0-15% to give the 12_C. LCMS (ESI) calc'd for C₄₁H₆₁N₅O₅Si [M+H]⁺: 732.4, found: 732.7.

Step 4: Preparation of 12

TFA (3 ml, 0.055 mmol) was added in 12_C (40 mg, 0.055 mmol) at room temperature and the mixture was stirred at rt for 1 h. It was concentrated and purified by preparative reverse phase HPLC, eluting with acetonitrile/water, and then purified by preparative silica gel TLC to give compound 12. LCMS (ESI) calc'd for C₃₅H₄₇N₅O₄ [M+H]⁺: 602.4, found: 602.2. ¹H NMR (400 MHz, MeOD) δ 7.77-8.08 (m, 3H), 7.05-7.48 (m, 2H), 6.15-6.75 (m, 1H), 5.04-5.10 (m, 1H), 3.34-3.42 (m, 2H), 3.13-3.23 (m, 2H), 2.38-2.51 (m, 6H), 1.94-2.12 (m, 4H), 1.56 (s, 5H), 1.13-1.43 (m, 15H), 0.98 (t, J=6.8 Hz, 5H).

Example 15
(S)-6-ethyl-N-((S)-7-oxo-1-((Z)-9-oxo-11H-8-aza-1 (2,4)-imidazola-2(1,3)-benzenacyclononaphane-15-yl)nonyl)-6-azaspiro[2.5]octane-1-carboxamide (13)
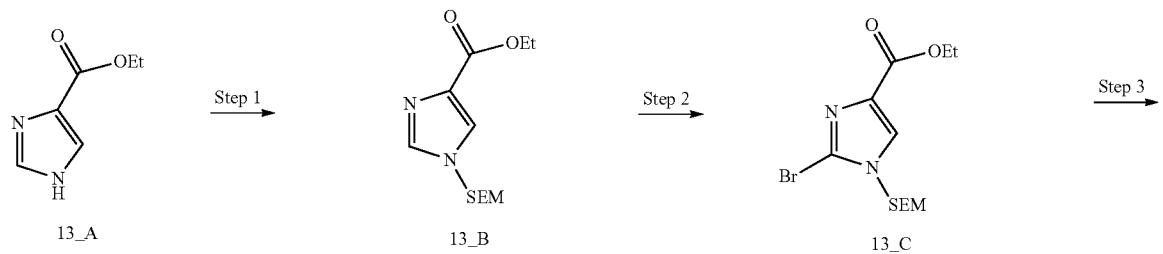
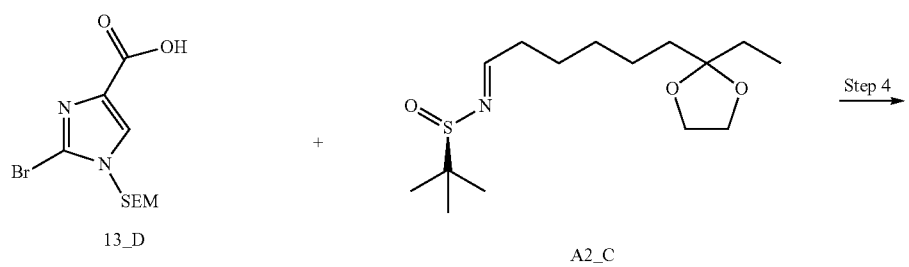
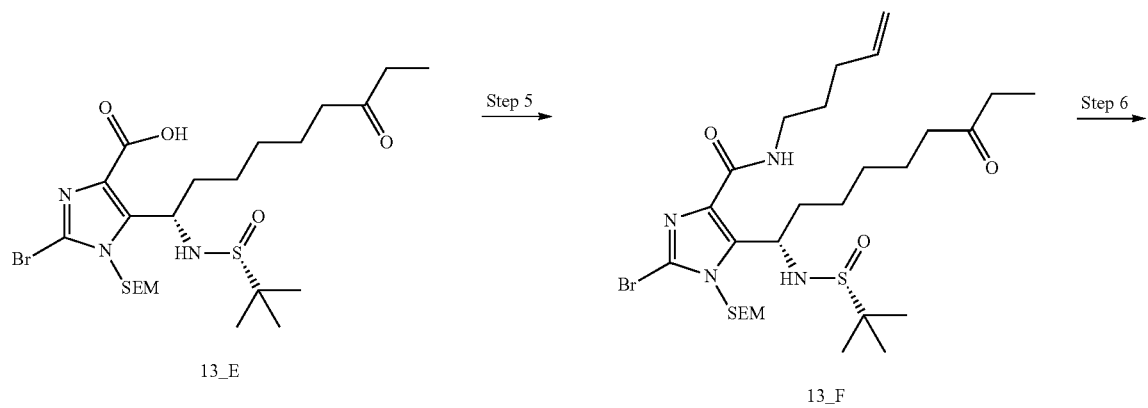
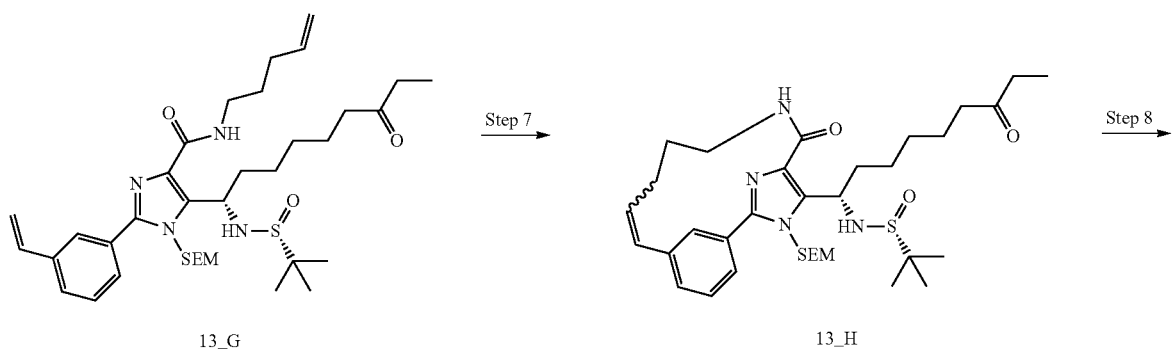

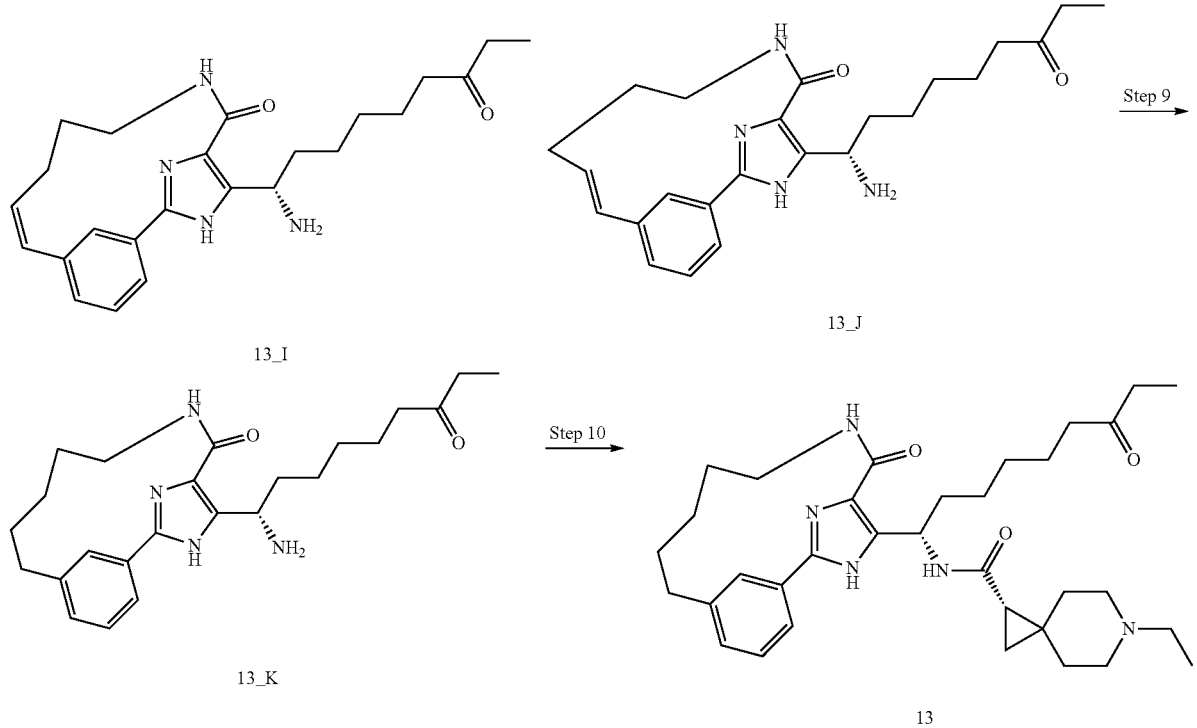

Step 1: Ethyl 1-((2-(trimethyl silyl)ethoxy)methyl)-1H-imidazole-4-carboxylate (13_B)

To a solution of ethyl 1H-imidazole-4-carboxylate (13_A) (560 mg, 4.00 mmol) in DMF (3996 μl) at ambient temperature was added NaH (160 mg, 4.00 mmol) and the reaction mixture stirred for 15 minutes. The mixture was cooled to 0° C. and SEM-Cl (780 μl, 4.40 mmol) was added dropwise. The reaction continued to stir for 1 hour before quenching with $H_2O$ (5 mL), taking up in EtOAc (20 mL), washing with $H_2O$ (15 mL×3), drying over $Na_2SO_4$, and concentrating. The residue was purified by column chromatography on silica (2-50% 1:3 EtOH:EtOAc/hexanes) to afford the title compound. MS: 271.1 (M+1).

Step 2: Ethyl 2-bromo-1-((2-(trimethylsilyl)ethoxy)methyl)-1H-imidazole-4-carboxylate (13_C)

To a solution of ethyl 1-((2-(trimethylsilyl)ethoxy)methyl)-1H-imidazole-4-carboxylate (13_B) (682 mg, 2.52 mmol) in chloroform (8407 μl) at ambient temperature was added NBS (494 mg, 2.77 mmol) and AIBN (41.4 mg, 0.252 mmol). The reaction mixture was heated to 60° C. for 2 hours before cooling and concentrating. The residue was purified by column chromatography on silica (2-40% 1:3 EtOH:EtOAc/hexanes) to afford the title compound. MS: 349.1, 351.1 (M+1).

Step 3: 2-bromo-1-((2-(trimethylsilyl)ethoxy)methyl)-1H-imidazole-4-carboxylic acid (13_D)

To a solution of ethyl 2-bromo-1-((2-(trimethylsilyl)ethoxy)methyl)-1H-imidazole-4-carboxylate (13_C) (5.00 g, 14.31 mmol) in EtOH (28.6 ml) at ambient temperature was added aqueous LiOH (9.54 ml, 28.6 mmol). The mixture was stirred for 3 hours before concentrating. The mixture was taken up in minimal DMSO and acidified with AcOH. The resulting solution was purified by column chromatography on C18 (5-95% MeCN/water with 0.1% TFA modifier) to afford the title compound. MS: 321.1, 323.1 (M+1).

Step 4: 2-bromo-5-((S)-1-(((R)-tert-butylsulfinyl)amino)-7-oxononyl)-1-((2-(trimethylsilyl)ethoxy)methyl)-1H-imidazole-4-carboxylic acid (13_E)

To a mixture of 2-bromo-1-((2-(trimethylsilyl)ethoxy)methyl)-1H-imidazole-4-carboxylic acid (13_D) (5.00 g, 15.56 mmol) in THF (78 ml) at -78° C. was added 2.0 M LDA (19.46 ml, 38.9 mmol) dropwise. The mixture stirred for 15 minutes before adding (R,E)-N-(6-(2-ethyl-1,3-dioxolan-2-yl)hexylidene)-2-methylpropane-2-sulfinamide (13_C) (7.08 g, 23.35 mmol) in THF (6 mL). The mixture stirred for 1 hour before quenching with a saturated solution of $NH_4Cl$ (150 mL) and warmed to ambient temperature. The mixture was extracted with EtOAc (100 mL×3), dried over $Na_2SO_4$, and concentrated. The resulting solution was purified by column chromatography on C18 (5-95% MeCN/water with 0.1% TFA modifier) to afford the title compound. MS: 580.4, 582.4 (M+1).

Step 5: 2-bromo-5-((S)-1-((R)-1,1-dimethylethylsulfinamido)-7-oxononyl)-N-(pent-4-en-1-yl)-1-((2-(trimethylsilyl)ethoxy)methyl)-1H-imidazole-4-carboxamide (13_F)

To a solution of 2-bromo-5-((S)-1-((R)-1,1-dimethylethylsulfinamido)-6-(2-ethyl-1,3-dioxolan-2-yl)hexyl)-1-((2-(trimethylsilyl)ethoxy)methyl)-1H-imidazole-4-carboxylic acid (13_E) (1.50 g, 2.401 mmol) in DCM (12.01 ml) at ambient temperature was added pent-4-en-1-amine (0.245 g, 2.88 mmol), DIPEA (0.629 ml, 3.60 mmol), and PyBOP (1.499 g, 2.88 mmol). The mixture was stirred for 1 hour before quenching with H₂O (20 mL), extracted with DCM (20 mL×3), dried over Na₂SO₄, and concentrated to give a crude mixture containing the title compound. MS: 647.5, 649.5 (M+1).

Step 6: 5-((S)-1-((R)-1,1-dimethylethylsulfinamido)-7-oxononyl)-N-(pent-4-en-1-yl)-1-((2-(trimethylsilyl)ethoxy)methyl)-2-(3-vinylphenyl)-1H-imidazole-4-carboxamide (13_G) To a mixture of 2-bromo-5-((S)-1-((R)-1,1-dimethylethylsulfinamido)-7-oxononyl)-N-(pent-4-en-1-yl)-1-((2-(trimethylsilyl)ethoxy)methyl)-1H-imidazole-4-carboxamide (13_F) (1555 mg, 2.40 mmol) in dioxane (9600 µl) at ambient temperature was added (3-vinylphenyl)boronic acid (710 mg, 4.80 mmol) and K₃PO₄ (1274 mg, 6.00 mmol) dissolved in water (2400 µl). Pd(Ph₃P)₄ (139 mg, 0.120 mmol) was added and the mixture was heated to 100° C. for 3 hours. The mixture was cooled, then water (25 mL) and EtOAc (25 mL) was added, it was extracted with EtOAc (25 mL×3), dried over Na₂SO₄, and concentrated. The resulting residue was purified by column chromatography on silica (5-70% 1:3 EtOH:EtOAc/hexanes) to afford the title compound. MS: 671.7 (M+1).

Step 7: (R)-2-methyl-N-((S)-7-oxo-1-((12Z)-9-oxo-11-((2-(trimethylsilyl)ethoxy)methyl)-11H-8-aza-1(2,4)-imidazola-2(1,3)-benzenacyclononaphan-3-en-15-yl)nonyl)propane-2-sulfinamide (13_H)

To a mixture of 5-((S)-1-((R)-1,1-dimethylethylsulfinamido)-7-oxononyl)-N-(pent-4-en-1-yl)-1-((2-(trimethylsilyl)ethoxy)methyl)-2-(3-vinylphenyl)-1H-imidazole-4-carboxamide (13_G) (300 mg, 0.447 mmol) in DCM (22.400 mL) at ambient temperature was added M71-S1Pr (36.7 mg, 0.045 mmol). The mixture was heated to 50° C. and stirred for 3 hours before it was concentrated. The resulting residue was purified by column chromatography on silica (2-70% 1:3 EtOH:EtOAc/hexanes) to afford the title compound. MS: 643.9 (M+1).

Step 8: (12Z,3Z)-15-((S)-1-amino-7-oxononyl)-11H-8-aza-1(2,4)-imidazola-2(1,3)-benzenacyclononaphan-3-en-9-one (13_I) and (12Z,3E)-15-((S)-1-amino-7-oxononyl)-11H-8-aza-1(2,4)-imidazola-2(1,3)-benzenacyclononaphan-3-en-9-one (13_J)

To a mixture of (R)-2-methyl-N-((S)-7-oxo-1-((12Z)-9-oxo-11-((2-(trimethylsilyl)ethoxy)methyl)-11H-8-aza-1(2,4)-imidazola-2(1,3)-benzenacyclononaphan-3-en-15-yl)nonyl)propane-2-sulfinamide (13_H) (120 mg, 0.187 mmol) in MeOH (1866 µl) at ambient temperature was added 4.0 M hydrogen chloride (187 µl, 0.747 mmol) in dioxanes. The mixture was stirred for 16 hours before the mixture was concentrated. The resulting residue was purified by mass triggered reverse phase HPLC (MeCN/water with 0.1% TFA modifier) to afford regioisomer 1 (13_1), MS: 409.6 (M+1), and regioisomer 2 (13_J), MS: 409.6 (M+1).

Step 9: (S,Z)-15-(1-amino-7-oxononyl)-11H-8-aza-1(2,4)-imidazola-2(1,3)-benzenacyclononaphan-9-one (13_K)

To a mixture of (12Z,3Z)-15-((S)-1-amino-7-oxononyl)-11H-8-aza-1(2,4)-imidazola-2(1,3)-benzenacyclononaphan-3-en-9-one (13_I) (20.0 mg, 0.049 mmol) in Methanol (979 µl) was added Pd/C (1.042 mg, 9.79 µmol). A hydrogen balloon was added and the mixture was stirred for 1 hour. The mixture was filtered through a pad of celite and the filtrate was concentrated to afford the title compound. MS: 411.6 (M+1).

Step 10: (S)-6-ethyl-N-((S)-7-oxo-1-((Z)-9-oxo-11H-8-aza-1(2,4)-imidazola-2(1,3)-benzenacyclononaphane-15-yl)nonyl)-6-azaspiro[2.5]octane-1-carboxamide (13)

To a solution of (S)-6-ethyl-6-azaspiro[2.5]octane-1-carboxylic acid (13.46 mg, 0.073 mmol) in DMF (974 µl) at ambient temperature was added DIPEA (25.5 µl, 0.146 mmol) and HATU (27.8 mg, 0.073 mmol). The mixture was stirred for 10 minutes before adding to a vial containing (S,Z)-15-(1-amino-7-oxononyl)-11H-8-aza-1(2,4)-imidazola-2(1,3)-benzenacyclononaphan-9-one (13_K) (20 mg, 0.049 mmol). The mixture stirred for 1 hour before quenching with a few drops of AcOH. The resulting solution was purified by mass triggered reverse phase HPLC (MeCN/water with 0.1% TFA modifier) to afford the title compound. MS: 576.8 (M+1). NMR: 1H NMR (500 MHz, DMSO-d6) δ 9.07 (d, J=70.1 Hz, 1H), 8.87 (s, 1H), 8.11 (s, 1H), 7.95 (s, 1H), 7.70 (s, 1H), 7.39 (d, J=6.8 Hz, 1H), 7.28 (s, 1H), 5.40 (s, 1H), 3.44 (d, J=33.5 Hz, 2H), 3.25 (s, 3H), 3.14-3.03 (m, 1H), 2.89 (s, 3H), 2.66 (s, 2H), 2.34 (ddd, J=18.3, 12.5, 7.3 Hz, 5H), 2.02 (d, J=12.5 Hz, 2H), 1.82 (d, J=15.1 Hz, 1H), 1.76-1.52 (m, 6H), 1.46-1.26 (m, 5H), 1.17 (t, J=7.2 Hz, 5H), 1.00 (d, J=34.1 Hz, 3H), 0.87 (q, J=7.1 Hz, 4H).

The following examples were prepared in a similar manner to the procedures described above using appropriate starting materials described previously or commercially available:

| | Structure | Name | Exact Mass [M + H]+ | Observed [M + H]+ |
|---|---|---|---|---|
| 14 | 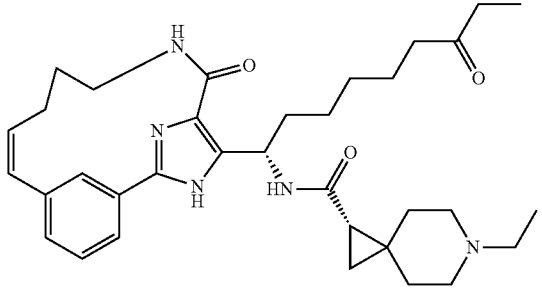 [SMILES: CCC(=O)CCCCC[C@H](NC(=O)[C@H]1CC12CCN(CC)CC2)c1[nH]c2nc1C(=O)NCCC/C=C\c1cccc-2c1] | (1S)-6-ethyl-N-{(1S)-7-oxo-1-[(11Z)-6-oxo-3,7,18-triazatricyclo[11.3.1.1~2,5~]octadeca-1(17),2(18),4,11,13,15-hexaen-4-yl]nonyl}-6-azaspiro[2.5]octane-1-carboxamide | Calc'd 574.4, found | 574.7 |

| Structure | Name | Exact Mass [M + H]+ | Observed [M + H]+ |
|---|---|---|---|
| 15 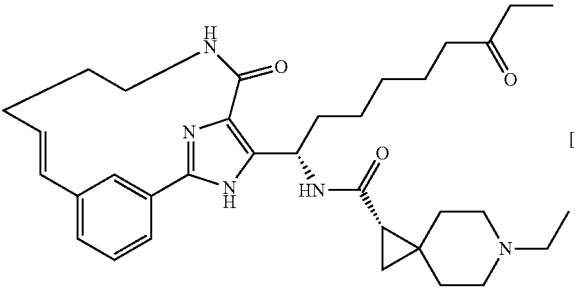 [SMILES: CCC(=O)CCCCC[C@H](NC(=O)[C@H]1CC12CCN(CC)CC2)c1[nH]c2nc1C(=O)NCCC/C=C/c1cccc-2c1] | (1S)-6-ethyl-N-{(1S)-7-oxo-1-[(11E)-6-oxo-3,7,18-triazatricyclo[11.3.1.1~2,5~]octadeca-1(17),2(18),4,11,13,15-hexaen-4-yl]nonyl}-6-azaspiro[2.5]octane-1-carboxamide | Calc'd 574.4, found | 574.7 |

Human HDAC Enzyme Inhibitor FLUOR-DE-LYS Assay
Materials

Recombinant human HDAC8 (catalog number BMIL-SE145-0100) and HDAC10 (catalog number BML-SE559-0050) enzymes, HDAC substrates BML-KI104 and BML-K1178, and HLDAC developer solutions BMIL-KI105 and BML-K1176 were purchased from Enzo Life Sciences (Farmingdale, N.Y.). Recombinant human HDAC5 and HDAC11 were purchased from BPS Bioscience (San Diego, Calif.)(catalog numbers 50045 and 50021). Substrate Boc-Lys(TFA)-AMC was obtained from Bachem (Bupendorf, Switzerland) (catalog number 1-1985). HDAC inhibitor suberoylanilide hydroxamic acid (SAHA) was obtained from Indofine (Hillsborough Township, N.J.) and trichostatin A (TSA) was obtained from Sigma-Aldrich (St. Louis, Mo.). D-myo inositol-1,4,5,6-tetraphosphate potassium salt (IP$_4$) was obtained from Carbosynth (San Diego, Calif.) (catalog MI 16761). HEPES pH 8.0 was obtained from Boston BioProducts (Ashland, Mass.), Tween-20 from Fisher Scientific (Hampton, N.H.) (catalog number BP337), TCEP from Calbiochem and 7.5% bovine serum albumin (BSA) from Life Technologies (Carlsbad, Calif.) (catalog number 15260037). 384-well, black assay plates were obtained from Corning (Corning, N.Y.) (catalog number 3575).

Recombinant human HDAC1, HDAC2, and HDAC3/SMRT heterodimer were prepared by Merck Research Laboratories. Full length human HDAC1-FLAG was stably expressed in HEK-293F cells and purified using an anti-FLAG affinity chromatography with FLAG peptide (100 μg/ml) elution. The final concentration of HDAC1 was 1.98 uM by Western Blot analysis and 1.39 uM by active site titration. Full length human HDAC2-FLAG was expressed in baculovirus infected Sf9 cells and purified using an anti-FLAG affinity chromatography with FLAG peptide (100 μg/ml) elution. The eluted protein was then passed over an anti-HDAC1 immunoaffinity column to remove any complexes containing HDAC1. The final concentration of HDAC2 was 16.8 uM by Western Blot analysis and 7.6 uM by active site titration. Full length human HDAC3-FLAG was expressed in HEK-293F cells along with SMRT (amino acids 1-899)-6×His; plasmid APP-0024) and purified using an anti-FLAG affinity chromatography with FLAG peptide (100 μg/ml) elution. The eluted protein was then passed over an anti-HDAC1 immunoaffinity column to remove any complexes containing HDAC1. The final concentration of the HDAC3/SMRT complex was 2.03 uM by Western Blot analysis and 1.37 uM by active site titration.

HDAC Inhibition Assays

The histone deacetylase activities of HDAC1, HDAC2, HDAC3, HDAC6, and HDAC8 were measured in modified Fluor-de-Lys assays in 384-well format. In this assay, HDAC enzymes are initially incubated with an ε-acetyl (or -trifluoroacetyl)-L-lysine-containing substrate with a C-terminal amide having aminomethylcoumarin as the amine component. HDACs cleave the ε-acetyl group, rendering the resulting product susceptible to AMC cleavage by trypsin. The released AMC is then detected by its fluorescence.

The HDAC 1, 2 assays employed buffer A, which contained 20 mM HEPES, pH 8.0, 1 mM MgCl$_2$, 137 mM NaCl, 2.7 mM KCl, 0.05% BSA. The HDAC3/SMRT assay employed buffer B, consisting of 20 mM HEPES, pH 8.0, 1 mM MgCl$_2$, 50 mM NaCl, 2.7 mM KCl, 0.05% BSA, 0.005% Tween 20, and 10 μM IP4. The HDAC6 assay employed buffer C, consisting of 20 mM HEPES, pH 8.0, 1 mM MgCl$_2$, 137 mM NaCl, 2.7 mM KCl, 0.5 mM TCEP (Calbiochem) and 0.05% BSA. The HDAC8 assay employed buffer D, consisting of 20 mM HEPES, pH 8.0, 1 mM MgCl$_2$, 100 mM NaCl, 20 mM KCl, 0.1% n-octyl-β-D-glucoside (Anatrace, Maumee, Ohio) and 0.05% BSA. All steps were performed at room temperature (23° C.). The assay was performed by pre-incubating serial dilutions of test compounds with the target HDAC prior to initiation with substrate. Each compound was titrated in a 10-point dose response, using a 1:3 fold dilution scheme, with 0.15 ul of solution added by ECHO555 to the plate, followed by the addition of 20 μl of the appropriate HDAC isoform diluted in appropriate assay buffer. The incubation was allowed to proceed for 3 hours, then the appropriate substrate diluted in assay buffer (final substrate concentration ~K$_m$) was added and the reaction allowed to proceed for 60 min. Final conditions used for each assay were: 1. HDAC 1, 0.3 nM total enzyme, 20 μM substrate BML-KI104; 2. HDAC 2, 1.5 nM total enzyme, 40 μM substrate BML-KI104; 3. HDAC 3/SMRT, 0.3 nM total enzyme, 20 μM substrate BML-KI104; 4. HDAC 6, 1.3 nM total enzyme, 2.5 μM substrate BML-KI104; 5. HDAC 8, 1.3 nM total enzyme, 200 μM substrate BML-KI178; the final high dose of test compound was 30 μM. For potent compounds, 900 nM was used as the final high dose. The reactions were stopped and developed by addition of 30 ul of HDAC developer solution containing a saturating level of HDAC inhibitor as follows: 1. HDACs 1, 2, 3 and 6, developer BML-KI105 (stock diluted 1:125, containing 20 uM SAHA, 2. HDAC 8, developer BML-K1176 (1:100 plus 40 uM SAHA, and the plates were shaken to assure good mixing, briefly centrifuged, incubated for 30 minutes at room temperature and then the fluorescence intensity (excitation 380 nm, emission 460 nm) measured using a PHERAstar plate reader. For each assay plate, both minimal inhibition (100% DMSO; 0% inhibition) and maximal inhibition (either 10 uM SAHA or 100 uM TSA; 100% inhibition) controls were added. For data analysis, background subtracted product (fluorescence) vs. time data for each inhibitor concentration was fitted using a 4-parameter fit.

All compounds prepared were tested in the binding assays with HDAC1, 2, 3, 6 and 8.

KARN Assay

Cell Maintenance

KARN cells (Jurkat 2C4) were licensed from the laboratory of Dr. John Kam, Case Western Reserve University, School of Medicine. The details regarding this cell line are published (Pearson, R., Kin, Y. K., Hokello, J., Lassen, K., Friedman, J., Tyagi, M., Karn, J., 2008, J. Virol. 82:12291-12303). The cells were grown in a T175 flask (Thermo Fisher, catalog number 159910) in RPMI 1640 containing L-glutamine and phenol red (Life Technologies, catalog number 11875-085), 5% heat inactivated fetal bovine serum (FBS; Life Technologies, catalog number 10100-147) and 100 µg/ml Penicillin-Streptomycin (Life Technologies, catalog number 15140-122) at 37° C. An atmosphere of 5% $CO_2$ and 90% humidity was used for all culture work. Cells were split and reseeded into T175 flasks at a density of $0.2×10^6$ cells/ml, in 40 ml of media, every 3-4 days.

KARN Assay

Day 1: After the 3-4 day growth period, the cells were transferred from the T175 flask to a 50 ml conical tube and gently pelleted at 1000 rpm for 5 minutes. The supernatant was removed and the cells gently resuspended in assay media RPMI 1640 medium containing L-glutamine but without Phenol Red (Life Technologies, catalog number 11835-030), 5% FBS and 100 µg/ml Penicillin-Streptomycin, and then reseeded such that the original flask is now divided into two T175 flasks. These flasks were returned to the incubator.

Day 2: Cell Preparation: The next day, the cells were transferred from each T175 flask to an individual 50 ml conical tube and gently pelleted at 1000 rpm for 5 minutes. The cells were gently resuspended in assay media (30 ml) and pelleted again. The cell pellets were each resuspended in 30 ml of RPMI 1640 medium containing L-glutamine but without Phenol Red, 100 µg/ml Penicillin-Streptomycin and containing either 0.1% or 5% normal human serum (NHS; Biospecialty, Colmar, Pa., catalog number 115-00 Anticoagulant free). The cells were counted using the ViCell (Beckman Coulter, Brea, Calif.) and diluted as necessary. A Multidrop (Combi, Thermo Scientific, Waltham, Mass.) with a sterile head was used to seed the cells into the wells of a 384-well solid black plate with lid (Perkin Elmer, Waltham, Mass., catalog number 6007660) at 4000 cells/30 µl/well for the 5% NHS assay media and 6000 cells/30 µl/well for 0.1% NHS assay. The plates were covered and returned to the incubator prior to compound addition.

Compound Preparation: Solutions of control inhibitor suberoylanilide hydroxamic acid (SAHA; Sigma, catalog number SML0061) and test compounds in 100% DMSO were titrated into 384-well polypropylene plates (Labcyte, San Jose, Calif., catalog number P-05525) using a 20-point dose response and 2-fold dilutions. The reference compounds, DMSO and SAHA were then added to the compound plate. Using the Access system (Labcyte), 120 nl of these inhibitor and control solutions were added to the individual wells of the plates containing the cells, and the plates were then returned to the incubator for ~20 hr (range from 18-24 hr). The final high concentration for SAHA and the test compounds in the assays was 40 µM. The final DMSO concentration in all wells was 0.4%. The minimal induction reference compound used was DMSO and the maximal induction reference compound used was SAHA (2 µM final concentration in the assay).

Day 3: The luciferase detection reagent was prepared by transferring the contents of one bottle of Steady-Glo buffer to one bottle of Steady-Glo substrate (Steady-Glo Luciferase Assay System, Promega, Madison, Mich., catalog number E2520), followed by gently mixing until the substrate was thoroughly dissolved and the solution was equilibrated to room temperature. The cell culture assay plates were removed from the incubator and brought to room temperature (15 min). The Steady-Glo Reagent was added to the plates (30 µl/well), which were then covered with a black lid and incubated for 10 minutes at room temperature. The plates were then read for luminescence on an Envision (Perkin Elmer) using the ultrasensitive mode (US LUM), 0.1 counts per second and 384-well aperture. Luminescence counts in the DMSO reference wells were considered as 0% induction, while those in the 2 µM SAHA reference wells were considered as 100% induction. Dose response curves were plotted as test compound concentration (X-axis) vs. percent activation (Y-axis) using a 4-parameter fit based on the Levenberg-Marquardt algorithm.

The HDAC and Kam potency data of compounds 1-12 are as follows:

|  | HDAC-1 $IC_{50}$ (nM) | HDAC-2 $IC_{50}$ (nM) | HDAC-3 $IC_{50}$ (nM) | HDAC-6 $IC_{50}$ (nM) | HDAC-8 $IC_{50}$ (nM) | Karn $EC_{50}$ with 0.1% NHS (nM) | Karn $EC_{50}$ with 5% NHS (nM) |
|---|---|---|---|---|---|---|---|
| 1 | 0.20 | 0.43 | 0.061 | >900 | >900 | 14 | 16 |
| 2 | 45 | 176 | 24 | >900 | >900 | 6267 | 9059 |
| 3 | 2.7 | 7.0 | 0.86 | >900 | >900 | 73 | 76 |
| 4 | 0.61 | 35 | 7.1 | >900 | >900 | >40000 | >40000 |
| 5 | 0.11 | 0.31 | 0.13 | 218 | >900 | 11 | 12 |
| 6 | 28 | 595 | 248 | >900 | >900 | 2500 | 3513 |
| 7 | 16 | 260 | 57 | 858 | >900 | 5147 | 4734 |
| 8 | 42 | 287 | 130 | >900 | >900 | >40000 | >40000 |
| 9 | 24 | 335 | 150 | >900 | >900 | >40000 | >40000 |
| 10 | 19 | 148 | 49 | >900 | >900 | 844 | 867 |
| 11 | 0.11 | 22 | 2.6 | >900 | >900 | >40000 | >40000 |
| 12 | 0.33 | 8.5 | 0.32 | >900 | 808 | 1788 | 1985 |

-continued

| | HDAC-1 IC$_{50}$ (nM) | HDAC-2 IC$_{50}$ (nM) | HDAC-3 IC$_{50}$ (nM) | HDAC-6 IC$_{50}$ (nM) | HDAC-8 IC$_{50}$ (nM) | Karn EC$_{50}$ with 0.1% NHS (nM) | Karn EC$_{50}$ with 5% NHS (nM) |
|---|---|---|---|---|---|---|---|
| 13 | 109 | >900 | 103 | >900 | >900 | >40000 | 12000 |
| 14 | 133 | 572 | 113 | >90 | >900 | 1464 | 2875 |
| 15 | 21 | 223 | 18 | >900 | >900 | 5235 | 19340 |

Treatment or Prevention of HIV Infection

The Compounds of Formula I and Ia may be useful in the activation of HIV latency, the treatment of HIV infection and/or reduction of the likelihood or severity of symptoms of HIV infection and the inhibition of HIV viral replication and/or HIV viral production in a cell-based system. For example, the Compounds of Formula I and Ia may be useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one Compound of Formula I and Ia or a pharmaceutically acceptable salt or prodrug thereof. In a specific embodiment, the amount administered is effective to treat or prevent infection by HIV in the subject. In another specific embodiment, the amount administered is effective to inhibit HIV viral replication and/or viral production in the subject. In one embodiment, the HIV infection has progressed to AIDS.

The Compounds of Formula I and Ia are also useful in the preparation and execution of screening assays for antiviral compounds. For example the Compounds of Formula I and Ia may be useful for identifying resistant HIV cell lines harboring mutations, which are excellent screening tools for more powerful antiviral compounds. Furthermore, the Compounds of Formula I and Ia may be useful in establishing or determining the binding site of other antivirals to the HIV Integrase.

The compositions and combinations of the present invention may be useful for treating a subject suffering from infection related to any HIV genotype.

Combination Therapy

In another embodiment, the present methods for treating or preventing HIV infection can further comprise the administration of one or more additional therapeutic agents which are not Compounds of Formula I and Ia.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: I at least one Compound of Formula I and Ia (which may include two or more different Compounds of Formula I and Ia), or a pharmaceutically acceptable salt or prodrug thereof, and (ii) at least one additional therapeutic agent that is other than a Compound of Formula I or Ia, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Tricyclic Heterocycle Compound and an additional therapeutic agent may be present in fixed amounts (dosage amounts) in a single dosage unit (e.g., a capsule, a tablet and the like).

In one embodiment, at least one Compound of Formula I or Ia is administered during a time when the additional therapeutic agent(s) exert their prophylactic or therapeutic effect, or vice versa.

In another embodiment, at least one Compound of Formula I or Ia and the additional therapeutic agent(s) are administered in doses commonly employed when such agents are used as monotherapy for treating a viral infection.

In another embodiment, at least one Compound of Formula I or Ia and the additional therapeutic agent(s) are administered in doses lower than the doses commonly employed when such agents are used as monotherapy for treating a viral infection.

In still another embodiment, at least one Compound of Formula I or Ia and the additional therapeutic agent(s) act synergistically and are administered in doses lower than the doses commonly employed when such agents are used as monotherapy for treating a viral infection.

In one embodiment, at least one Compound of Formula I or Ia and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that may be treated or prevented using the combination therapy methods of the present invention include, but are not limited to, those listed above.

In one embodiment, the viral infection is HIV infection.

In another embodiment, the viral infection is AIDS.

The at least one Compound of Formula I or Ia and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Compound of Formula I or Ia and the additional therapeutic agent(s) may inhibit the resistance of a viral infection to these agents.

As noted above, the present invention is also directed to use of a compound of Formula I or Ia with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

| Name | Trade Name |
| --- | --- |
| abacavir, ABC | Ziagen ® |
| abacavir + lamivudine | Epzicom ® |
| abacavir + lamivudine + zidovudine | Trizivir ® |
| amprenavir | Agenerase ® |
| atazanavir | Reyataz ® |
| AZT, zidovudine, azidothymidine | Retrovir ® |
| darunavir | Prezista ® |
| ddC, zalcitabine, dideoxycytidine | Hivid ® |
| ddI, didanosine, dideoxyinosine | Videx ® |
| ddI (enteric coated) | Videx EC ® |
| delavirdine, DLV | Rescriptor ® |
| dolutegravir | Tivicay ® |
| doravirine | Pifeltro ® |
| doravirine + lamivudine + tenofovir DF | Delstrigo ® |
| efavirenz, EFV | Sustiva ®, Stocrin ® |
| efavirenz + emtricitabine + tenofovir DF | Atripla ® |
| EFdA (4'-ethynyl-2-fluoro-2'-deoxyadenosine) | |
| emtricitabine, FTC | Emtriva ® |
| emtricitabine + tenofovir DF | Truvada ® |
| emvirine | Coactinon ® |
| enfuvirtide | Fuzeon ® |
| enteric coated didanosine | Videx EC ® |
| etravirine, TMC-125 | Intelence ® |
| fosamprenavir calcium | Lexiva ® |
| indinavir | Crixivan ® |
| lamivudine, 3TC | Epivir ® |
| lamivudine + zidovudine | Combivir ® |
| lopinavir | |
| lopinavir + ritonavir | Kaletra ® |
| maraviroc | Selzentry ® |
| nelfinavir | Viracept ® |
| nevirapine, NVP | Viramune ® |
| raltegravir | Isentress ® |
| rilpivirine, TMC-278 | Edurant ® |
| ritonavir | Norvir ® |
| saquinavir | Invirase ®, Fortovase ® |
| stavudine, d4T, didehydrodeoxythymidine | Zerit ® |
| tenofovir DF (DF = disoproxil fumarate), TDF | Viread ® |
| tipranavir | Aptivus ® |

Some of the drugs listed in the table are used in a salt form; e.g., abacavir sulfate, indinavir sulfate, atazanavir sulfate, nelfinavir mesylate.

In one embodiment, one or more anti-HIV drugs are selected from, raltegravir, lamivudine, abacavir, ritonavir, darunavir, atazanavir, emtricitabine, tenofovir, rilpivirine, doravirine, EFdA and lopinavir.

In another embodiment, the compound of Formula I or Ia is used in combination with raltegravir.

In another embodiment, the compound of Formula I or Ia is used in combination with lamivudine.

In still another embodiment, the compound of Formula I or Ia is used in combination atazanavir.

In another embodiment, the compound of Formula I or Ia is used in combination with darunavir.

In another embodiment, the compound of Formula I or Ia is used in combination with rilpivirine.

In one embodiment, the compound of Formula I or Ia is used in combination with lamivudine and abacavir.

In another embodiment, the compound of Formula I or Ia is used in combination with EFdA.

In another embodiment, the compound of Formula I or Ia is used in combination with emtricitabine and tenofovir.

In still another embodiment, the compound of Formula I or Ia is used in combination doravirine.

In another embodiment, the compound of Formula I or Ia is used in combination with ritonavir and lopinavir.

In one embodiment, the compound of Formula I or Ia is used in combination with abacavir and lamivudine.

In another embodiment, the compound of Formula I or Ia is used in combination with lopinavir and ritonavir.

In one embodiment, the present invention provides pharmaceutical compositions comprising (i) a compound of Formula I or Ia or a pharmaceutically acceptable salt or prodrug thereof; (ii) a pharmaceutically acceptable carrier; and (iii) one or more additional anti-HIV agents selected from lamivudine, abacavir, ritonavir and lopinavir, or a pharmaceutically acceptable salt or prodrug thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of Formula I or Ia or a pharmaceutically acceptable salt or prodrug thereof and (ii) one or more additional anti-HIV agents selected from lamivudine, abacavir, ritonavir and lopinavir, or a pharmaceutically acceptable salt or prodrug thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57$^{th}$ edition (2003), the 58$^{th}$ edition (2004), the 59$^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection may be determined by the attending clinician, taking into consideration the approved doses and dosage regimen in the package insert; the age, sex and general health of the subject; and the type and severity of the viral infection or related disease or disorder. When administered in combination, the compounds of the invention and the other agent(s) may be administered simultaneously (i.e., in the same composition or in separate compositions one right after the other) or sequentially. This is particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Compounds of Formula I and Ia may be administered as a component of a composition that comprises a pharmaceutically acceptable carrier or vehicle. The present invention provides pharmaceutical compositions comprising an effective amount of at least one Compound of Formula I or Ia and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules may be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Compounds of Formula I and Ia are administered orally.

In another embodiment, the one or more Compounds of Formula I and Ia are administered intravenously.

In one embodiment, a pharmaceutical preparation comprising at least one Compound of Formula I or Ia is in unit dosage form. In such form, the preparation is subdivided into unit doses containing effective amounts of the active components.

Compositions may be prepared according to conventional mixing, granulating or coating methods, respectively, and the present compositions can contain, in one embodiment, from about 0.1% to about 99% of the Compound(s) of Formula I or Ia by weight or volume. In various embodiments, the present compositions can contain, in one embodiment, from about 1% to about 70% or from about 5% to about 60% of the Compound(s) of Formula I or Ia by weight or volume.

The compounds of Formula I and Ia may be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions may be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The unit dosages of the Compounds of Formula I and Ia may be administered at varying frequencies. In one embodiment, a unit dosage of a Compound of Formula I or Ia may be administered once daily. In another embodiment, a unit dosage of a Compound of Formula I or Ia may be administered twice weekly. In another embodiment, a unit dosage of a Compound of Formula I or Ia may be administered once weekly. In still another embodiment, a unit dosage of a Compound of Formula I or Ia may be administered once biweekly. In another embodiment, a unit dosage of a Compound of Formula I or Ia may be administered once monthly. In yet another embodiment, a unit dosage of a Compound of Formula I or Ia may be administered once bimonthly.

In another embodiment, a unit dosage of a Compound of Formula I or Ia may be administered once every 3 months. In a further embodiment, a unit dosage of a Compound of Formula I or Ia may be administered once every 6 months. In another embodiment, a unit dosage of a Compound of Formula I or Ia may be administered once yearly.

The amount and frequency of administration of the Compounds of Formula I and Ia will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Compound of Formula I or Ia, or a pharmaceutically acceptable salt or prodrug of said compound and a pharmaceutically acceptable carrier, vehicle or diluent.

In another aspect the present invention provides a kit comprising an amount of at least one Compound of Formula I or Ia, or a pharmaceutically acceptable salt or prodrug of said compound and an amount of at least one additional therapeutic agent listed above, wherein the amounts of the two or more active ingredients result in a desired therapeutic effect. In one embodiment, the one or more Compounds of Formula I or Ia and the one or more additional therapeutic agents are provided in the same container. In one embodiment, the one or more Compounds of Formula I or Ia and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound of the formula:

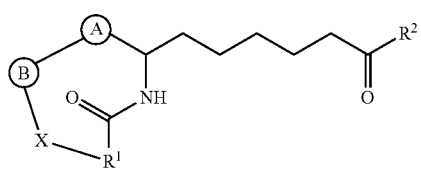

wherein

Ⓐ is a five-membered heteroaryl ring which is optionally substituted with halo, cyano or $C_{1-3}$ alkyl;

Ⓑ is heteroaryl, which may be bicyclic or tricyclic, is optionally substituted with one to three groups independently selected from the group consisting of halo, oxo, cyano, $R^3$ and $OR^3$;

$R^1$ is
(a) heterocyclyl, which may be monocyclic or bicyclic,
(b) —$C_{1-3}$ alkyl-N($R^3$)—,
wherein said heterocyclyl groups are optionally substituted with one to two groups independently selected from the group consisting of halo, cyano, oxo, $R^3$ and $OR^3$;

X is —$(CH_2)_n$—, —$(CH_2)_m CH=CH(CH_2)_p$— or —$(CH_2)_m$—O—$(CH_2)_p$—;

$R^2$ is $C_{1-6}$ alkyl;

each $R^3$ is independently hydrogen or $C_{1-6}$ alkyl, which is optionally substituted with one to three halo;

n is an integer between four and eight;
m is an integer between zero and four;
p is an integer between one and five;
or a pharmaceutically acceptable salt thereof.

2. The compound of claim 1 wherein

Ⓐ is imidazolyl or oxazolyl; or a pharmaceutically acceptable salt thereof.

3. The compound of claim 1 wherein

Ⓑ is dihydroisoquinolinyl, tetrahydroepaminonaphthalenyl or quinolinyl, wherein said dihydroisoquinolinyl, tetrahydroepaminonaphthalenyl or quinolinyl groups are optionally substituted with oxo or $OR^3$; or a pharmaceutically acceptable salt thereof.

4. The compound of claim 1 wherein $R^1$ is azaspirooctanyl or —$CH_2N(CH_3)$—; or a pharmaceutically acceptable salt thereof.

5. The compound of claim 1 wherein $R^2$ is ethyl; or a pharmaceutically acceptable salt thereof.

6. The compound of claim 1 wherein $R^3$ is hydrogen or methyl, or a pharmaceutically acceptable salt thereof.

7. A compound selected from

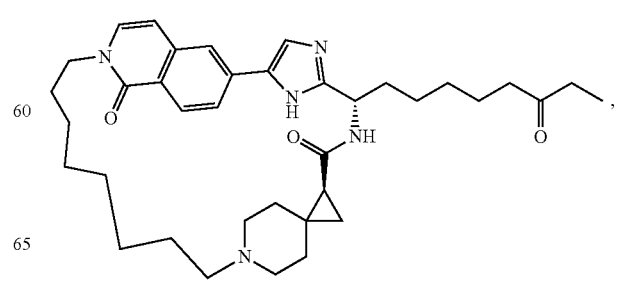

-continued
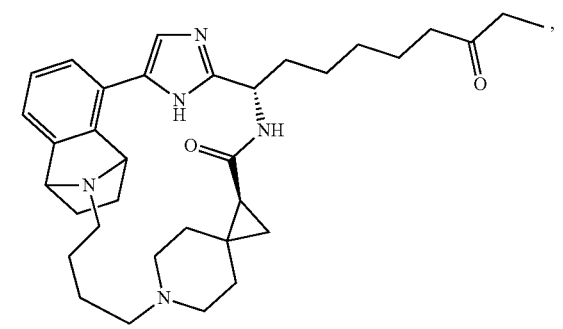
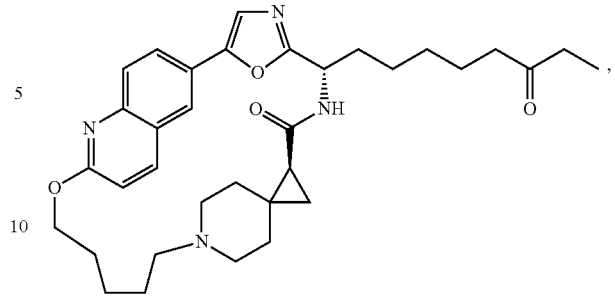

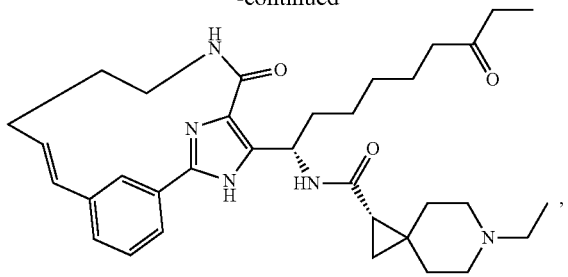

or a pharmaceutically acceptable salt thereof.

8. A pharmaceutical composition comprising an effective amount of a compound of claim 1, or a pharmaceutically acceptable salt thereof, and a pharmaceutically acceptable carrier.

9. A method for the inhibition of HDAC in a subject in need thereof which comprises administering to the subject an effective amount of a compound of claim 1, or a pharmaceutically acceptable salt thereof.

10. A method for the treatment of infection by HIV or for the treatment, prophylaxis, or delay in the onset or progression of AIDS in a subject in need thereof, which comprises administering to the subject an effective amount of compound of claim 1, or a pharmaceutically acceptable salt thereof.

11. The pharmaceutical composition of claim 8, further comprising one or more additional therapeutic agents selected from lamivudine, abacavir, ritonavir, darunavir, atazanavir, emtricitabine, tenofovir, rilpivirine, doravirine, EFdA and lopinavir.

12. The method of claim 10, further comprising administering to the subject one or more additional therapeutic agents selected from lamivudine, abacavir, ritonavir, darunavir, atazanavir, emtricitabine, tenofovir, rilpivirine, doravirine, EFdA and lopinavir, wherein the amounts administered of the compound of claim 1 and the one or more additional therapeutic agents, are together effective to treat infection by HIV or to treat, prevent or delay the onset or progression of AIDS.

* * * * *